United States Patent [19]
Ohuchida et al.

[11] Patent Number: 5,534,536
[45] Date of Patent: Jul. 9, 1996

[54] FUSED PHENOL DERIVATIVES

[75] Inventors: Shuichi Ohuchida; Fumio Nambu; Masaaki Toda, all of Osaka, Japan

[73] Assignee: Ono Pharmaceuticals Co. Ltd., Osaka, Japan

[21] Appl. No.: 294,015

[22] Filed: Aug. 23, 1994

[30] Foreign Application Priority Data

Aug. 24, 1993 [JP] Japan .................................. 5-231004

[51] Int. Cl.$^6$ ...................... A61K 31/415; C07D 405/06
[52] U.S. Cl. .................. 514/397; 548/311.4; 548/301.1; 546/15; 546/282.7; 546/196; 546/284.1; 546/281.7; 549/404; 549/408; 549/437; 514/456; 514/462; 514/469; 514/278; 514/337
[58] Field of Search ............................ 548/311.4, 301.1; 514/397

[56] References Cited

U.S. PATENT DOCUMENTS

| | | | |
|---|---|---|---|
| 2,868,691 | 1/1959 | Porush et al. | 514/100 |
| 3,095,355 | 6/1963 | Abramson et al. | 514/100 |
| 4,775,679 | 10/1988 | Chang et al. | 514/397 |
| 4,857,516 | 8/1989 | Terao et al. | 514/100 |
| 4,978,761 | 12/1990 | Goto et al. | 549/462 |

FOREIGN PATENT DOCUMENTS

| | | |
|---|---|---|
| 0199235 | 10/1986 | European Pat. Off. . |
| 0483772 | 5/1992 | European Pat. Off. . |
| 6-41123 | 2/1994 | Japan . |
| 8705020 | 8/1987 | WIPO . |

OTHER PUBLICATIONS

Lau et al. CA 116:173926 1992.
Belanger et al. CA 116:106078 1991.
Chemical Abstracts, vol. 73, No. 15, 12 Oct. 1970, Columbus, Ohio, US; Abstract No. 77054k, M. Murakami et al, "5–Substituted methyl–6–chromanol derivatives as antioxidants", p. 353, col. 2, *abstract*, and JP–A–45 014 787 (Yamanouchi Pharmaceuticl Co., Ltd. 25 May 1970.
Journal Of Medicinal Chemistry, vol. 10, No. 4, 1967, Washington, US, pp. 657–660, W. A. Skinner et al, "Structure–Activity Relations in the Vitamin E Series. I. Effects of 5–Methyl Substitution on 6–Hydroxy-2,2,5,7,8–pentamethylchroman", p. 658, Example 18, Table I.
Bulletin Of The Chemical Society Of Japan, vol. 52, No. 4, 1979, Tokyo, JP, pp. 1143–1146, K. Murayama et al, "Synthesis of Methyl Substitute Chromanol. An Analogue of Vitamin K", p. 1145, col. 1, Example 6B.
Database WPI–Week 9401, Derwent Publications Ltd., London, GB; An 94–002287 & JP–A–5 310 724 (EISAI Co., Ltd.) 22 Nov. 1993–*Abstract*.

*Primary Examiner*—Jane Fan
*Attorney, Agent, or Firm*—Watson Cole Stevens Davis

[57] ABSTRACT

Fused phenol compounds of the formula (I):

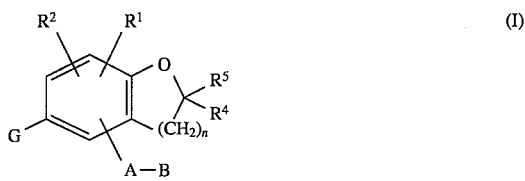

(wherein $R^1$ and $R^2$ each, independently, is H, halogen, trifluoromethyl, cyano, (substituted) alkyl, alkoxy, cycloalkyl, COOH, COOR$^6$ (in which R$^6$ is C1-6 alkyl), alkenyl or $R^1$ and $R^2$, taken together, is —CH=CH—CH=CH—, when $R^1$ and $R^2$ are ortho to each other; A is alkylene, alkenylene, oxyalkylene or

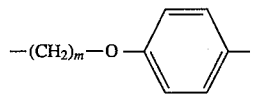

(in which m is 1–6); B is a monocyclic hetero ring containing a nitrogen atom; G is —OR$^{3A}$ or —NR$^{3B}$R$^{3C}$ (in which R$^{3A}$, R$^{3B}$ and R$^{3C}$ each, independently, is H, alkyl, acyl, or alkoxyalkyl); $R^4$ and $R^5$ each, independently, is H, alkyl, or $R^4$, $R^5$ together with the carbon atom to which they are attached represent C4–7 cycloalkyl; and n is 1–3; non-toxic salts thereof, non-toxic acid addition salts thereof, and hydrates thereof.

The compounds of the formula (I) have inhibitory activities on TXA$_2$ synthetase and on 5-lipoxygenase and/or a scavenging activity on active oxygen species, and are useful for the prevention and/or the treatment of thrombosis, arteriosclerosis, ischemic heart diseases or brain diseases, bronchial asthma, renal inflammation, rheumatism, arthritis, gout, psoriasis, ulcerative colitis, trichophytosis, cardiac infarction, allergic diseases, etc.

15 Claims, No Drawings

FUSED PHENOL DERIVATIVES

SUMMARY

This invention is related to fused phenol derivatives.

More particularly, this invention is related to:

(1) fused phenol derivatives of the formula (I):

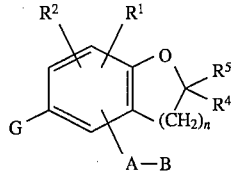

wherein all the symbols are the same meaning as hereafter defined, and non-toxic salts thereof and non-toxic acid addition salts thereof and hydrates thereof, (2) processes for the preparation thereof, and (3) pharmaceutical agents containing them as the active ingredient.

BACKGROUND OF THE INVENTION

Animal tissues have a metabolic system called the arachidonic acid cascade. Arachidonic acid, which is stored in the form of phospholipid, is released by the action of an esterase, phospholipase.

Arachidonic acid is converted into 5-hydroxyperoxy-6, 8, 11, 14-eicosatetraenoic acid (5-HPETE) by the addition of molecular oxygen by the action of 5-lipoxygenase. Part of the peroxy acid 5-HPETE is converted to form 5-hydroxy-6, 8, 11, 14-eicosatetraenoic acid (5-HETE). Further, 5-HPETE is converted into leukotriene $A_4$ ($LTA_4$) and leukotriene $B_4$ ($LTB_4$). Furthermore, $LTA_4$ is convened into leukotriene $C_4$ ($LTC_4$), leukotriene $D_4$ ($LTD_4$), and leukotriene $E_4$ ($LTE_4$).

On the other hand, arachidonic acid is convened into prostaglandin $G_2$ ($PGG_2$) by cyclooxygenase. $PGG_2$ is converted into prostaglandin $H_2$ ($PGH_2$) by PG hydroperoxytase. $PGH_2$ is convened into thromboxane $A_2$ ($TXA_2$) by thromboxane (TX) synthetase. It is known that $TXA_2$ thus obtained is very unstable, and therefore, immediately convened into thromboxane $B_2$ ($TXB_2$).

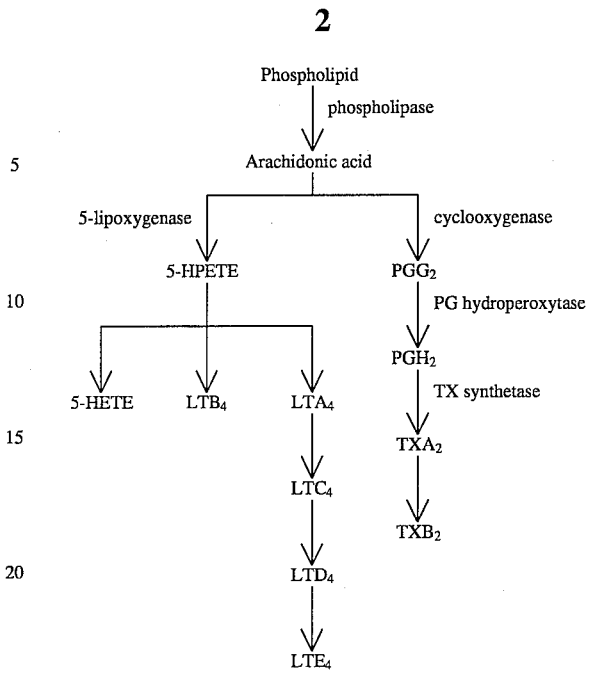

$LTB_4$ has migratory and adhesive activities on leukocyte, and degranulation activity on leukocyte. $LTC_4$, $LTD_4$ and $LTE_4$ have contractile activity on pulmonary and bronchial muscles, and artery.

It is known that $TXA_2$ has platelet aggregation activity, and contractile activity on vascular smooth muscle and on bronchial smooth muscle.

RELATED ARTS

Recently, energetic investigations relating to lipoxygenase, TX and active oxygen species have been carried out. It has become apparent that these are related to many kinds of disease. Therefore, investigations relating to inhibitors which inhibit their synthesis are considered to be important for the purpose of treatment of many diseases. In particular, studies on 5-lipoxygenase inhibitors, $TXA_2$ synthetase inhibitors and oxygen species scavengers have been reported.

For example, it is disclosed that the 3,4-dihydro-2H-benzopyran derivatives of the formula (X)

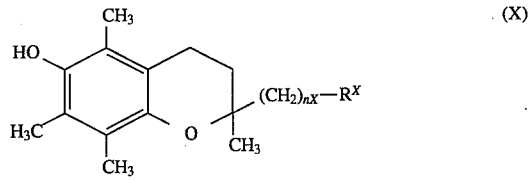

(wherein $n^x$ is 1–3, $R^x$ is a hetero ring containing nitrogen atom, optionally selected from

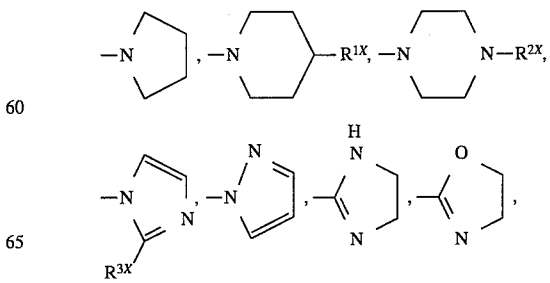

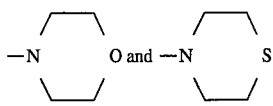

in which $R^{1x}$ and $R^{2x}$ each, independently, is hydrogen atom, alkyl which may have substituents, aralkyl, arylalkenyl, allyl or acyl, $R^{3x}$ is hydrogen atom or alkyl) have at least one of an inhibitory activity on 5-lipoxygenase, anti-allergy activity, anti-histamine activity, an inhibitory activity on lipid peroxidation and an inhibitory activity on platelet aggregation (see the specification of WO 87/05020).

Further, it is disclosed that the 2,3-dihydrobenzofuran derivatives of the formula (Y)

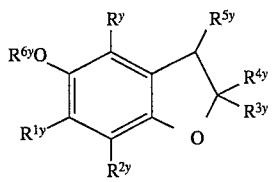

(wherein $R^Y$ is lower alkyl, $R^{6Y}$ is hydrogen atom or acyl, $R^{1Y}$ and $R^{2Y}$, which may be same or different, is lower alkyl which may have substituents, $R^{1Y}$ and $R^{2Y}$, taken together are butadienylene which may have substituents, $R^{3Y}$ and $R^{4Y}$ each, independently, represent hydrogen atom or alkyl which may have substituents, $R^{3Y}$ and $R^{4Y}$, taken together, are polymethylene, $R^{5Y}$ is lower alkyl which may have as substituents, an aromatic ring or hetero ring) have scavenging activity on active oxygen species, inhibitory activity on biosynthesis of $TXA_2$, and on 5-lipoxygenase or anti-allergic activity (see the specification of the U.S. Pat. No. 4,857,516 which is herein incorporated by reference).

Furthermore, it is disclosed that the 2,3-dihydrobenzofuran derivatives of the formula (Z)

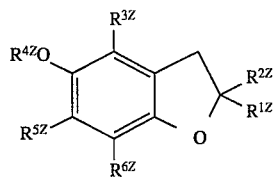

(wherein $R^{1Z}$ is a hydrogen atom or lower alkyl, $R^{2Z}$ is methyl substituted by carboxy, alkoxycarbonyl, cyano, halogen, aryl or hetero ring, or C2–15 hydrocarbon chain group not having lower allyl at the a-position thereof, which may be substituted by carboxy, alkoxycarbonyl, cyano, halogen, aryl or hetero ring, $R^{3Z}$ is lower alkyl, $R^{4Z}$ is hydrogen atom or acyl, $R^{5Z}$ and $R^{6Z}$, independently, is lower alkyl or lower alkoxy, and $R^{5Z}$ and $R^{6Z}$, taken together, are butadienylene) have an inhibitory activity on 5-lipoxygenase or 12-lipoxygenase (see the specification of the U.S. Pat. No. 4,978,761 which is herein incorporated by reference).

Furthermore, it is disclosed that the 2,3-dihydrobenzofuran derivatives of the formula (W)

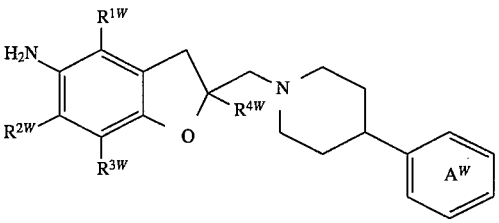

(wherein $R^{1W}$, $R^{2W}$, $R^{3W}$ and $R^{4W}$ each, independently, are lower alkyl, $A^W$ ring is a benzene ring substituted by at least one of lower alkyl, lower alkoxy or halogen atom) have inhibitory activity on formation of lipid peroxides and 5-lipoxygenase, inhibitory activity on $TXA_2$ synthetase, maintenance of prostaglandin $I_2$, inhibitory activity on $LTD_4$ receptor, and scavenging activity on active oxygen species (see the specification of the Japanese Patent Kokai No. 6-41123).

PURPOSE OF THE INVENTION

Energetic investigations have been carried out in order to discover new compounds having inhibitory activities on $TXA_2$ synthetase and on 5-lipoxygenase, and/or scavenging activity on active oxygen species. As a result, the present inventors have found that the purpose has been accomplished by a fused phenol derivatives of the formula (I) in which a monocyclic hetero ring represented by B, which is bound to a benzene ring via a group A.

COMPARISON WITH RELATED ART

The fused phenol derivatives of the present invention have never been known before, and therefore, are quite novel.

To summarize, $R^x$ in the formula (X) hereinbefore depicted can represent a variety of hetero rings containing a nitrogen atom, but the said group is necessarily bonded to the 2nd position of a benzopyran ring via an alkylene side chain. That is, a variety of hetero rings containing a nitrogen atom are never bonded directly or indirectly to a benzene ring.

Further, $R^{5Y}$ in the formula (Y) hereinbefore depicted can represent lower alkyl which may have as substituents, an aromatic ring or hetero ring, but the said group is necessarily bonded to the 3rd position of a 2,3-dihydrobenzofuran ring. That is, a hetero ring is never bonded directly or indirectly to a benzene ring.

Furthermore, $R^{2Z}$ in the formula (Z) hereinbefore depicted can represent methyl substituted by aryl or a hetero ring, or C2–15 hydrocarbon chain group not having lower alkyl at the a-position thereof, and which may be substituted by aryl or hetero ring, but the said group is necessarily bonded to the 2nd position of a 2,3-dihydrobenzofuran. Further, it is disclosed in detailed description of the specification of U.S. Pat. No. 4,978,761, that $R^{5Z}$ and $R^{6Z}$ may represent a lower alkyl substituted by e.g., 3-pyridyl, 1-imidazolyl, 5-thiazolyl etc. However, only compounds in which each of $R^{5Z}$ and $R^{6Z}$ is methyl are specifically disclosed. Namely, it can be said that there is no disclosure of the compounds in which each of $R^{5Z}$ and $R^{6Z}$ is a lower alkyl substituted by e.g., 3-pyridyl 1-imidazolyl, 5-thiazolyl etc.

Furthermore, the compounds of the formula (W) hereinbefore depicted, have the group of the formula

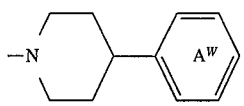

But the said group is necessarily bonded to the 2nd position of a 2,3-dihydrobenzofuran via methylene. That is, hetero ring containing a nitrogen atom is never bonded directly or indirectly to a benzene ring.

It is concluded from the four prior art references above mentioned that compounds which have a substituent containing an aromatic ring or a nitrogen containing hetero ring attached to an oxygen containing ring in a fused benzene ring system, have an inhibitory activity on 5-lipoxygenase and/or on $TXA_2$ synthetase and/or a scavenging activity on active oxygen species.

The compounds of the present invention are distinguished from those of the prior art by the attachment of various hetero rings containing nitrogen to the benzene ring in a ring system in which an oxygen containing ring is fused to a benzene ring.

From the above viewpoint, it can be said that the compounds of the present invention have a chemical structure quite different from the prior art compounds of formula (X), (Y), (Z) and (W).

DISCLOSURE OF THE INVENTION

The present invention is related to:
(1) fused phenol derivatives of the formula (I):

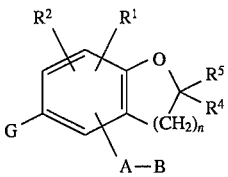

(I)

wherein $R^1$ and $R^2$ each, independently, is
1) hydrogen atom,
2) halogen atom,
3) trifluoromethyl,
4) cyano,
5) C1–10 alkyl,
6) C1–4 alkoxy,
7) C3–7 cycloalkyl,
8) C7–10 phenylalkyl,
9) C1–10 alkyl substituted by C1–4 alkoxy,
10) C1–4 alkyl substituted by C3–7 cycloalkyl,
11) C1–6 alkyl substituted by phenylthio,
12) C1–6 alkyl substituted by phenoxy,
13) —COOH,
14) —COOR$^6$ (in which R$^6$ is C1–6 alkyl),
15) C2–10 alkenyl or
(16) $R^1$ and $R^2$, taken together, represent —CH=CH—CH=CH—, when $R^1$ and $R^2$ are attached ortho to each other;

A is
1) C1–8 alkylene,
2) C2–8 alkenylene,
3) C1–6 oxyalkylene or

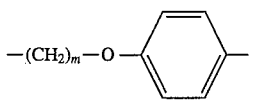

(in which m is 1–6, with the proviso that, B is bonded to the oxygen atom and phenylene group in C1–6 oxyalkylene and

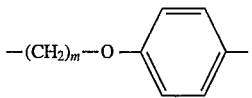

respectively); B is 5–7 membered monocyclic hetero ring containing one or two nitrogen atoms; G is —OR$^{3A}$ or —NR$^{3B}$R$^{3C}$ (in which R$^{3A}$, R$^{3B}$ and R$^{3C}$ each, independently, is a hydrogen atom, C1–4 alkyl, C7–10 phenylalkyl, C2–5 acyl, phenylcarbonyl, carbonyl substituted by C7–10 phenylalkyl or C2–4 alkoxyalkyl); $R^4$ and $R^5$ each, independently, is hydrogen atom, C1–8 alkyl, C7–10 phenylalkyl or $R^4$ and $R^5$ together with the carbon atom to which they are attached represent C4–7 cycloalkyl; and n is 1–3; and non-toxic salts thereof and non-toxic acid addition salts thereof and hydrates thereof;
(2) processes for the preparation thereof and
(3) pharmaceutical agents containing them as active ingredient.

Throughout the specification including claims, it may be easily understood by those skilled in the art, that all isomers are included in the present invention. For example, the alkyl, alkoxy, alkylene, alkenyl and alkenylene groups include straight-chain and also branched-chain ones. Double bond in alkenylene includes E, Z and EZ mixtures. Accordingly, all isomers produced by the existence of asymmetric carbon atoms are included in the present invention when e.g., branched-chain alkyl etc. exist.

In this specification, wave length means EZ mixture on double bond in alkenylene.

In the formula (I), C1–10 alkyl group represented by $R^1$ and $R^2$ means methyl, ethyl, propyl, butyl, pentyl, hexyl, heptyl, octyl, nonyl, decyl and the isomers thereof. C1–4 alkoxy group means methoxy, ethoxy, propoxy, butoxy and the isomers thereof. C3–7 cycloalkyl group means cyclopropyl cyclobutyl, cyclopentyl, cyclohexyl and cycloheptyl. C1–10 alkyl substituted by C1–4 alkoxy means methyl, ethyl, propyl, butyl, pentyl, hexyl, heptyl, octyl, nonyl, decyl and the isomers thereof, which are substituted by a group selected from methoxy, ethoxy, propoxy, butoxy and the isomers thereof. C1–4 alkyl substituted by C3–7 cycloalkyl means methyl, ethyl, propyl, butyl and the isomers thereof, which are substituted by a group selected from cyclopropyl, cyclobutyl, cyclopentyl, cyclohexyl and cycloheptyl. C1–6 alkyl substituted by a phenylthio group means methyl, ethyl, propyl, butyl, pentyl, hexyl and the isomers thereof, which are substituted by a phenylthio group. C1–6 alkyl substituted by a phenoxy group means methyl, ethyl, propyl, butyl, pentyl, hexyl and the isomers thereof, which are substituted by a phenoxy group. Halogen atom means fluorine, chlorine, bromine and iodine atoms. C2–10 alkenyl group includes ethenyl, propenyl, butenyl, pentenyl, hexenyl, heptenyl, octenyl, nonenyl, decenyl, butadienyl, pentadienyl, hexadienyl, heptadienyl, octadienyl, nonadienyl, decadienyl, hexatrienyl, heptatrienyl, octatrienyl, nonatrienyl, decatrienyl and the isomers thereof.

In the formula (I), C1–6 alkyl represented by R$^6$ in R$^1$ and $R^2$ means methyl, ethyl, propyl, butyl, pentyl, hexyl and the isomer thereof.

In the formula (I), C7–10 phenylalkyl represented by $R^1$, $R^2$, $R^{3A}$, $R^{3B}$ and $R^{3C}$ in G group, $R^4$ and $R^5$ means methyl, ethyl, propyl, butyl and the isomers thereof, which are substituted by a phenyl group.

In the formula (I), C1–4 alkyl represented by $R^{3A}$, $R^{3B}$ and $R^{3C}$ in G group means methyl, ethyl, propyl, butyl and the isomers thereof. C2–5 acyl group means acetyl, propionyl, butyryl, valeryl and the isomers thereof. C2–4 alkoxyalkyl group means methoxymethyl, ethoxymethyl, propoxymethyl, methoxyethyl, ethoxyethyl, methoxypropyl and the isomers thereof.

In the formula (I), C1–8 alkyl group represented by $R^4$ and $R^5$ means methyl, ethyl, propyl, butyl, pentyl, hexyl, heptyl, octyl and the isomers thereof.

In the formula (I), C4–7 cycloalkyl group represented by $R^4$ and $R^5$ together with the carbon atom to which they are attached means cyclobutyl, cyclopentyl, cyclohexyl and cycloheptyl.

In the formula (I), C1–8 alkylene group represented by A means methylene, ethylene, trimethylene, tetramethylene, pentamethylene, hexamethylene, heptamethylene, octamethylene and the isomers thereof. C2–8 alkenylene group means vinylene, propenylene, butenylene, pentenylene, hexenylene, heptenylene, octenylene, butadienylene, pentadienylene, hexadienylene, heptadienylene, octadienylene, hexatrienylene, heptatrienylene, octatrienylene and the isomers thereof. C1–6 oxyalkylene group means oxymethylene, oxyethylene, oxytrimethylene, oxytetramethylene, oxypentamethylene, oxyhexamethylene and the isomers thereof.

In the formula (I), 5–7 membered monocyclic hetero ring containing one or two nitrogen atom represented by B includes pyrrole, pyrroline, pyrrolidine, imidazole, imidazoline, imidazolidine, pyrazole, pyrazoline, pyrazolidine, pyridine, piperidine, pyridazine, pyrimidine, pyrazine, piperazine and azepine etc.

$R^1$ and $R^2$ each, independently, is preferably C1–10 alkyl or C3–7 cycloalkyl group. $R^{3A}$ in G group is preferably hydrogen atom or C2–5 acyl group. $R^{3B}$ in G group is preferably hydrogen atom. $R^{3C}$ in G group is preferably hydrogen atom or C2–5 acyl group. $R^4$ and $R^5$ each, independently, is preferably C1–8 alkyl group. A is preferably C1–8 alkylene group. B is preferably imidazole or pyridine group.

Acid Addition Salts

The compounds of the formula (I), of the present invention may be converted into the corresponding acid addition salts by methods known per se. Non toxic and water-soluble salts are preferable. Suitable acid addition salts include the salts with inorganic acids such as hydrochloric acid, hydrobromic acid, sulfuric acid, phosphoric acid and nitric acid, and the salts with organic acids such as acetic acid, trifluoroacetic acid, lactic acid, tartaric acid, oxalic acid, fumaric acid, maleic acid, benzenesulfonic acid, toluenesulfonic acid, isethionic acid, glucuronic acid and gluconic acid.

Salt

The compounds of the formula (I) of the present invention, when at least one group of $R^1$ and $R^2$ represent COOH, may be converted into the corresponding salts by methods known per se. Non-toxic and water-soluble salts are preferable. Suitable salts, for example, are salts of alkali metal (e.g., potassium, sodium etc.), salts of alkaline earth metal (e.g., calcium, magnesium etc.), ammonium salts, salts of pharmaceutically-acceptable organic amine (e.g., tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine etc.).

Preferred compounds of the present invention are listed as follows: fused phenol derivatives of the formula I (1)

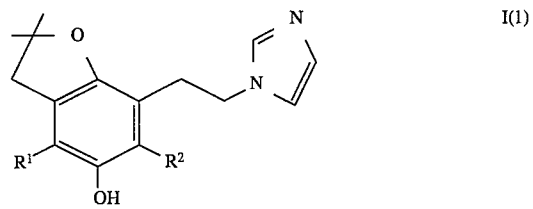

(wherein $R^1$ and $R^2$ each, independently, is the same as hereinbefore defined), the formula I (2)

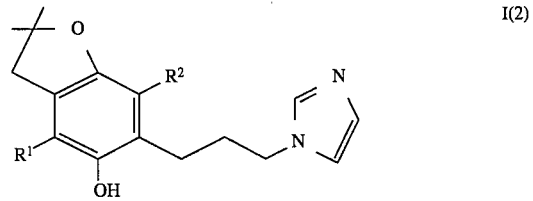

(wherein $R^1$ and $R^2$ each, independently, is the same meaning as hereinbefore defined), the formula I (3)

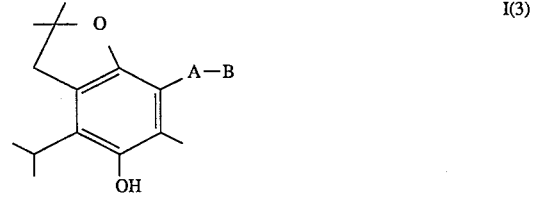

(wherein A and B respectively, are the same meaning as hereinbefore defined), the formula I (4)

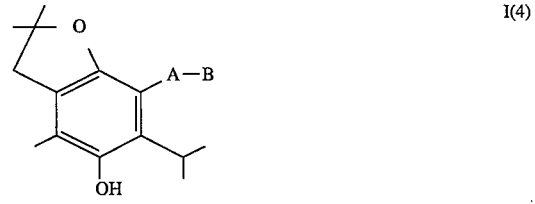

(wherein A and B, respectively, are the same meaning as hereinbefore defined), the formula I (5)

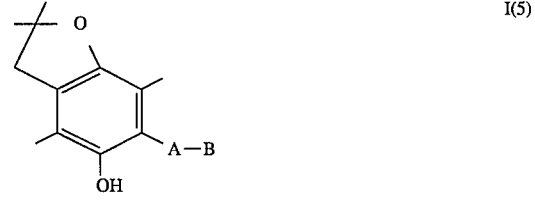

(wherein A and B, respectively, are the same meaning as hereinbefore defined), the formula I (6)

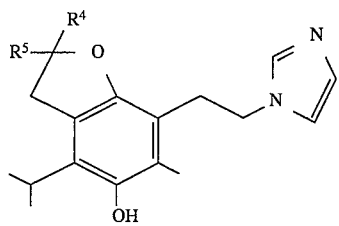
I(6)

(wherein $R^4$ and $R^5$ each, independently, is the same meaning as hereinbefore defined), the formula I (7)

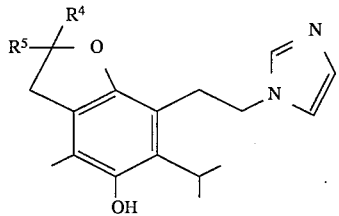
I(7)

(wherein $R^4$ and $R^5$ each, independently, is the same meaning as hereinbefore defined), the formula I (8)

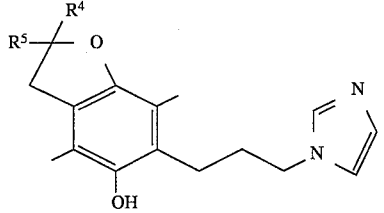
I(8)

(wherein $R^4$ and $R^5$ each, independently, is the same meaning as hereinbefore defined); the formula I (9)

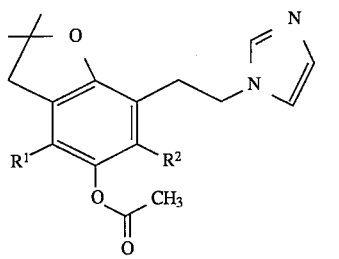
I(9)

(wherein $R^1$ and $R^2$ each, independently, is the same meaning as hereinbefore defined), the formula I(10)

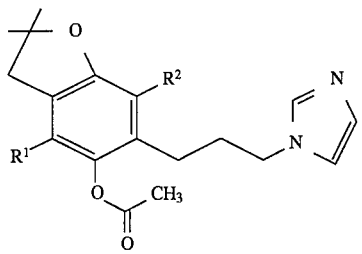
I(10)

(wherein $R^1$ and $R^2$ each, independently, is the same meaning as hereinbefore defined), the formula I (11)

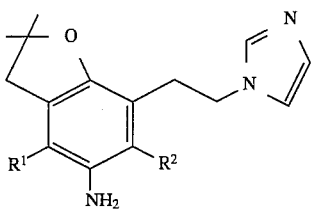
I(11)

(wherein $R^1$ and $R^2$ each, independently, is the same meaning as hereinbefore defined), the formula I(12)

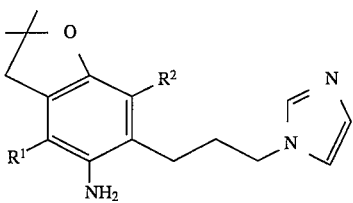
I(12)

(wherein $R^1$ and $R^2$ each, independently, is the same meaning as hereinbefore defined), the formula I(13)

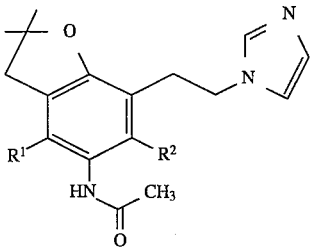
I(13)

(wherein $R^1$ and $R^2$ each, independently, is the same meaning as hereinbefore defined), the formula I (14)

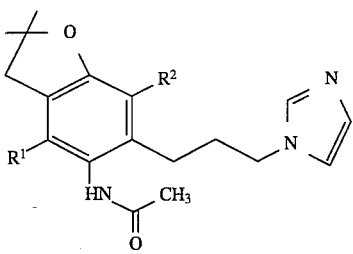
I(14)

(wherein $R^1$ and $R^2$ each, independently, is as hereinbefore defined), non-toxic salts thereof, acid-addition salts thereof, and hydrates thereof.

Examples of representative compounds of the present invention are listed as follows:

TABLE 1

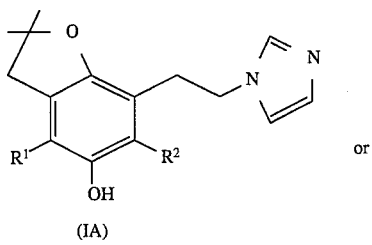

(IA)

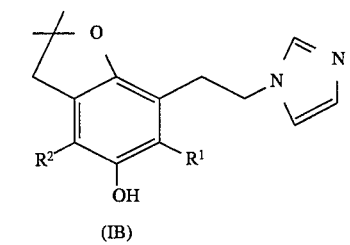

(IB)

| No. | | $R^1$ | $R^2$ |
|---|---|---|---|
| 1 | (IA) or (IB) | cyclopropyl | methyl |
| 2 | (IA) or (IB) | cyclopentyl | methyl |
| 3 | (IA) or (IB) | chlorine | methyl |
| 4 | (IA) or (IB) | trifluoromethyl | methyl |
| 5 | (IA) or (IB) | phenoxypropyl | methyl |
| 6 | (IA) or (IB) | chlorine | isopropyl |
| 7 | (IA) or (IB) | trifluoromethyl | isopropyl |
| 8 | (IA) or (IB) | phenoxypropyl | isopropyl |
| 9 | (IA) or (IB) | hexyl | hexyl |
| 10 | (IA) or (IB) | isopropoxy | methyl |

TABLE 2

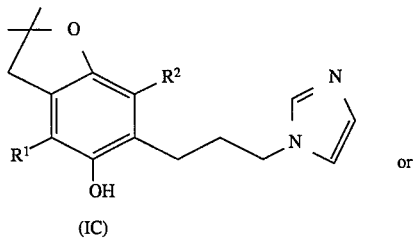

(IC)

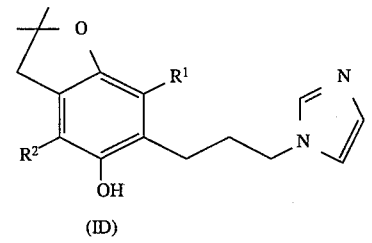

(ID)

| No. | | $R^1$ | $R^2$ |
|---|---|---|---|
| 1 | (IC) or (ID) | cyclopropyl | methyl |
| 2 | (IC) or (ID) | cyclopentyl | methyl |
| 3 | (IC) or (ID) | chlorine | methyl |
| 4 | (IC) or (ID) | trifluoromethyl | methyl |
| 5 | (IC) or (ID) | phenoxypropyl | methyl |

TABLE 2-continued

| 6 | (IC) or (ID) | chlorine | isopropyl |
|---|---|---|---|
| 7 | (IC) or (ID) | trifluoromethyl | isopropyl |
| 8 | (IC) or (ID) | phenoxypropyl | isopropyl |
| 9 | (IC) or (ID) | hexyl | hexyl |
| 10 | (IC) or (ID) | isopropoxy | methyl |

TABLE 3

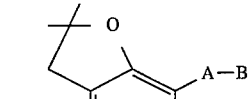

(IE)

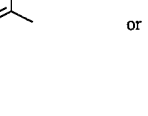

(IF)

| No. | | A | B |
|---|---|---|---|
| 1 | (IE) or (IF) | hexamethylene | 1-imidazolyl |
| 2 | (IE) or (IF) | octamethylene | 1-imidazolyl |
| 3 | (IE) or (IF) | trimethylene | 3-pyridyl |
| 4 | (IE) or (IF) | hexamethylene | 3-pyridyl |
| 5 | (IE) or (IF) | ethylene | 1-pyrrolyl |
| 6 | (IE) or (IF) | ethylene | 1-pyrazolyl |
| 7 | (IE) or (IF) | ethylene | 3-pyridazinyl |
| 8 | (IE) or (IF) | ethylene | 2-pyrimidinyl |
| 9 | (IE) or (IF) | ethylene | 2-pyrazinyl |
| 10 | (IE) or (IF) | ethylene | 1-1H-azepinyl |

TABLE 4

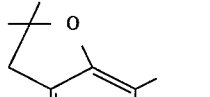

(IG)

| No. | | A | B |
|---|---|---|---|
| 1 | (IG) | hexamethylene | 1-imidazolyl |
| 2 | (IG) | octamethylene | 1-imidazolyl |
| 3 | (IG) | trimethylene | 3-pyridyl |
| 4 | (IG) | hexamethylene | 3-pyridyl |
| 5 | (IG) | ethylene | 1-pyrrolyl |
| 6 | (IG) | ethylene | 1-pyrazolyl |
| 7 | (IG) | ethylene | 3-pyridazinyl |
| 8 | (IG) | ethylene | 2-pyrimidinyl |
| 9 | (IG) | ethylene | 2-pyrazinyl |

TABLE 4-continued

| | | | |
|---|---|---|---|
| 10 | (IG) | ethylene | 1-1H-azepinyl |

TABLE 5

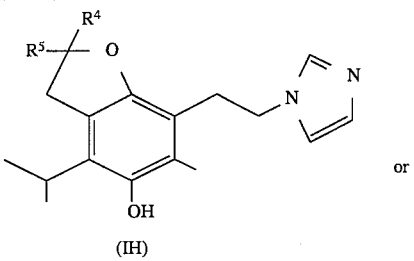

| No. | | $R^4$ | $R^5$ |
|---|---|---|---|
| 1 | (IH) or (IJ) | hydrogen | methyl |
| 2 | (IH) or (IJ) | hydrogen | phenylmethyl |
| 3 | (IH) or (IJ) | hydrogen | phenylethyl |
| 4 | (IH) or (IJ) | methyl | phenylmethyl |
| 5 | (IH) or (IJ) | hydrogen | hexyl |
| 6 | (IH) or (IJ) | hexyl | hexyl |

TABLE 6

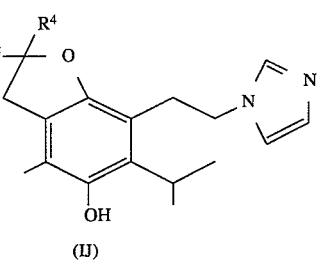

| No. | | $R^4$ | $R^5$ |
|---|---|---|---|
| 1 | (IK) | hydrogen | methyl |
| 2 | (IK) | hydrogen | phenylmethyl |
| 3 | (IK) | hydrogen | phenylethyl |

TABLE 6-continued

| | | | |
|---|---|---|---|
| 4 | (IK) | methyl | phenylmethyl |
| 5 | (IK) | hydrogen | hexyl |
| 6 | (IK) | hexyl | hexyl |

TABLE 7

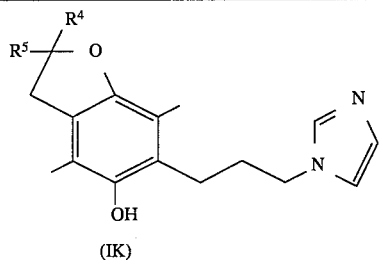

| No. | | $R^1$ | $R^2$ |
|---|---|---|---|
| 1 | (IL) or (IM) | cyclopropyl | methyl |
| 2 | (IL) or (IM) | cyclopentyl | methyl |
| 3 | (IL) or (IM) | chlorine | methyl |
| 4 | (IL) or (IM) | trifluoromethyl | methyl |
| 5 | (IL) or (IM) | phenoxypropyl | methyl |
| 6 | (IL) or (IM) | chlorine | isopropyl |
| 7 | (IL) or (IM) | trifluoromethyl | isopropyl |
| 8 | (IL) or (IM) | phenoxypropyl | isopropyl |
| 9 | (IL) or (IM) | hexyl | hexyl |
| 10 | (IL) or (IM) | isopropoxy | methyl |
| 11 | (IL) or (IM) | methyl | methyl |
| 12 | (IL) or (IM) | ethyl | methyl |
| 13 | (IL) or (IM) | isopropyl | methyl |
| 14 | (IL) or (IM) | isobutyl | methyl |
| 15 | (IL) or (IM) | ethyl | ethyl |
| 16 | (IL) or (IM) | isopropyl | isopropyl |

TABLE 8

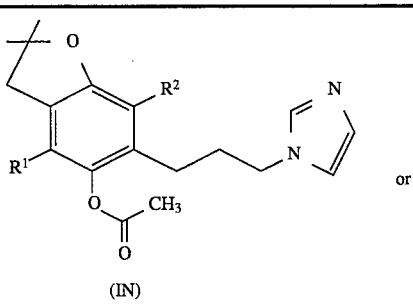

(IN)

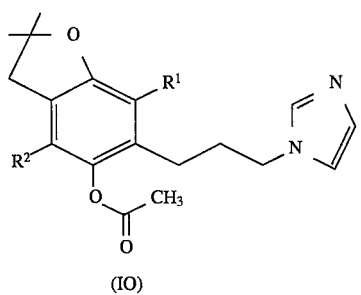

(IO)

| No. | | R¹ | R² |
|---|---|---|---|
| 1 | (IN) or (IO) | cyclopropyl | methyl |
| 2 | (IN) or (IO) | cyclopentyl | methyl |
| 3 | (IN) or (IO) | chlorine | methyl |
| 4 | (IN) or (IO) | trifluoromethyl | methyl |
| 5 | (IN) or (IO) | phenoxypropyl | methyl |
| 6 | (IN) or (IO) | chlorine | isopropyl |
| 7 | (IN) or (IO) | trifluoromethyl | isopropyl |
| 8 | (IN) or (IO) | phenoxypropyl | isopropyl |
| 9 | (IN) or (IO) | hexyl | hexyl |
| 10 | (IN) or (IO) | isopropoxy | methyl |
| 11 | (IN) or (IO) | methyl | methyl |
| 12 | (IN) or (IO) | ethyl | methyl |
| 13 | (IN) or (IO) | isopropyl | methyl |
| 14 | (IN) or (IO) | isobutyl | methyl |
| 15 | (IN) or (IO) | ethyl | ethyl |
| 16 | (IN) or (IO) | isopropyl | isopropyl |

TABLE 9

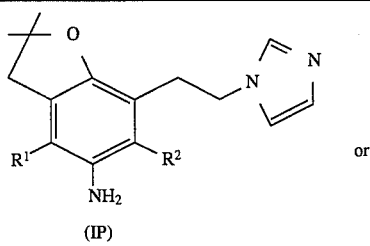

(IP)

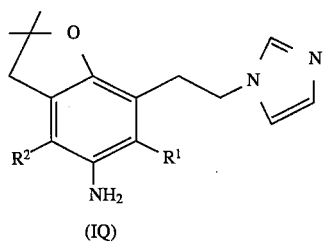

(IQ)

| No. | | R¹ | R² |
|---|---|---|---|
| 1 | (IP) or (IQ) | cyclopropyl | methyl |

TABLE 9-continued

| | | | |
|---|---|---|---|
| 2 | (IP) or (IQ) | cyclopentyl | methyl |
| 3 | (IP) or (IQ) | chlorine | methyl |
| 4 | (IP) or (IQ) | trifluoromethyl | methyl |
| 5 | (IP) or (IQ) | phenoxypropyl | methyl |
| 6 | (IP) or (IQ) | chlorine | isopropyl |
| 7 | (IP) or (IQ) | trifluoromethyl | isopropyl |
| 8 | (IP) or (IQ) | phenoxypropyl | isopropyl |
| 9 | (IP) or (IQ) | hexyl | hexyl |
| 10 | (IP) or (IQ) | isopropoxy | methyl |
| 11 | (IP) or (IQ) | methyl | methyl |
| 12 | (IP) or (IQ) | ethyl | methyl |
| 13 | (IP) or (IQ) | isopropyl | methyl |
| 14 | (IP) or (IQ) | isobutyl | methyl |
| 15 | (IP) or (IQ) | ethyl | ethyl |
| 16 | (IP) or (IQ) | isopropyl | isopropyl |

TABLE 10

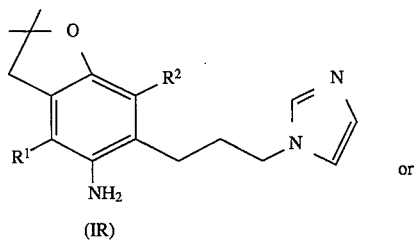

(IR)

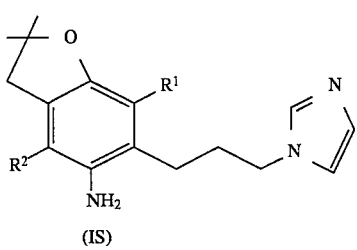

(IS)

| No. | | R¹ | R² |
|---|---|---|---|
| 1 | (IR) or (IS) | cyclopropyl | methyl |
| 2 | (IR) or (IS) | cyclopentyl | methyl |
| 3 | (IR) or (IS) | chlorine | methyl |
| 4 | (IR) or (IS) | trifluoromethyl | methyl |
| 5 | (IR) or (IS) | phenoxypropyl | methyl |
| 6 | (IR) or (IS) | chlorine | isopropyl |
| 7 | (IR) or (IS) | trifluoromethyl | isopropyl |
| 8 | (IR) or (IS) | phenoxypropyl | isopropyl |
| 9 | (IR) or (IS) | hexyl | hexyl |
| 10 | (IR) or (IS) | isopropoxy | methyl |
| 11 | (IR) or (IS) | methyl | methyl |
| 12 | (IR) or (IS) | ethyl | methyl |
| 13 | (IR) or (IS) | isopropyl | methyl |
| 14 | (IR) or (IS) | isobutyl | methyl |
| 15 | (IR) or (IS) | ethyl | ethyl |
| 16 | (IR) or (IS) | isopropyl | isopropyl |

TABLE 11

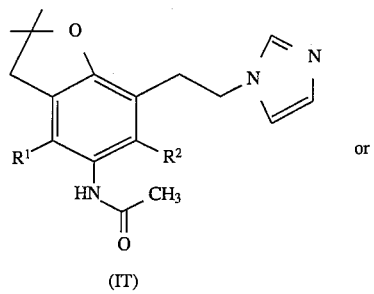

(IT)

(IU)

| No. | | R¹ | R² |
|---|---|---|---|
| 1 | (IT) or (IU) | cyclopropyl | methyl |
| 2 | (IT) or (IU) | cyclopentyl | methyl |
| 3 | (IT) or (IU) | chlorine | methyl |
| 4 | (IT) or (IU) | trifluoromethyl | methyl |
| 5 | (IT) or (IU) | phenoxypropyl | methyl |
| 6 | (IT) or (IU) | chlorine | isopropyl |
| 7 | (IT) or (IU) | trifluoromethyl | isopropyl |
| 8 | (IT) or (IU) | phenoxypropyl | isopropyl |
| 9 | (IT) or (IU) | hexyl | hexyl |
| 10 | (IT) or (IU) | isopropoxy | methyl |
| 11 | (IT) or (IU) | methyl | methyl |
| 12 | (IT) or (IU) | ethyl | methyl |
| 13 | (IT) or (IU) | isopropyl | methyl |
| 14 | (IT) or (IU) | isobutyl | methyl |
| 15 | (IT) or (IU) | ethyl | ethyl |
| 16 | (IT) or (IU) | isopropyl | isopropyl |

TABLE 12

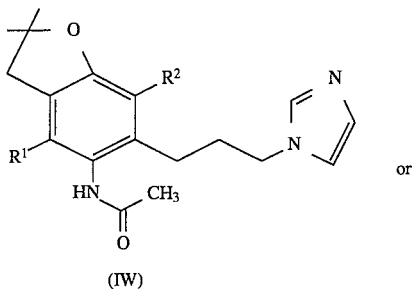

(IW)

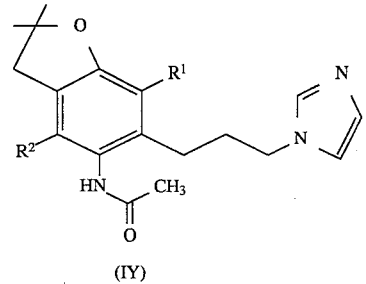

(IY)

| No. | | R¹ | R² |
|---|---|---|---|
| 1 | (IW) or (IY) | cyclopropyl | methyl |
| 2 | (IW) or (IY) | cyclopentyl | methyl |
| 3 | (IW) or (IY) | chlorine | methyl |
| 4 | (IW) or (IY) | trifluoromethyl | methyl |
| 5 | (IW) or (IY) | phenoxypropyl | methyl |
| 6 | (IW) or (IY) | chlorine | isopropyl |
| 7 | (IW) or (IY) | trifluoromethyl | isopropyl |
| 8 | (IW) or (IY) | phenoxypropyl | isopropyl |
| 9 | (IW) or (IY) | hexyl | hexyl |
| 10 | (IW) or (IY) | isopropoxy | methyl |
| 11 | (IW) or (IY) | methyl | methyl |
| 12 | (IW) or (IY) | ethyl | methyl |
| 13 | (IW) or (IY) | isopropyl | methyl |
| 14 | (IW) or (IY) | isobutyl | methyl |
| 15 | (IW) or (IY) | ettiyl | ethyl |
| 16 | (IW) or (IY) | isopropyl | isopropyl | non toxic salts thereof, acid-addition salts thereof, hydrates thereof and further the compounds prepared in Examples hereinafter described.

Processes for the Preparation of the Compounds of the Present Invention

In the compounds of the formula (I), of the present invention, the compound of the formula (I-1)

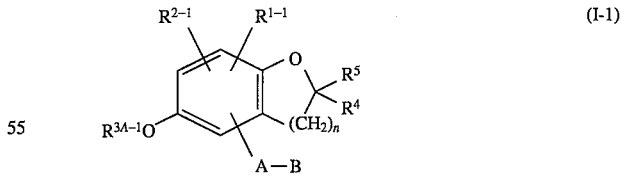

(I-1)

wherein $R^{1-1}$ and $R^{2-1}$ are the same meaning as hereinbefore defined for $R^1$ and $R^2$, provided that both of $R^1$ and $R^2$ do not represent COOH groups, $R^{3A-1}$ is C1–4 alkyl, C2–4 alkoxyalkyl or C7–10 phenylalkyl, and the other symbols are the same meaning as hereinbefore defined may be prepared by methods (a) to (d) as follows.

(a) in the compounds of formula (I-1), of the present invention, those in which A represents C1–8 alkylene or C2–8 alkenylene and A is bonded directly to a nitrogen atom in the hetero ring represented by B, i.e., the compounds of the formula (I-a)

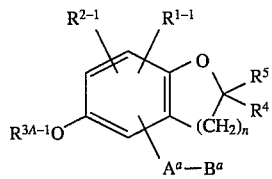

wherein $A^a$ is C1–8 alkylene or C2–8 alkenylene, $B^a$ is the same meaning as hereinbefore defined for B, the other symbols are the same meaning as hereinbefore defined, provided that $A^a$ is bonded directly to a nitrogen atom in hetero ring represented by $B^a$ may be prepared by reacting a compound of the formula (II-a)

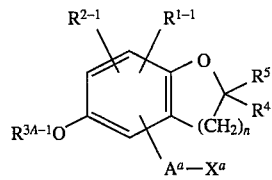

wherein $X^a$ is a leaving group known per se (e.g., chlorine, bromine or iodine atom, mesyl or tosyl group etc.), and the other symbols are the same meaning as hereinbefore defined with a compound of the formula (III-a)

 (III-a)

wherein $B^a$ is the same meaning as hereinbefore defined.

This reaction may be carried out, for example, in an organic solvent (e.g., benzene, toluene, etc.) at a temperature of from 80° C. to 150° C.

(b) In the compounds of formula (I-1), of the present invention, those in which A represents C2–8 alkylene or C2–8 alkenylene and A is bonded directly to a carbon atom in the hetero ring represented by B, i.e., the compounds of the formula (I-b)

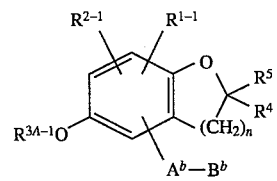

wherein $A^b$ is C2–8 alkylene or C2–8 alkenylene, $B^b$ is the same meaning as hereinbefore defined for B, and the other symbols are the same meaning as hereinbefore defined, provided that $A^b$ is bonded directly to a carbon atom in the hetero ring represented by $B^b$ may be prepared by the Wittig reaction of a compound of the formula (II-b)

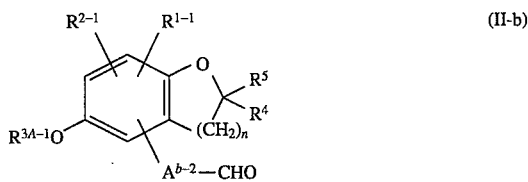

where $A^{b-2}$ is bond, C1–6 alkylene or C2–6 alkenylene, and the other symbols are the same meaning as hereinbefore defined with a compound of the formula (III-b)

wherein Y is halogen atom, $B^{b-3}$ is the same meaning as hereinbefore defined for $B^b$, provided that when free NH groups exist in $B^{b-3}$, the NH group should be protected by a protecting group usually known (e.g., triphenylmethyl group, etc.), followed, if desired, by hydrogenation of alkenylene to alkylene following by, if necessary, elimination of the NH protecting group.

The Wittig reaction is known per se, and may be carried out, for example, in an anhydrous inert organic solvent (e.g., tetrahydrofuran, benzene, hexane, etc.), in the presence of base (e.g., sodium hydride, n-butyllithium, etc.) under an atmosphere of inert gas (e.g., argon, etc.), at a temperature of from −78° C. to room temperature.

The hydrogenation is known per se, and may be carried out, for example, in an inert solvent [ether (e.g., tetrahydrofuran, dioxane, diethoxyethane, diethyl ether, etc.), alcohol (e.g., methanol, ethanol, etc.), benzene analogues (e.g., benzene, toluene, etc.), ketone (e.g., acetone, methyl ethyl ketone, etc.), nitrile (e.g., acetonitrile, etc.), amide (e.g., dimethylformamide etc.), water, ethyl acetate, acetic acid of the mixture of two or more of them, etc.], in the presence of a catalyst of hydrogenation (e.g., palladium on activated carbon, palladium black, palladium, palladium hydroxide on carbon, platinum oxide, nickel, Raney nickel (registered trade mark) etc.), in the presence of absence of an inorganic acid (e.g., hydrochloric acid, sulfuric acid, hypochlorous acid, boric acid, tetrafluoroboric acid, etc.) or an organic acid (e.g., acetic acid, p-toluenesulfonic acid, oxalic acid, trifluoroacetic acid, formic acid, etc.), at ordinary or increased pressure under an atmosphere of hydrogen, at a temperature of from 0° C. to 200° C. When using an acid, its salt may be used at the same time.

The elimination of an NH protecting group may be carried out by methods known per se, and depends on the protecting group. For example, when the protecting group is a triphenylmethyl group, the reaction may be carried out, in a water-miscible organic solvent (e.g., methanol, tetrahydrofuran, dioxane, acetone, etc.) in the presence of aqueous solution of organic acid (e.g., acetic acid, trifluoroacetic acid, etc.) or inorganic acid (hydrochloric acid, sulfuric acid, etc.) or a mixture of them, at a temperature of from 0° C. to 100° C.

(c) In the compounds of the formula (I-1), of the present invention, those in which A represents methylene and A is bonded directly to a carbon atom in the hetero ring represented by B, i.e., the compounds of the formula (I-c)

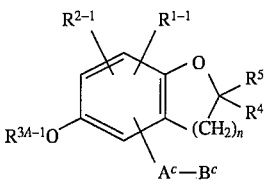 (I-c)

wherein $A^c$ is methylene, $B^c$ is the same meaning as hereinbefore defined for B, and the other symbols are the same meaning as hereinbefore defined, provide that $A^c$ is bonded directly to a carbon atom in the hetero ring represented by $B^c$ may be prepared by reacting a compound of the formula (II-c)

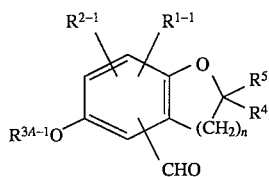 (II-c)

wherein all the symbols are the same meaning as hereinbefore defined with a compound of the formula (III-c)

$B^{c-3}$ Li  (III-c)

wherein $B^{c-3}$ is the same meaning as hereinbefore defined for $B^c$, provided that when free NH groups exist in $B^{c-3}$, the NH group should be protected by a protecting group usually known (e.g., triphenylmethyl group, etc.), followed by elimination of the hydroxy group produced by the reaction with an alkyllithium, and then, if necessary, elimination reaction of the NH protecting group.

This reaction with alkyllithium is known per se, and may be carried out, for example, by reacting a halide compound with alkyllithium (e.g., n-butyllithium, etc.) in an inert organic solvent (e.g., diethyl ether, tetrahydrofuran, etc.) under an atmosphere of an inert gas (e.g., argon, nitrogen, etc.), at a temperature of from −78° C. to −20° C., and then reacting thus obtained lithium compound, with the aldehyde of the formula (II-c) at a temperature of from −78° C. to −20° C.

The elimination of a hydroxy group is known per se, and may be carried out, for example, in an inert organic solvent (e.g., chloroform, dichloromethane, etc.) in the presence of a trialkylsilane (e.g., triethylsilane, triphenylsilane, etc.) and an acid (e.g., acetic acid, trifluoroacetic acid, trifluoroborane, etc.) under an atmosphere of an inert gas (e.g., argon, nitrogen, etc.) at a temperature of from 0° C. to room temperature.

The elimination of an NH protecting group may be carried out by the same method as hereinbefore described.

(d) In the compounds of the formula (I-1), of the present invention, those in which A represents C1–6 oxyalkylene or

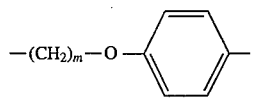

(in which m is the same meaning as hereinbefore defined), i.e., the compounds of formula (I-d)

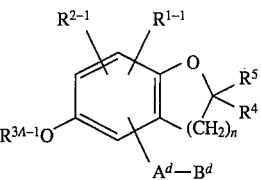 (I-d)

wherein $A^d$ is C1–6 oxyalkylene or

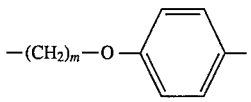

(in which m is the same meaning as hereinbefore defined), $B^d$ is the same meaning as hereinbefore defined for B, and the other symbols are the same meaning as hereinbefore defined may be prepared by reacting a compound of the formula (II-d)

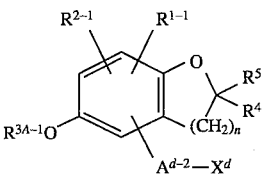 (II-d)

wherein $X^d$ is a leaving group, for example as hereinbefore described, $A^{d-2}$ is C1–6 alkylene, and the other symbols are the same meaning as hereinbefore defined with a compound of the formula (III-d-1)

HO—$B^d$  (III-d-1)

wherein $B^d$ is the same meaning as hereinbefore defined or a compound of the formula (III-d-2)

 (III-d-2)

wherein $B^d$ is the same meaning as hereinbefore defined.

This reaction may be carried out, for example, in an inert organic solvent (e.g., dimethylformamide, acetonitrile, acetone, etc.) in the presence of base (e.g., potassium carbonate, sodium hydride, etc.) under an atmosphere of an inert gas (e.g. argon, nitrogen, etc.) at a temperature of from 0° C. to 100° C.

In the compounds of the formula (I), of the present invention, the compound of the formula (I-2)

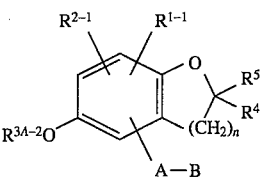 (I-2)

wherein R3A-2 is hydrogen atom, and the other symbols are the same meaning as hereinbefore defined may be prepared by subjecting to elimination the hydroxy protecting group by using an acid or to hydrogenation, of a compound of the formula (I-1), i.e., a compound of the formula (i–j)

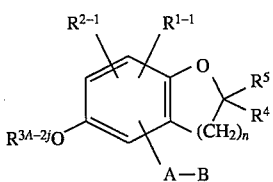

wherein $R^{3a-2j}$ is C2–4 alkoxyallyl or $-CH_2C_6H_5$ group, the other symbols are the same meaning as hereinbefore defined.

The elimination reaction by using an acid is known per se, and may be carried out, for example, in an organic solvent (e.g., methanol, tetrahydrofuran, dioxane, ethyl acetate, etc.) in the presence of organic acid (e.g., acetic acid, trifluoroacetic acid, etc.) or inorganic acid (e.g., hydrochloric acid, sulfuric acid etc.) or an aqueous solution of them or a mixture of them, at a temperature of from 0° C. to 100° C.

Hydrogenation may be carried out by the same method as hereinbefore described.

In the compounds of the formula (I), of the present invention, the compounds of the formula (I-3)

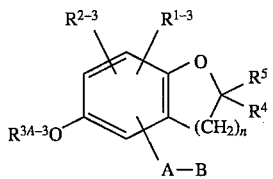

wherein $R^{1-3}$ and $R^{2-3}$ are the same meaning as hereinbefore defined for $R^1$ and $R^2$, provided that one of $R^{1-3}$ and $R^{2-3}$ represents a COOH group and the other group represents neither COOH nor $COOR^6$, $R^{3A-3}$ is hydrogen atom, C1–4 alkyl, C7–10 phenylalkyl or C2–4 alkoxyalkyl, and the other symbols are the same meaning as hereinbefore defined may be prepared by hydrolysis of a compound of the formula (I-1) or (I-2), having one $COOR^6$ group, i.e., a compound of the formula (I-e)

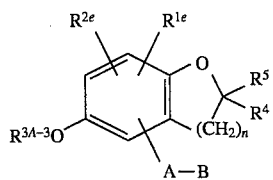

wherein $R^{1e}$ and $R^{2e}$ are the same meaning as hereinbefore defined for $R^1$ and $R^2$, provided that one of $R^{1e}$ and $R^{2e}$ represents $COOR^6$, and the other group represents neither COOH nor $COOR^6$, and the other symbols are the same meaning as hereinbefore defined.

Hydrolysis of an ester bond is known per se, and may be carried out, for example by hydrolysis in alkaline conditions, in an appropriate organic solvent (e.g., methanol, etc.), using a hydroxide or a carbonate of an alkali metals or alkaine earth metals, at a temperature of from 0° C. to 40° C.

In the compounds of the formula (I), of the present invention, the compound of the formula (I-4)

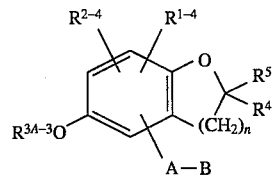

wherein $R^{1-4}$ and $R^{2-4}$ are the same meaning as hereinbefore defined for $R^1$ and $R^2$, provided that one of $R^{1-4}$ and $R^{2-4}$ represents a COOH group and the other group represents $COOR^6$, and the other symbols are the same meaning as hereinbefore defined may be prepared by hydrolysis of tert-butyl ester bond or by hydrogenation, of a suitable compound of the formula (I-1) or (I-2), i.e., a compound of the formula (I-f)

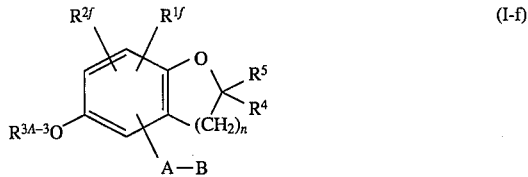

wherein $R^{1f}$ and $R^{2f}$ are the same meaning as hereinbefore defined for $R^1$ and $R^2$, provide that one of $R^{1f}$ and $R^{2f}$ represents COO-tert-butyl or $COO-CH_2C_6H_5$ groups, and the other group represents a $COOR^6$ group, the other symbols are the same meaning as hereinbefore defined.

Hydrolysis of a tert-butyl ester bond is known per se, and may be carried out, for example, in an inert organic solvent (e.g., dichloromethane, chloroform, methanol, dioxane, ethyl acetate, anisole etc.) in the presence of an organic acid (e.g., trifluoroacetic acid), or inorganic acid (e.g., hydrochloric acid), or a mixture of them, at a temperature of from 0° C. to 90° C.

Hydrogenation may be carried out by the same method as hereinbefore described.

In the compounds of the formula (I), of the present invention, the compound of the formula (I-5)

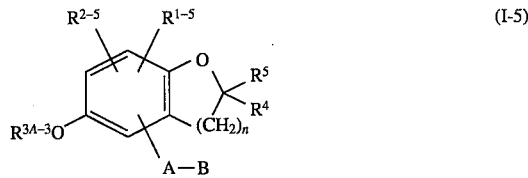

wherein both of $R^{1-5}$ and $R^{2-5}$ are COOH, and the other symbols are the same meaning as hereinbefore defined may be prepared by hydrolysis of a compound of formula (I-1) or (I-2), having both of $R^{1-1}$ and $R^{2-1}$ represent $COOR^6$ group, i.e., a compound of the formula (I-g)

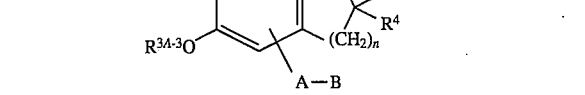

wherein both of $R^{1g}$ and $R^{2g}$ are $COOR^6$, and the other symbols are the same meaning as hereinbefore defined.

Hydrolysis of an ester bond may be carried out by the same method as hereinbefore described.

In the compounds of the formula (I), of the present invention, the compound of the formula (I-6)

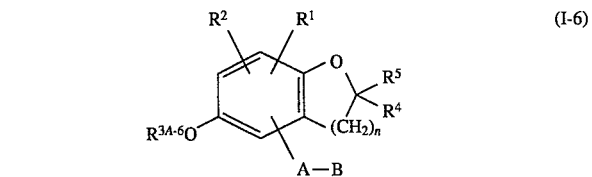

wherein $R^{3A-6}$ is C2–5 acyl, phenylcarbonyl or carbonyl substituted by a C7–10 phenylalkyl group, and the other symbols are the same meaning as hereinbefore defined may be prepared by acylation of a corresponding compound having a free hydroxy group, prepared, for example, by a method as hereinbefore described, i.e., of a compound of the formula (I-h)

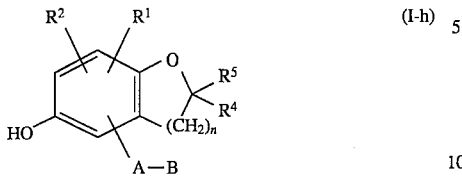

(I-h)

wherein all the symbols are the same meaning as hereinbefore defined.

The acylation is known per se, and may be carried out, for example, in an inert organic solvent (e.g., dichloromethane, etc.) or non solvent, in the presence of tertiary amine (e.g., pyridine, triethylamine, etc.), using the corresponding acyl halide or acid anhydride, at a temperature of from 0° C. to 40° C.

In the compounds of the formula (I), of the present invention, the compound of the formula (I-7)

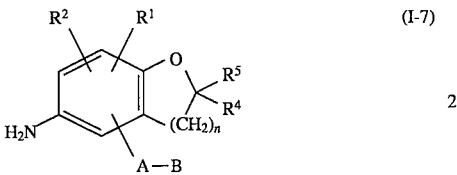

(I-7)

wherein all the symbols are the same meaning as hereinbefore defined may be prepared by reduction of nitro group of a compound of formula (II-7)

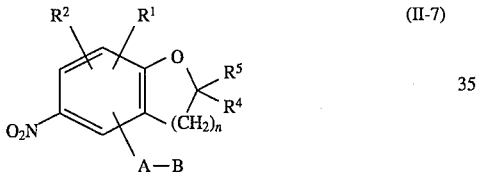

(II-7)

wherein all the symbols are the same meaning as hereinbefore defined.

Reduction of nitro group is known per se, and may be carried out, for example, by hydrogenation hereinbefore described.

In the compounds of the formula (I), of the present invention, the compound of the formula (I-8)

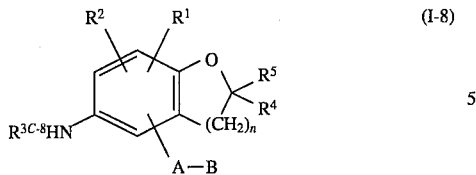

(I-8)

wherein $R^{3c-8}$ is C1–4 alkyl, C7–10 phenylalkyl, C2–5 acyl, phenylcarbonyl, carbonyl substituted by C7–10 phenylalkyl or C2–4 alkoxyalkyl, the other symbols are the same meaning as hereinbefore defined may be prepared by N-alkylation, N-acylation or N-alkoxyalkylation of a compound of the formula (I-7).

The N-alkylation is known per se, and may be carried out, for example, in an inert organic solvent (e.g., dichloromethane, chloroform, dimethylformamide, dimethylsulfoxide, etc.), in the presence of 1 equivalent of base (e.g., sodium hydride, sodium hydroxide, pyridine, triethylamine, etc.), using 1 equivalent of corresponding alkyl halide, at a temperature of from 0° C. to 100° C.

The N-acylation is known per se, and may be carried out, for example, in an inert organic solvent (e.g., dichloromethane, chloroform, dimethylformamide, dimethylsulfoxide, etc.), in the presence of 1 equivalent of base (e.g., sodium hydride, sodium hydroxide, pyridine, triethylamine, etc.), using 1 equivalent of corresponding acyl halide or acid anhydride, at a temperature of from 0° C. to 100° C.

The N-alkoxyalkylation is known per se, and may be carried out, for example, in an inert organic solvent (e.g., dichloromethane, chloroform, dimethylformamide, dimethylsulfoxide, etc.), in the presence of 1 equivalent of base (e.g., sodium hydride, sodium hydroxide, pyridine, triethylamine, etc.), using 1 equivalent of corresponding alkoxyalkyl halide, at a temperature of from 0° C. to 100° C.

In the compounds of the formula (I), of the present invention, the compound of the formula (I-9)

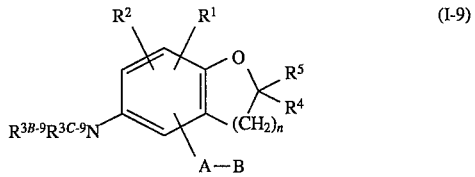

(I-9)

wherein $R^{3B-9}$ and $R^{3c-9}$ each, independently, is C1–4 alkyl, C7–10 phenylalkyl, C2–5 acyl, phenylcarbonyl, carbonyl substituted by C7–10 phenylalkyl or C2–4 alkoxyalkyl, the other symbols are the same meaning as hereinbefore defined may be prepared by N-alkylation, N-acylation or N-alkoxyalkylation of a compound of the formula (I-8).

The N-alkylation, N-acylation or N-alkoxyalkylation may be carried out by the same method as hereinbefore described.

The compounds of the formula (II-a), (II-b), (II-c) or (II-d) may be prepared by using known reactions. For example, they may be prepared by application or adaptation of the methods of Schemes 1 to 4 or methods described in the Examples.

Scheme 1

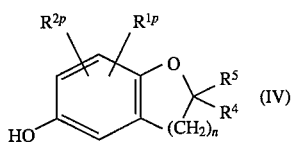

(IV)

-continued
Scheme 1
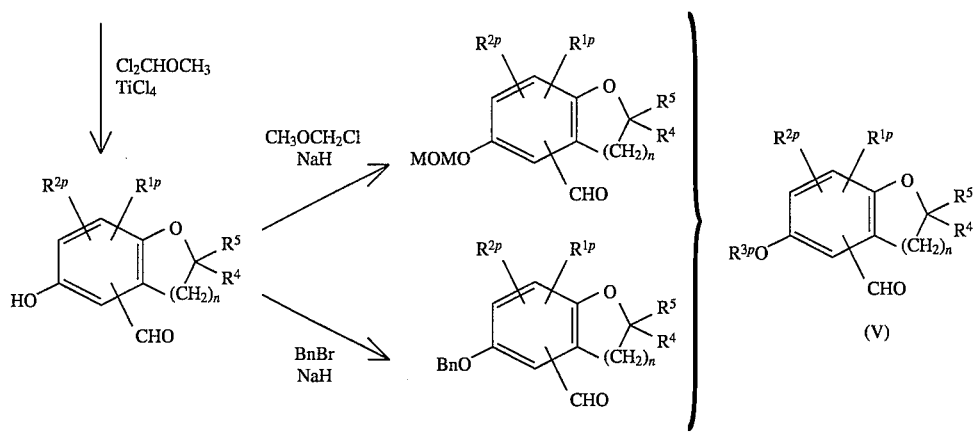
Scheme 2
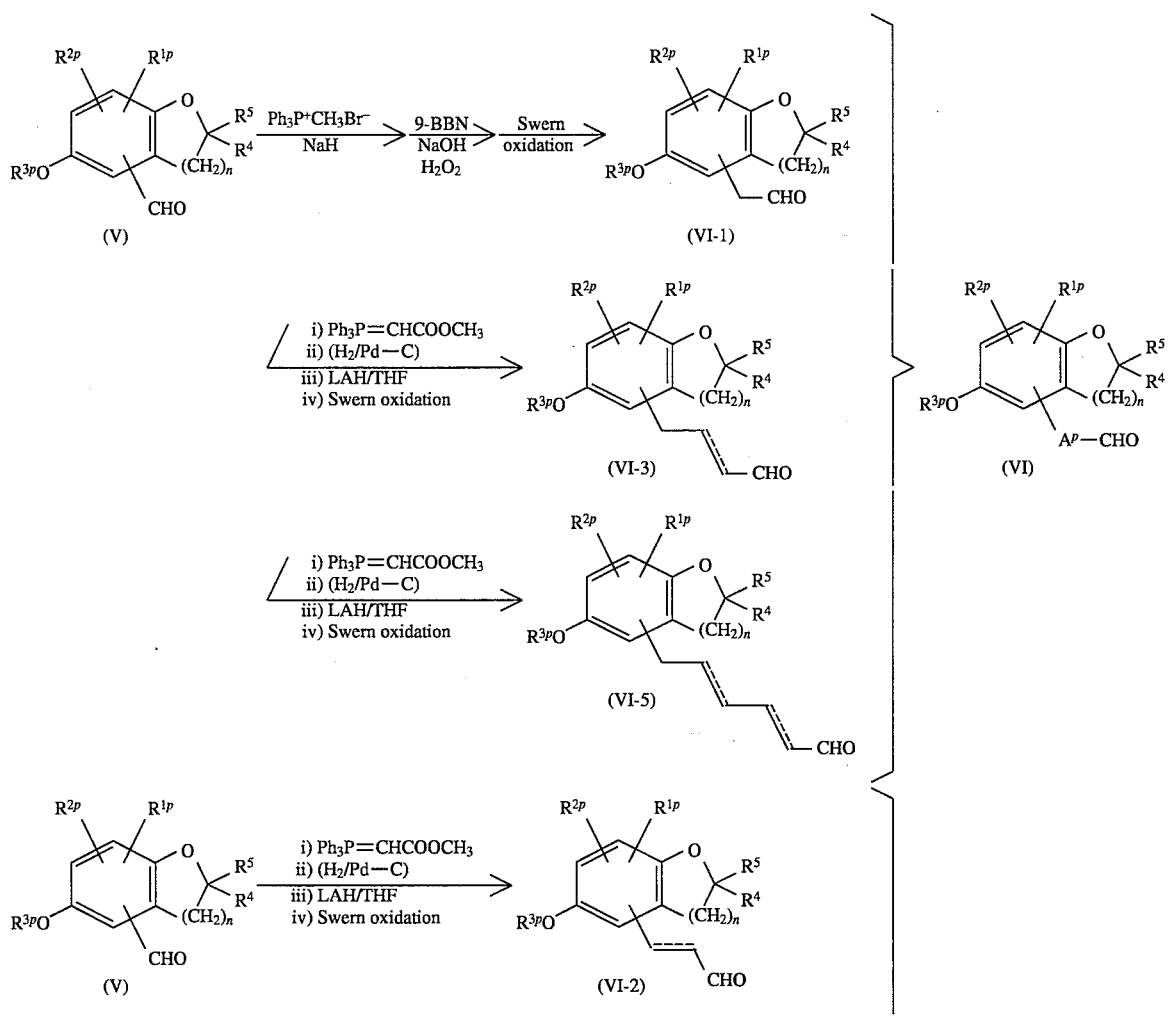

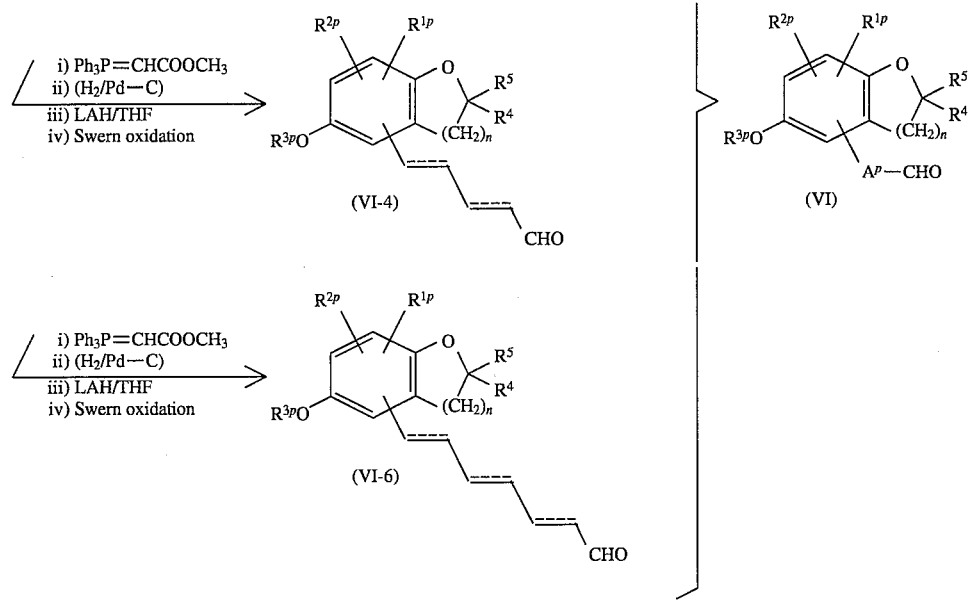
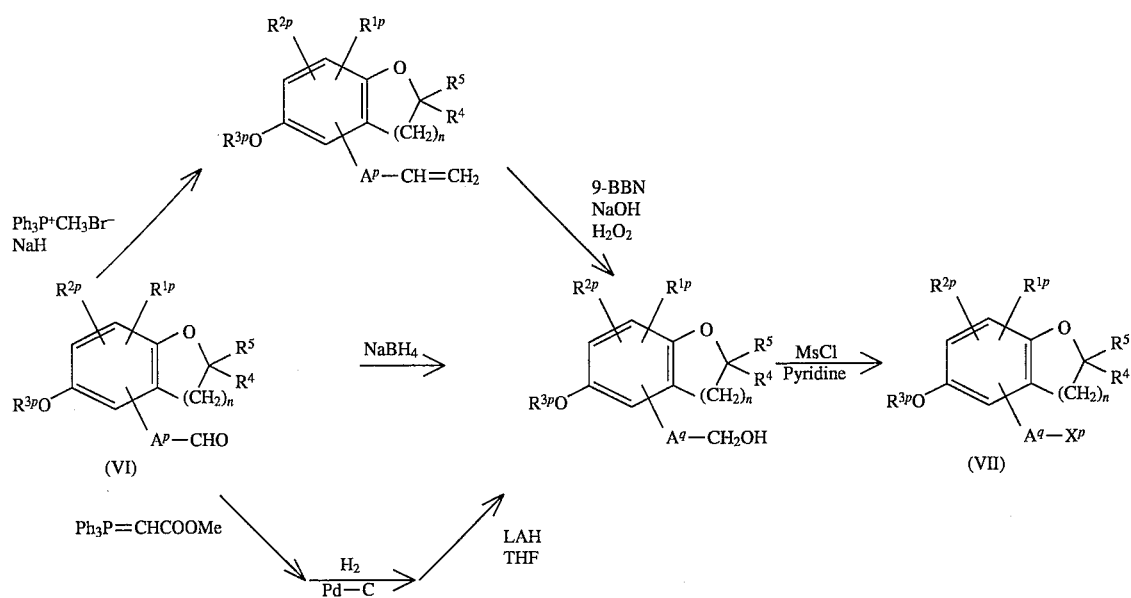
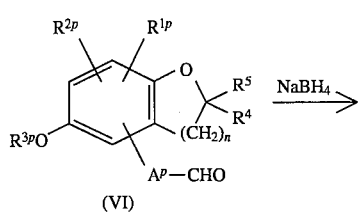
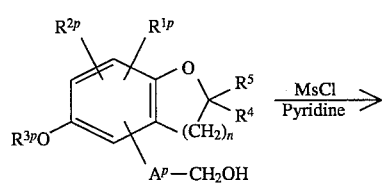

-continued
Scheme 4

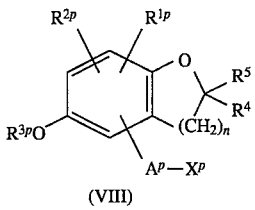

(VIII)

In the Scheme hereinbefore described MOM is methoxymethyl group, Bn is benzyl group, 9-BBN is 9-borabicyclo [3.3.1]nonane, LAH is lithium aluminum hydride, THF is tetrahydrofuran, MsCl is mesyl chloride, $R^{1p}$ and $R^{2p}$ are the same meaning as hereinbefore defined for $R^1$ and $R^2$, provided that $R^{1p}$ and $R^{2p}$ do not represent $COOR^6$ group (in which $R^6$ is the same meaning as hereinbefore defined), COOH or cyano groups, $R^{3p}$ is a methoxymethyl or benzyl, $A^p$ is C1–6 alkylene or C2–6 alkenylene, $A^q$ is C1–8 alkylene or C2–8 alkenylene, $X^p$ is mesyl group.

The compound of the formula (V) is part of the compound of the formula (II-c).

The compound of the formula (VI) is part of the compound of the formula (II-b).

The compound of the formula (VII) is part of the compound of the formula (II-a).

The compound of the formula (VIII) is part of the compound of the formula (II-d).

The compound of the formula (IV) used as starting material may be prepared by methods known per se. For example, the compound may be produced by methods described in the Examples of the present specification.

In each reaction in the present specification, products may be purified in a conventional manner. For example, purification may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

Other starting materials and reagents are known per se or may be prepared by known methods.

Pharmacological Activity

It has been confirmed that the compounds of formula (I), of the present invention have inhibitory activities on $TXA_2$ synthetase and on 5-lipoxygenase and/or scavenging actives on oxygen species. For example, in laboratory tests the following results were obtained.

i) Effect on human 5-lipoxygenase activity

Method

The assay mixture consisted of 85 µl of potassium/phosphate buffer (pH 7.4) containing 1.18 mM of calcium ion, 5 µl of cytosol fraction of polymorphonuclear leukocytes prepared from human peripheral blood and 5 µl of test compound. The reaction was initiated by the addition of 5 µl of 1 mM $^{14}$C-arachidonic acid after 5 min equilibration period. The incubation was carried out at 30° C. for 1 min and terminated by the addition of 300 µl of a ice-cold mixture of diethyl ether/methanol/1M citric acid (30/4/1). The mixture was mixed vigorously and centrifuged at 1700 G for 2 min at 4° C. The resultant organic layer was treated with sodium borohydride, kept cold for more than 10 min and then evaporated to dryness under gentle stream of nitrogen. After 200 µl of a mixture of diethyl ether/methanol (30/4) was added to the test tube, the contents were extracted by the addition of 100 µl of 1M citric acid followed by centrifugation (1700 G for 2 min at 4° C.). The products in the upper layer were chromatographed on silica gel thin-layer with a solvent system of diethyl ether/petroleum ether/acetic acid (85/15/0.01) and autoradiographed on X-ray film. The arachidonic acid metabolites and residual substrate were quantified by chromatoscanner. The 5-lipoxygenase activity was calculated by subtracting the conversion rate of total radioactivity into 15-hydroxy eicosatetraenoic acid from total radioactivity. The effect of compounds tested were expressed as percentage inhibition against 5-lipoxygenase activity in the vehicle (50% ethanol solution)-treated group.

The results are shown in the following Table 13.

TABLE 13

| Example No. | $IC_{50}$ (µM) |
| --- | --- |
| 4(e) | 0.69 |
| 10 | 0.48 |
| 11 | 1.1 |
| 13 | 0.46 | ii) Effect on human thromboxane $A_2$ synthetase activity

Method

Washed platelet was prepared from citrate-treated [⅑ (v/v)] human peripheral blood and suspended in $Ca^{++}$-free Krebs-Henseleit solution (pH 7.4) at a concentration of $10.8 \times 10^7$ cells/ml. The assay mixture contained 185 µl of cell suspension, 5 µl of test compound and 10 µl of 100 µM $^{14}$C-arachidonic acid. Before the reaction was started by the addition of $^{14}$C-arachidonic acid, the other components were equilibrated for 2 min at 37 ° C. The incubation was carried out at 37° C. for 2 min and terminated by the addition of 300 µl of a mixture of diethyl ether/methanol/1M citric acid (30/4/1). The contents were mixed and then centrifuged for 2 min at 1700 G at 4° C. The products in the resultant organic layer were chromatographed on silica gel thin-layer using a solvent system of a mixture of ethyl acetate/isooctane/acetic acid/$H_2O$ (110/50/20/100) and then autoradiographed on X-ray film. The arachidonic acid metabolites and residual substrate were quantified by chromatoscanner. $TXA_2$ synthetase activity was expressed as the conversion rate of total radioactivity into thromboxane $B_2$ ($TXB_2$), a stable metabolite of $TXA_2$. The effects of compounds tested were expressed as percentage inhibition against the conversion rate of total radioactivity into $TXB_2$ in vehicle (50% ethanol solution)-treated group.

The results are shown in the following Table 14.

TABLE 14

| Example No. | $IC_{50}$ (µM) |
| --- | --- |
| 4(e) | 8.6 |
| 10 | 1.4 |
| 11 | 0.55 |
| 13 | 1.0 | iii) Effect on leukotriene $B_4$ ($LTB_4$) and $TXB_2$ production from human whole blood Method Heparinized final concentration (10U/ml) whole blood from healthy volunteers and compound tested in a volume ratio of 100:1 were incubated for 5 min at 37° C. and stimulated by the addition of ½₀₀ volume of 6 mM Ca ionophore A23187. The incubation was carried out for 5 min and terminated by centrifugation (12,000 rpm for 1–2 min). Resultant plasma was stocked at −70° C. until determination of the levels of $LTB_4$ and $TXB_2$. Plasma levels of $LTB_4$ and $TXB_2$ were determined by commercially available EIA kits (Cayman Chemical Company) following partial purification. The effect of compound tested was expressed as percentage inhibition against the amounts of $LTB_4$ and $TXB_2$ generated in vehicle (50% ethanol solution)-treated group.

The results are shown in the following Table 15.

TABLE 15

| Example No. | Inhibition (10 μM) | |
|---|---|---|
| | $LTB_4$ | $TXB_2$ |
| 2 | 74% | 92% |
| 2(v) | 61% | 89% |
| 2(x) | 70% | 82% |
| 12(d) | 40% | 69% |
| 14 | 21% | 15% |
| 15 | 44% | 94% |
| 15(a) | 71% | 53% |
| 17 | 22% | 36% | iv) Antioxidant action

Method

Male Sprague-Dawley rat fasted overnight was anesthetized with diethyl ether, and liver was perfused, isolated and homogenized with 1.15% KCl (10% homogenate). The assay mixture contained 200 μl of liver homogenate, 5 μl of test compound and 10 μl of 4.4 mM $FeCl_2$. The reaction was initiated by the addition of $FeCl_2$, and the incubation was carried out for 1 hr at 37° C. The amounts of lipid peroxides produced during this incubation period were determined as thiobarbituric acid reactive substances (TBARS) according to the method described by OHKAWA et. al. (Analytical Biochemistry, 95, 351–358, 1979). The effects of compounds tested were expressed as percentage inhibition against the amounts of TBARS produced in vehicle (50% ethanol solution)-treated group.

The results are shown in the following Table 16.

TABLE 16

| Example No. | $IC_{50}$ (μM) |
|---|---|
| 4(e) | 2.6 |
| 10 | 4.0 |
| 11 | 3.7 |

Toxicity

The toxicity of the compounds of the present invention is very weak. Therefore, the compounds of the present invention may be considered to be sufficiently safe and suitable for pharmaceutical use.

Application for Pharmaceuticals

The compounds of the formula (I), of the present invention, have inhibitory activities on $TXA_2$ synthetase and on 5-lipoxygenase and/or scavenging actives on oxygen species, and are useful in the prevention and/or the treatment of conditions which can be ameliorated by the administration of an effective dose of an inhibitor of $TXA_2$ synthetase, of 5-lipoxygenase and/or of an active oxygen species scavenger, including thrombosis, arteriosclerosis, ischemic heart diseases or brain diseases, bronchial asthma, renal inflammation, rheumatism, arthritis, gout, psoriasis, ulcerative colitis, trichophytosis, cardiac infarction and allergy diseases.

For the purpose above described, the compounds of the formula (I), of the present invention, non-toxic salts thereof, acid addition salts thereof and hydrates thereof may be normally administered systemically or partially, usually by oral or parenteral administration.

The doses to be administered are determined depending upon e.g., age, body weight, symptom, the desired therapeutic effect, the route of administration, and the duration of the treatment. In the human adult, the doses per person per dose are generally between 1 mg and 1000 mg, by oral administration, up to several times per day, and between 100 μg and 100 mg, by parenteral administration up to several times per day, or by continuous intravenous administration between 1 and 24 hrs. per day.

As mentioned above, the doses to be used depend upon various conditions. Therefore, there are cases in which doses lower than or greater than the ranges specified above may be used.

When administration of the compounds of the present invention, it is used as solid compositions, liquid compositions or other compositions for oral administration, as injections, liniments or suppositories for parenteral administration.

Solid compositions for oral administration include compressed tablets, pills, capsules, dispersible powders, and granules. Capsules include hard capsules and soft capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate). The compositions may also comprise, as is normal practice, additional substances other than inert diluents: e.g. lubricating agents (such as magnesium stearate), disintegrating agents (such as cellulose calcium glycolate), stabilizing agents (such as lactose), and agents to assist dissolution (such as glutamic acid, asparaginic acid).

The tablets or pills may, if desired, be coated with a film of gastric or enteric material (such as sugar, gelatin, hydroxypropyl cellulose or hydroxypropylmethyl cellulose phthalate), or be coated with more than two films. Coating may include containment within capsules of absorbable materials such as gelatin.

Liquid compositions for oral administration include pharmaceutically-acceptable solutions, emulsions, suspensions, syrups and elixirs. In such compositions, one or more of the active compound(s)is or are contained in inert diluent(s) commonly used in the art (such as purified water, ethanol). Besides inert diluents, such compositions may also comprise adjuvants (such as wetting agents, suspending agents), sweetening agents, flavouring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (such as sodium sulfate), isotonic buffer (such as sodium chloride, sodium citrate, citric acid). For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. In such compositions, one more active compound(s) is or are admixed with at least one inert aqueous diluent(s) (such as distilled water for injection, physiological salt solution) or inert non-aqueous diluent(s) (such as propylene glycol, polyethylene glycol, olive oil, ethanol, POLYSORBATE80 (registered trade mark)).

Injections may comprise additional materials other than inert diluents: e.g. preserving agents, wetting agents, emulsifying agents, dispersing agents, stabilizing agent (such as lactose), and agents to assist dissolution (such as glutamic acid, asparaginic acid).

They may be sterilized for example, by filtration through a bacteria-retaining filter, by incorporation of sterilizing agents in the compositions or by irradiation. They may also be manufactured in the form of sterile solid compositions, for example, by freeze-drying, and which may be dissolved in sterile water or some other sterile diluent(s) for injection immediately before used.

Other compositions for parenteral administration include liquids for external use, and endermic liniments, ointment, suppositories and pessaries which comprise one or more of the active compound(s) and may be prepared by methods known per se.

REFERENCE EXAMPLES AND EXAMPLES

The following reference examples and examples illustrate the present invention, but not limit the present invention.

The solvents in the parentheses show the developing or eluting solvents and the ratios of the solvents used are by volume in chromatographic separations.

Unless otherwise specified, "IR" spectra were measured by the KBr method.

REFERENCE EXAMPLE 1

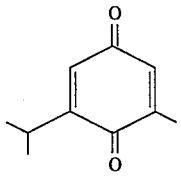

Salcomine (7.5 g) was added to a solution of 3-isopropyl-5-methyl-phenol (30 g) in ethanol (500 ml), and under an atmosphere of oxygen, the mixture was stirred for three days at room temperature. The mixture was concentrated, diluted with ethyl acetate, and filtered through Celite (commercially available). The filtrate was concentrated. The residue was purified by column chromatography on silica gel (hexane:ethyl acetate=20:1) to give the mixture (12.3 g) of the desired compound having the following physical data and starting material, i.e. the phenol compound.

TLC:Rf 0.55 (hexane:ethyl acetate=8:1).

REFERENCE EXAMPLE 2

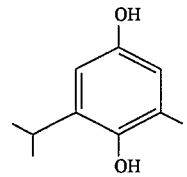

Sodium borohydride (1.5 g) was added to a solution of the mixture prepared in reference example 1 (12.3 g) in dichloromethane (150 ml) at 0° C. Methanol was added until the color of the mixture changed from red into pale yellow. The mixture was stirred for 30 min at 0° C. The mixture was quenched by addition of a saturated aqueous solution of ammonium chloride and warmed to room temperature. The mixture was extracted with ethyl acetate and the extract was washed with water and a saturated aqueous solution of sodium chloride, successively, dried over anhydrous magnesium sulfate and concentrated. The residue was purified by column chromatography on silica gel (hexane:ethyl acetate=10:1) to give the desired compound (6.5 g) having the following physical data.

TLC:Rf 0.15 (hexane:ethyl acetate=4:1).

REFERENCE EXAMPLE 3

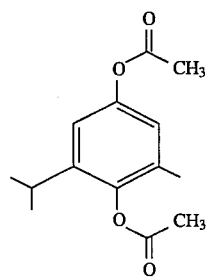

Dimethylaminopyridine (0.5 g) and acetyl chloride (6.0 ml) were added to a solution of the compound prepared in reference example 2 (5.5 g) in pyridine (27 ml) at 0° C. and the mixture was stirred for 2 h at room temperature. The mixture was quenched by addition of ice water (40 ml) and extracted with ethyl acetate. The extract was washed with 2N aqueous solution of hydrochloric acid, water, a saturated aqueous solution of sodium hydrogen carbonate, water and a saturated aqueous solution of sodium chloride, successively, dried over anhydrous magnesium sulfate and concentrated. The residue was purified by column chromatography on silica gel (hexane:ethyl acetate=9:1) to give the desired compound (9.1 g) having the following physical data.

TLC:Rf 0.42 (hexane:ethyl acetate=4:1).

REFERENCE EXAMPLE 4

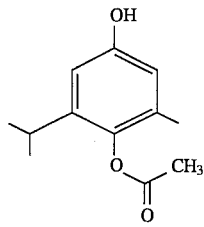

A solution of sodium dithionite (800 mg) and sodium hydroxide (733 mg) in water (7 ml) was slowly added to a solution of the compound prepared in reference example 3 (4.4 g) in ethanol (60 ml) at 0° C. The mixture was stirred for 1 h at room temperature and poured into ice water (200 ml). After 1N aqueous solution of hydrochloric acid was added to the solution until pH 6, the mixture was extracted with diethyl ether. The extract was washed with water and a saturated aqueous solution of sodium chloride, successively, dried over anhydrous magnesium sulfate and concentrated to give the desired compound (3.6 g) having the following physical data.

TLC:Rf 0.27 (hexane:ethyl acetate=4:1).

REFERENCE EXAMPLE 5

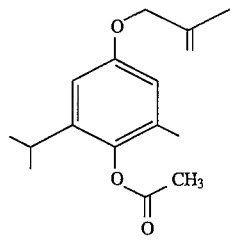

β-Methallyl chloride (3.7 ml) and potassium carbonate (2.84 g) were added to a solution of the compound prepared in reference example 4 (3.9 g) in dimethylformamide (30 ml) and the mixture was stirred for 5 h at 70° C. The mixture was quenched by addition of ice water (120 ml) and extracted with a mixture of ethyl acetate and diethyl ether (1:1). The extract was washed with water and a saturated aqueous solution of sodium chloride, successively, dried over anhydrous magnesium sulfate and concentrated. The residue was purified by column chromatography on silica gel (hexane:ethyl acetate=19:1) to give the desired compound (4.3 g) having the following physical data.

TLC:Rf 0.63 (hexane:ethyl acetate=4:1).

REFERENCE EXAMPLE 6

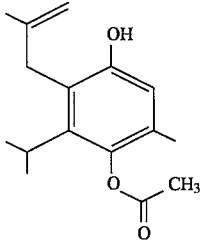

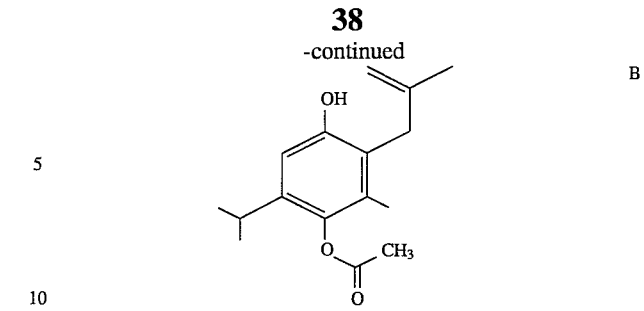

A solution of the compound prepared in reference example 5 (4.3 g) in diethylaniline (30 ml) was stirred for 5 h at 200° C. After it was cooled to room temperature, the mixture was diluted with ethyl acetate. The solution was washed with 2N aqueous solution of hydrochloric acid until pH 1, a saturated aqueous solution of sodium hydrogen carbonate, water and a saturated aqueous solution of sodium chloride, successively, dried over anhydrous magnesium sulfate and concentrated. The residue was purified by column chromatography on silica gel (hexane:ethyl acetate= 8:1) to give the desired compound A (1.2 g) and compound B (2.0 g) respectively, having the following physical data.

TLC:A:Rf 0.13 (hexane:ethyl acetate=8:1);

B:Rf 0.23 (hexane:ethyl acetate=8:1).

REFERENCE EXAMPLE 7

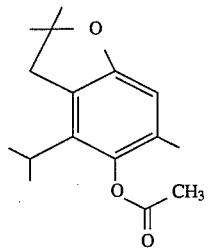

Boron trifluoride diethyl etherate (0.84 ml) was added to a solution of the compound A prepared in reference example 6 (1.19 g) in dichloromethane at 0° C. The mixture was stirred for 30 min at 0° C. The mixture was quenched by addition of a saturated aqueous solution (10 ml) and extracted with ethyl acetate. The extract was washed with water and a saturated aqueous solution of sodium chloride, successively, dried over anhydrous magnesium sulfate and concentrated to give the desired compound (1.1 g) having the following physical data.

TLC:Rf 0.58 (hexane:ethyl acetate=4:1).

REFERENCE EXAMPLE 8

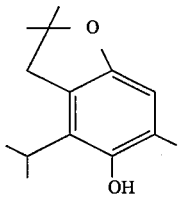

Sodium methoxide (680 mg) was added to a solution of the compound prepared in reference example 7 (1.1 g) in methanol (10 ml) and the mixture was stirred for 2 h at room temperature. The mixture was cooled to 0° C. and acetic acid (0.75 ml) was slowly added to the mixture. The mixture was concentrated and water was added to the residue. The mixture was extracted with ethyl acetate. The extract was washed with a saturated aqueous solution of sodium hydrogen carbonate, water and a saturated aqueous solution of sodium chloride, successively, dried over anhydrous magnesium sulfate and concentrated. The residue was purified by column chromatography on silica gel (hexane:ethyl acetate=19:1) to give the desired compound (805 mg) having the following physical data.

TLC:Rf 0.54 (hexane:ethyl acetate=4:1).

REFERENCE EXAMPLE 9

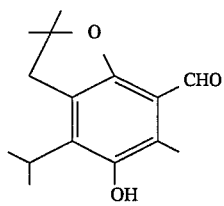

Titanium tetrachloride (1 ml) and α, α-dichloromethyl methyl ether (0.82 ml) were added to a solution of a compound prepared in reference example 8 (800 mg) in dichloromethane (10 ml) at 0° C. and the mixture was stirred for 30 min at 0° C. The mixture was quenched by addition of ice water and stirred for 20 min. The mixture was extracted with ethyl acetate. The extract was washed with water and a saturated aqueous solution of sodium chloride, successively, and dried over anhydrous magnesium sulfate and concentrated. The residue was purified by column chromatography on silica gel (hexane:ethyl acetate=9:1) to give the desired compound (890 mg) having the following physical data.

TLC:Rf 0.42 (hexane:ethyl acetate=4:1).

REFERENCE EXAMPLE 10

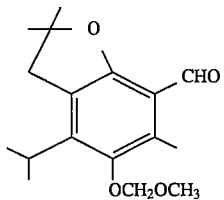

Sodium hydride (212 mg, 60% content) was added to a solution of the compound prepared in reference example 9 (880 mg) in dimethylformamide (8 ml) at 0° C. and the mixture was stirred for 30 min at room temperature. Chloromethyl methyl ether (0.4 ml) was added to the mixture at 0° C. and the mixture was stirred for 10 min at room temperature. The mixture was quenched by addition of water and extracted with a mixture of diethyl ether and ethyl acetate (1:1 ). The extract was washed with water and a saturated aqueous solution of sodium chloride, successively, dried over anhydrous magnesium sulfate, and concentrated. The residue was purified by column chromatography on silica gel (hexane:ethyl acetate=19:1) to give the desired compound (926 mg) having the following physical data.

TLC:Rf 0.52 (hexane:ethyl acetate=4:1).

REFERENCE EXAMPLE 11

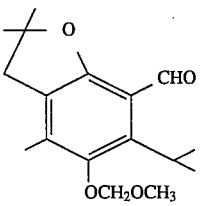

By the same procedure as reference example 7→reference example 8→reference example 9→reference example 10, using the compound B prepared in reference example 6, the desired compound having the following physical data was given.

TLC:Rf 0.46 (hexane:ethyl acetate=5:1).

REFERENCE EXAMPLE 12

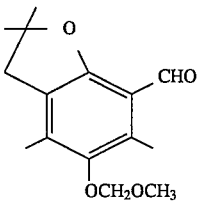

By the same procedure as reference example 1→reference example 2→reference example 3→reference example 4→reference example 5→reference example 6→reference example 7→reference example 8→reference example 9→reference example 10, using 3,5-dimethylphenol instead of 3-isopropyl-5-methylphenol, the desired compound having the following physical data was given.

TLC:Rf 0.36 (hexane:ethyl acetate=4:1).

REFERENCE EXAMPLE 12 (a)–(e)

By the same procedure as reference example 12, the compounds shown in the following Table 17 were given by using corresponding phenol instead of 3,5-dimethylphenol.

TABLE 17
| Reference example No. | Phenol (starting material) | Product |
|---|---|---|
| 12(a) | 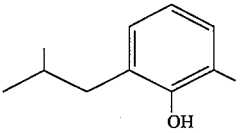 | 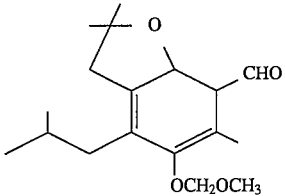 |
| 12(b) | 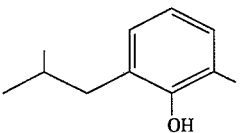 | 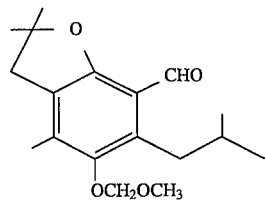 |
| 12(c) | 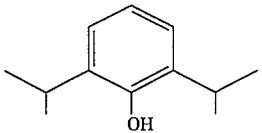 | 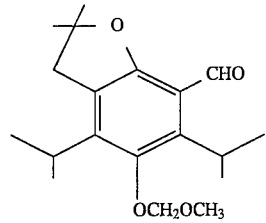 |
| 12(d) | 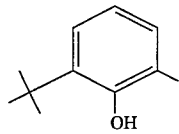 | 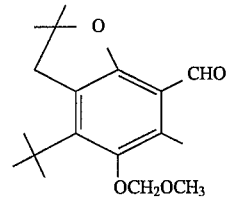 |
| 12(e) | 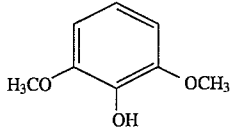 | 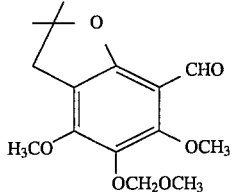 |
| 12(f) | 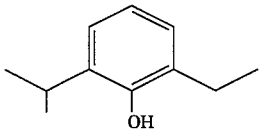 | 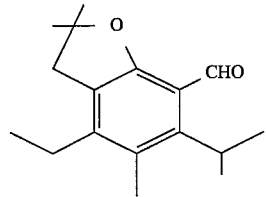 |
| 12(g) | 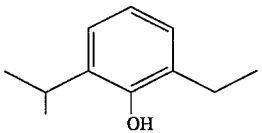 | 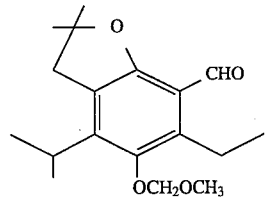 |

TABLE 17-continued

| Reference example No. | Phenol (starting material) | Product |
| --- | --- | --- |
| 12(h) | 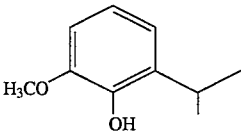 | 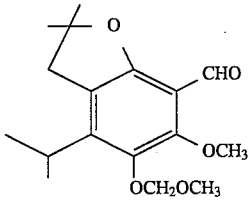 |

REFERENCE EXAMPLE 13

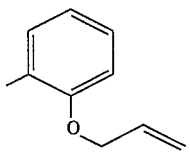

Sodium hydride (2.7 g, 60% content) was added to a solution of 2methylphenol (6 g) in dimethylformamide (40 ml) and the mixture was stirred for 30 min at room temperature. Allyl bromide (6.3 ml) was added to the mixture. The mixture was stirred for 30 min at room temperature. The mixture was poured into ice water (150 ml) and extracted with a mixture of hexane and ethyl acetate (2:1). The extract was washed with water and a saturated aqueous solution of sodium chloride, successively, and dried over anhydrous magnesium sulfate, and concentrated to give the desired compound (8.3 g) having the following physical data.

TLC:Rf 0.72 (hexane:ethyl acetate=9:1).

REFERENCE EXAMPLE 14

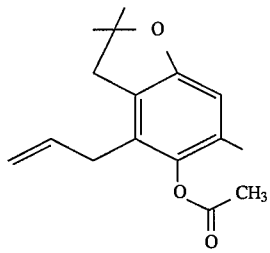 A

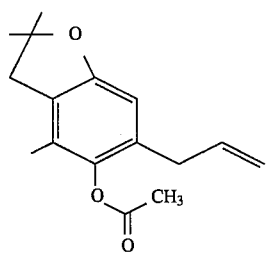 B

By the same procedure as reference example 6→reference example 1→reference example 2→reference example 3→reference example 4→reference example 5→reference example 6→reference example 7, using the compound prepared in reference example 13, the desired compounds having the following physical data were given.

TLC:A:Rf 0.55 (hexane:ethyl acetate=4:1); B:Rf 0.38 (hexane:ethyl acetate=9:1).

REFERENCE EXAMPLE 15

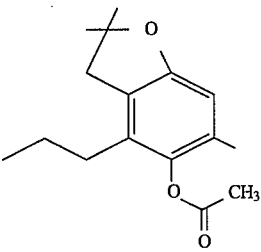

5% Palladium on activated carbon (100 mg) was added to a solution of the compound A prepared in reference example 14 (540 mg) in ethanol (5 ml) and the mixture was stirred for 1 h at room temperature under an atmosphere of hydrogen. The mixture was filtered through Celite (being on sale). The filtrate was concentrated to give the desired compound (543 mg) having the following physical data.

TLC:Rf 0.24 (hexane:ethyl acetate=10:1 (twice)).

REFERENCE EXAMPLE 16

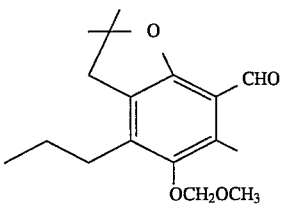

By the same procedure as reference example 8→reference example 9→reference example 10, using the compound prepared in reference example 15, the desired compound having the following physical data was given.

TLC:Rf 0.35 (hexane:ethyl acetate=9:1).

REFERENCE EXAMPLE 17

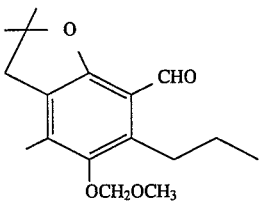

By the same procedure as reference example 15→reference example 16, using the compound B prepared in reference example 14, the desired compound having the following physical data was given.

TLC:Rf 0.39 (hexane:ethyl acetate=9:1).

REFERENCE EXAMPLE 18

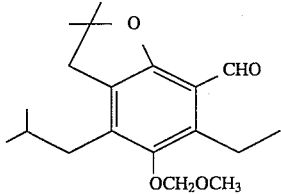

By the same procedure as reference example 5→reference example 6→reference example 15→reference example 12, using 2-ethylphenol, the desired compound having the following physical data was given.

TLC:Rf 0.54 (hexane:ethyl acetate=4:1).

REFERENCE EXAMPLE 19

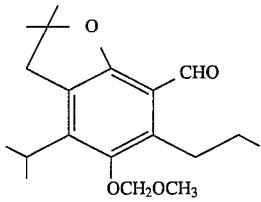

A

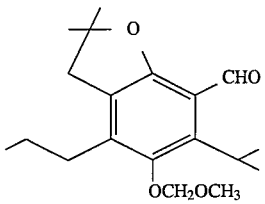

B

By the same procedure as reference example 13→reference example 6→reference example 15→reference example 12, using 2-isopropylphenol, the desired compounds having the following physical data were given.

TLC:A:Rf 0.58 (hexane:ethyl acetate=5:1); B:Rf 0.44 (hexane:ethyl acetate=5:1).

REFERENCE EXAMPLE 20

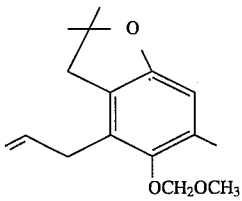

By the same procedure as reference example 8→reference example 10, using the compound A prepared in reference example 14, the desired compound having the following physical data was given.

TLC:Rf 0.33 (hexane:ethyl acetate=19:1).

REFERENCE EXAMPLE 21

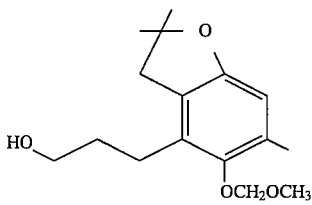

9-Borabicycro[3.3.1]nonane (3.09 ml, 0.5M solution in tetrahydrofuran) was added to a solution of the compound prepared in reference example 20 (270 mg) in tetrahydrofuran (1 ml) and the mixture was stirred for 2 h at room temperature. Methanol (0.87 ml), 6N aqueous solution of sodium hydroxide (0.3 ml) and 30% aqueous solution of hydrogen peroxide (0.6 ml) were added to the mixture, successively. After the mixture was stirred for 30 min at 50° C., and cooled to room temperature and concentrated. Water was added to the residue and the mixture was extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=2:1) to give the desired compound (289 mg) having the following physical data.

TLC:Rf 0.14 (hexane:ethyl acetate=3:2).

REFERENCE EXAMPLE 22

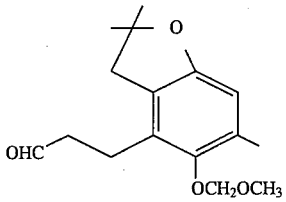

A solution of dimethylsulfoxide (0.22 ml) in dichloromethane (1 ml) was added dropwise to a solution of oxalyl chloride (0.13 ml) in dichloromethane (3 ml) at −60° C. under an atmosphere of argon and the mixture was stirred for 15 min at −60° C. A solution of the compound prepared in reference example 21 (288 mg) in dichloromethane (2 ml) was added to the mixture. The mixture was stirred for 30 min at −60° C. Triethylamine (0.72 ml) was added to the mixture. The mixture was stirred for 10 min at room temperature. The mixture was quenched by addition of water (5 ml) and extracted with ethyl acetate. The extract was washed with 1N aqueous solution of hydrochloric acid, water, a saturated aqueous solution of sodium hydrogen carbonate and a saturated aqueous solution of sodium chloride, successively, dried over anhydrous magnesium sulfate and concentrated to give the desired compound (280 mg) having the following physical data.

TLC:Rf 0.52 (hexane:ethyl acetate=2:1).

REFERENCE EXAMPLE 23

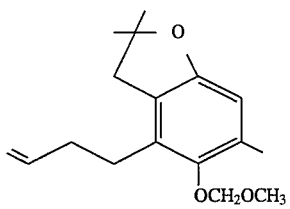

A suspension of sodium hydride (82 mg, 60% content) in dimethylsulfoxide (1 ml) was stirred for 1 h at 70° C. under an atmosphere of argon. The mixture was cooled to room temperature. A solution of methyltriphenylphosphonium bromide (734 mg) in dimethylsulfoxide (2 ml) was added to the mixture. The mixture was stirred for 5 min. A solution of the compound prepared in reference example 22 (280 mg) in dimethylsulfoxide (2 ml) was added to the mixture. The mixture was stirred for 20 min at room temperature. The mixture was poured into ice water (20 ml) and extracted with a mixture of diethyl ether and ethyl acetate (2:1). The extract was washed with a saturated aqueous solution of sodium chloride, dried over anhydrous magnesium sulfate and concentrated. The residue was purified by column chromatography on silica gel (hexane:ethyl acetate=40:1) to give the desired compound (204 mg) having the following physical data.

TLC:Rf 0.48 (hexane:ethyl acetate=9:1).

REFERENCE EXAMPLE 24

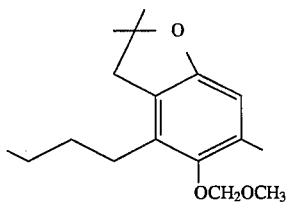

By the same procedure as reference example 15, using the compound prepared in reference example 23 (199 mg), the desired compound (200 mg) having the following physical data was given.

TLC:Rf 0.53 (hexane:ethyl acetate=9:1).

REFERENCE EXAMPLE 25

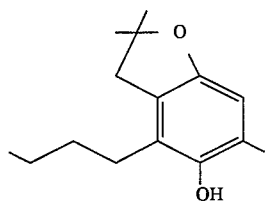

Hydrogen chloride (0.7 ml, 4N solution in dioxane) was added to a solution of the compound prepared in reference example 24 (200 mg) in dioxane (2 ml) and methanol (0.5 ml). The mixture was stirred for 15 min at room temperature and concentrated. A saturated aqueous solution of sodium hydrogen carbonate was added to the residue and the mixture was extracted with ethyl acetate. The extract was washed with water and a saturated aqueous solution of sodium chloride, successively, dried over anhydrous magnesium sulfate and concentrated to give the desired compound (167 mg) having the following physical data.

TLC:Rf 0.36 (hexane:ethyl acetate=9:1).

REFERENCE EXAMPLE 26

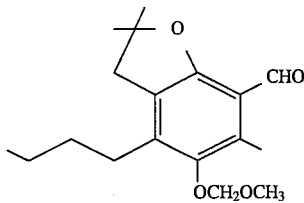

By the same procedure as reference example 9→reference example 10, using the compound prepared in reference example 25, the desired compound having the following physical data was given.

TLC:Rf 0.33 (hexane:ethyl acetate=9:1).

REFERENCE EXAMPLE 27

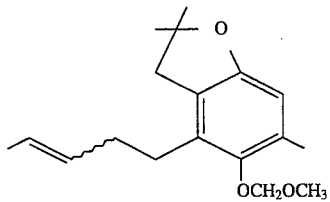

A suspension of sodium hydride (56 mg, 60% content) in dimethylsulfoxide (1 ml) was stirred for 1 h at 70° C. under an atmosphere of argon. The mixture was cooled to room temperature. A solution of ethyltriphenylphosphonium bromide (520 mg) in dimethylsulfoxide (1 ml) was added to the mixture. The mixture was stirred for 20 min. A solution of the compound prepared in reference example 22 (220 mg) in dimethylsulfoxide (1 ml) was added to the mixture. The mixture was stirred for 30 min at room temperature. The mixture was poured into ice water and extracted with ethyl acetate. The extract was washed with a saturated aqueous solution of sodium chloride, dried over anhydrous magnesium sulfate and concentrated. The residue was purified by column chromatography on silica gel (hexane:ethyl acetate= 50:1) to give the desired compound (228 mg) having the following physical data.

TLC:Rf 0.83 (hexane:ethyl acetate=4:1).

REFERENCE EXAMPLE 28

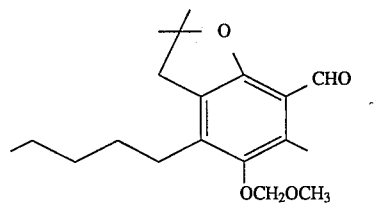

By the same procedure as reference example 24→reference example 25→reference example 26, using the compound prepared in reference example 27, the desired compound having the following physical data was given.

TLC:Rf 0.37 (hexane:ethyl acetate=8:1).

REFERENCE EXAMPLE 29

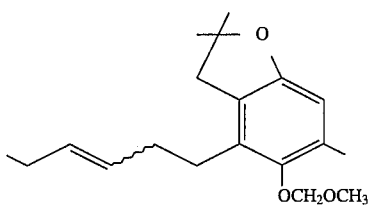

A suspension of sodium hydride (56 mg, 60% content) in dimethylsulfoxide (1 ml) was stirred for 1 h at 70° C. under an atmosphere of argon. The mixture was cooled to room temperature. A solution of propyltriphenylphosphonium bromide (539 mg) in dimethylsulfoxide (1 ml) was added to the mixture. The mixture was stirred for 20 min. A solution of the compound prepared in reference example 22 in (167 mg) in dimethylsulfoxide (1 ml) was added to the mixture. The mixture was stirred for 30 min at room temperature. The mixture was poured into ice water and extracted with ethyl acetate. The extract was washed with a saturated aqueous solution of sodium chloride, dried over anhydrous magnesium sulfate and concentrated. The residue was purified by column chromatography on silica gel (hexane:ethyl acetate= 50:1) to give the desired compound (172 mg) having the following physical data.

TLC:Rf 0.83 (hexane:ethyl acetate=4:1).

REFERENCE EXAMPLE 30

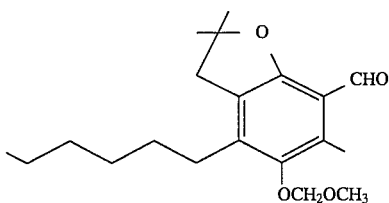

By the same procedure as reference example 28, using the compound prepared in reference example 29, the desired compound having the following physical data was given.

TLC:Rf 0.53 (hexane:ethyl acetate=8:1).

REFERENCE EXAMPLE 31

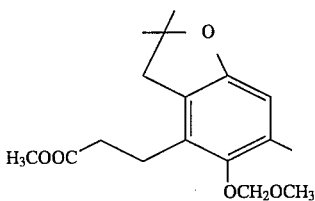

Sodium dihydrogenphosphate (200 mg), 30% aqueous solution of hydrogen peroxide (0.26 ml) and sodium chlorite (570 mg) were added to a solution of the compound prepared in reference example 22 (400 mg) in tert-butyl alcohol (5.6 ml) and water (1.6 ml). The mixture was stirred for 1 h at room temperature. The mixture was quenched by addition of 1N aqueous solution of hydrochloric acid. The mixture was extracted with ethyl acetate. The extract was washed with water. A solution of diazomethane in diethyl ether was added to the extract at 0° C. The mixture was washed with a saturated aqueous solution of sodium hydrogen carbonate, water and a saturated aqueous solution of sodium chloride, successively, dried over anhydrous magnesium sulfate and concentrated. The residue was purified by column chromatography on silica gel (hexane:ethyl acetate=5:1) to give the desired compound (304 mg) having the following physical data.

TLC:Rf 0.66 (hexane:ethyl acetate=2:1).

REFERENCE EXAMPLE 32

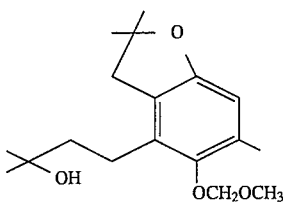

Methyllithium (2 ml, 1.19M solution in diethyl ether) was added to a solution of the compound prepared in reference example 31 (384 mg) in diethyl ether (5 ml) at −78° C. under an atmosphere of argon and the mixture was stirred for 15 min at same temperature. The mixture was quenched by addition of a saturated aqueous solution of ammonium chloride and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=3:1) to give the desired compound (286 mg) having the following physical data.

TLC:Rf 0.13 (hexane:ethyl acetate=3:1).

REFERENCE EXAMPLE 33

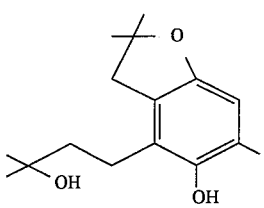

By the same procedure as reference example 25, using the compound prepared in reference example 32, the desired compound having the following physical data was given.

TLC:Rf 0.11 (hexane:ethyl acetate=3:1).

REFERENCE EXAMPLE 34

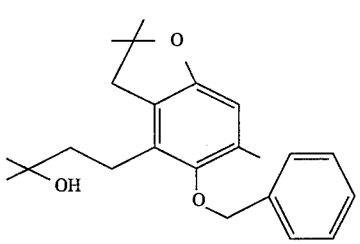

Potassium carbonate (238 mg) and benzyl bromide (0.12 ml) were added to the compound prepared in reference example 33 (222 mg) in acetone (10 ml) under an atmosphere of argon. The mixture was stirred at 60° C. overnight.

The mixture was quenched by addition of water, concentrated to remove acetone and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=4:1) to give the desired compound (300 mg) having the following physical data.

TLC:Rf 0.28 (hexane:ethyl acetate=3:1).

REFERENCE EXAMPLE 35

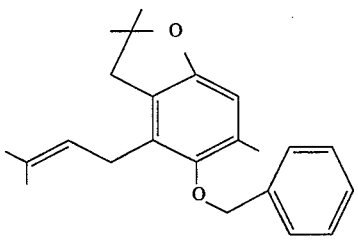

Phosphoryl chloride (0.16 ml) was added to a solution of the compound prepared in reference example 34 (300 mg) in pyridine (3 ml) under an atmosphere of argon. The mixture was stirred for 40 min at 120° C. The mixture was quenched by addition of 1N aqueous solution of hydrochloric acid and extracted with ethyl acetate. The extract was washed with a saturated aqueous solution of sodium hydrogen carbonate and a saturated aqueous solution of sodium chloride, successively, dried over anhydrous magnesium sulfate and concentrated to give the desired compound (150 mg) having the following physical data.

TLC:Rf 0.94 (hexane:ethyl acetate=3:1).

REFERENCE EXAMPLE 36

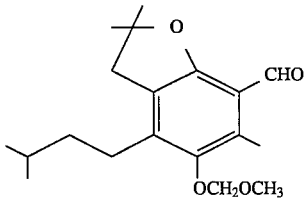

By the same procedure as reference example 15→reference example 26, using the compound prepared in reference example 35, the desired compound having the following physical data was given.

TLC:Rf 0.28 (hexane:ethyl acetate=10:1).

REFERENCE EXAMPLE 37

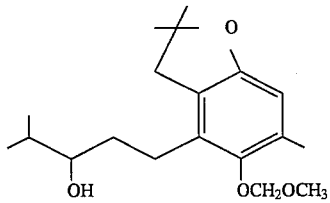

Isopropylmagnesium bromide (0.79 ml, 0.68M solution in tetrahydrofuran) was added to a solution of the compound prepared in reference example 22 (98 mg) in tetrahydrofuran (2 ml) at room temperature under an atmosphere of argon and the mixture was stirred for 15 min at room temperature. The mixture was quenched by addition of a saturated aqueous solution of ammonium chloride and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=5:1→4:1) to give the desired compound (67 mg) having the following physical data.

TLC:Rf 0.44 (hexane:ethyl acetate=2:1).

REFERENCE EXAMPLE 38

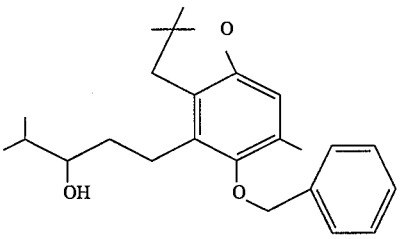

By the same procedure as reference example 33→reference example 34, using the compound prepared in reference example 37, the desired compound having the following physical data was given.

TLC:Rf 0.52 (hexane:ethyl acetate=3:1).

REFERENCE EXAMPLE 39

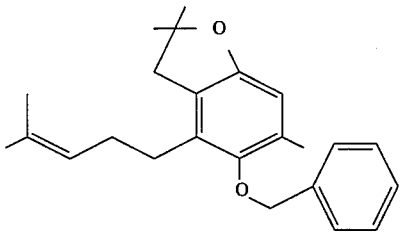

Triethylamine (0.81 ml) and mesyl chloride (0.23 ml) were added to a solution of the compound prepared in reference example 38 (713 mg) in dichloromethane (7 ml) at 0° C. under an atmosphere of argon and the mixture was stirred for 30 min. The mixture was quenched by addition of water and extracted with ethyl acetate. The extract was washed with water and a saturated aqueous solution of sodium chloride, successively, dried over anhydrous magnesium sulfate and concentrated. Sodium bromide (800 mg) was added to a solution of compound thus obtained in hexamethylphosphoramide (6 ml) under an atmosphere of argon and the mixture was stirred for 2 h at 110° C. The mixture was quenched by addition of water and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate =5:1) to give the desired compound (506 mg) having the following physical data.

TLC:Rf 0.77 (hexane:ethyl acetate=5:1).

REFERENCE EXAMPLE 40

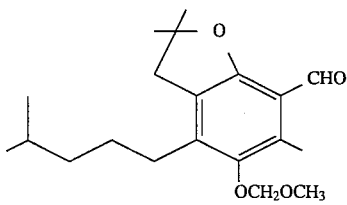

By the same procedure as reference example 15→reference example 26, using the compound prepared in reference example 39, the desired compound having the following physical data was given.

TLC:Rf 0.28 (hexane:ethyl acetate=10:1).

REFERENCE EXAMPLE 41

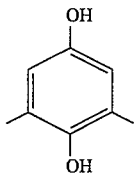

By the same procedure as reference example 1→reference example 2, using 3,5-dimethylphenol, the desired compound was given.

REFERENCE EXAMPLE 42

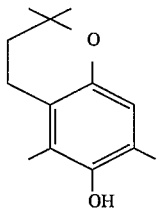

3-Methyl-2-buten-1-ol (2.7 ml) and boron trifluoride diethyl etherate (3.8 mg) were added to a solution of the compound prepared in reference example 41 (1.29 g) in dichloromethane (150 ml) and 1,2-dichloroethane (150 ml) at room temperature under an atmosphere of argon. The mixture was stirred for 18 h at room temperature. The mixture was poured into a saturated aqueous solution of sodium hydrogen carbonate and extracted with dichloromethane. The extract was washed with water and a saturated aqueous solution of sodium chloride, successively, dried over anhydrous magnesium sulfate and concentrated. The residue was purified by column chromatography on silica gel (hexane:ethyl acetate=10:1) to give the desired compound (1.92 g) having the following physical data.

TLC:Rf 0.61 (hexane:ethyl acetate=4:1).

REFERENCE EXAMPLE 43

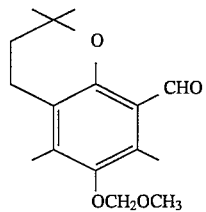

By the same procedure as reference example 9→reference example 10, using the compound prepared in reference example 42, the desired compound having the following physical data was given.

TLC:Rf 0.46 (hexane:ethyl acetate=4:1).

REFERENCE EXAMPLE 44

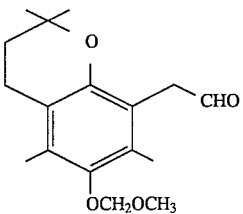

By the same procedure as reference example 23→reference example 21→reference example 22, using the compound prepared in reference example 43, the desired compound having the following physical data was given.

TLC:Rf 0.55 (hexane:ethyl acetate=4:1).

REFERENCE EXAMPLE 45

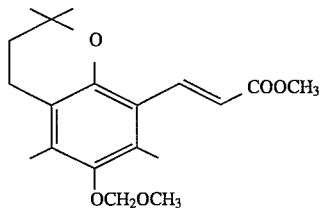

Methyl (triphenylphosphoranylidene) acetate (668 mg) was added to a solution of the compound prepared in reference example 43 (280 mg) in benzene (15 ml) under an atmosphere of argon and the mixture was stirred at 80° C. overnight. The mixture was poured into water and extracted with ethyl acetate. The extract was washed with a saturated aqueous solution of sodium chloride, dried over anhydrous magnesium sulfate and concentrated. The residue was purified by column chromatography on silica gel (hexane:ethyl acetate=10:1) to give the desired compound (304 mg) having the following physical data.

TLC:Rf 0.31 (hexane:ethyl acetate=4:1 (twice)).

REFERENCE EXAMPLE 46

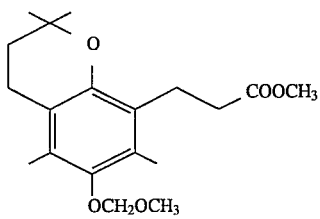

By the same procedure as reference example 15, using the compound prepared in reference example 45, the desired compound was given.

REFERENCE EXAMPLE 47

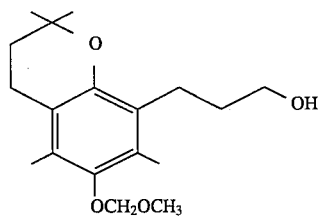

A solution of the compound prepared in reference example 46 (336 mg) in tetrahydrofuran (1.5 ml) was added to a suspension of lithium aluminum hydride (27 mg) in tetrahydrofuran (2 ml) at 0° C. under an atmosphere of argon. The mixture was stirred for 30 min at room temperature. A saturated aqueous solution of sodium sulfate was added to the reaction mixture at 0° C. The mixture was stirred for 30 min and anhydrous magnesium sulfate was added to the mixture. The mixture was filtered and the filtrate was concentrated to give the desired compound (279 mg) having the following physical data.

TLC:Rf 0.17 (hexane:ethyl acetate=4:1).

REFERENCE EXAMPLE 48

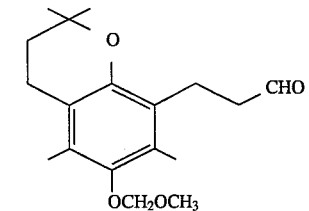

By the same procedure as reference example 22, using the compound prepared in reference example 47, the desired compound having the following physical data was given.

TLC:Rf 0.50 (hexane:ethyl acetate=4:1).

REFERENCE EXAMPLE 49

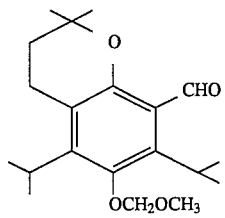

By the same procedure as reference example 41→reference example 42→reference example 43, using 2,6-diisopropylphenol, the desired compound having the following physical data was given.

TLC.:Rf 0.64 (hexane:ethyl acetate=4:1).

REFERENCE EXAMPLE 50

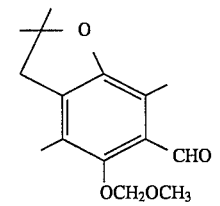

By the same procedure as reference example 1→reference example 2→reference example 5→reference example 6→reference example 7→reference example 9→reference example 10, using 2,5-dimethylphenol, the desired compound was given.

REFERENCE EXAMPLE 51

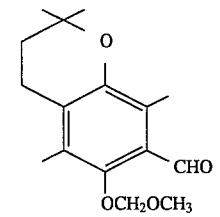

By the same procedure as reference example 49, using 2,5-dimethylphenol, the desired compound having the following physical data was given.

TLC:Rf 0.22 (hexane:ethyl acetate=10:1).

REFERENCE EXAMPLE 52

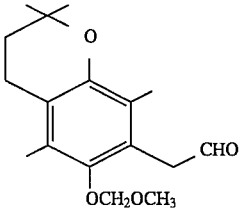

By the same procedure as reference example 44, using the compound prepared in reference example 51, the desired compound having the following physical data was given.

TLC:Rf 0.30 (hexane:ethyl acetate=10:1).

REFERENCE EXAMPLE 53

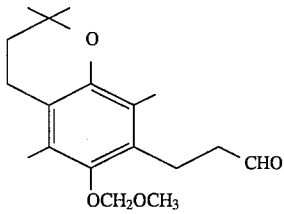

By the same procedure as reference example 45→reference example 46→reference example 47→reference example 48, using the compound prepared in reference example 51, the desired compound having the following physical data was given.

TLC:Rf 0.66 (hexane:ethyl acetate=2:1).

REFERENCE EXAMPLE 54

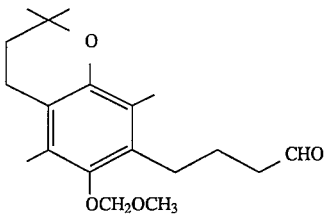

By the same procedure as reference example 44, using the compound prepared in reference example 53, the desired compound having the following physical data was given.

TLC:Rf 0.52 (hexane:ethyl acetate=4:1).

REFERENCE EXAMPLE 55

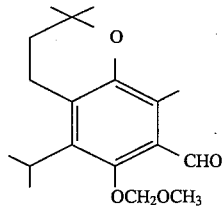

By the same procedure as reference example 49, using 2-isopropyl- 5-methylphenol, the desired compound was given.

REFERENCE EXAMPLE 56

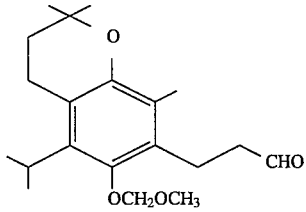

By the same procedure as reference example 53, using the compound prepared in reference example 55, the desired compound having the following physical data was given.

TLC:Rf 0.69 (hexane:ethyl acetate=2:1).

REFERENCE EXAMPLE 57

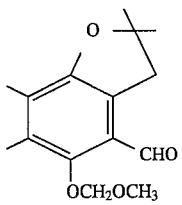

By the same procedure as reference example 50, using 2,3-dimethylphenol, the desired compound having the following physical data was given.

TLC:Rf 0.30 (hexane:ethyl acetate=9:1).

REFERENCE EXAMPLE 58

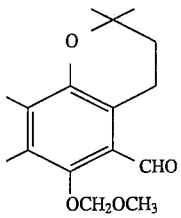

By the same procedure as reference example 49, using 2,3-dimethylphenol, the desired compound was given.

REFERENCE EXAMPLE 59

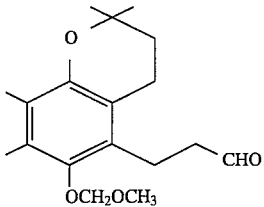

By the same procedure as reference example 53, using the compound prepared in reference example 58, the desired compound having the following physical data was given.

TLC:Rf 0.69 (hexane:ethyl acetate=2:1).

REFERENCE EXAMPLE 60

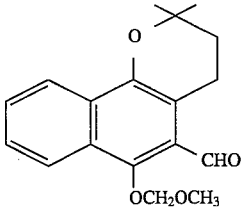

By the same procedure as reference example 2→reference example 42→reference example 43, using 1,4-naphthoquinone, the desired compound having the following physical data was given.

TLC:Rf 0.53 (hexane:ethyl acetate=4:1).

REFERENCE EXAMPLE 61

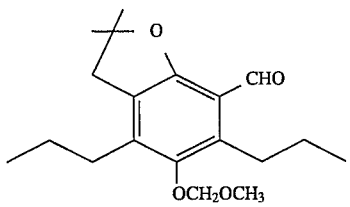

By the same procedure as reference example 13→reference example 6→reference example 13→reference example 6→reference example 15→reference example 3→reference example 4→reference example 5→reference example 6→reference example 7→reference example 8→reference example 9→reference example 10, using 4-benzyloxyphenol, the desired compound having the following physical data was given.

TLC:Rf 0.24 (hexane:ethyl acetate=19:1).

REFERENCE EXAMPLE 62

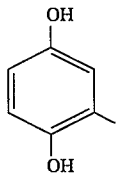

By the same procedure as reference example 1→reference example 2, using 2-methylphenol, the desired compound having the following physical data was given.

TLC:Rf 0.10 (hexane:ethyl acetate=4:1).

REFERENCE EXAMPLE 63

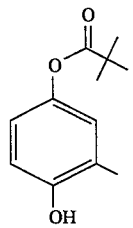

Pyridine (16 ml) and pivaloyl chloride (12.3 ml) were added to a solution of the compound prepared in reference example 62 (12.4 g) in dichloromethane (70 ml) at 0° C. under an atmosphere of argon and the mixture was stirred for 1.5 h at room temperature. The mixture was quenched by addition of water and extracted with diethyl ether. The extract was washed with 2N aqueous solution of hydrochloric acid, water, a saturated aqueous solution of sodium hydrogen carbonate, water and a saturated aqueous solution of sodium chloride, successively, dried over anhydrous magnesium sulfate and concentrated. The residue was purified by column chromatography on silica gel (hexane:ethyl acetate=9:1) to give the desired compound (12.3 g) having the following physical data.

TLC:Rf 0.40 (hexane:ethyl acetate=4:1).

REFERENCE EXAMPLE 64

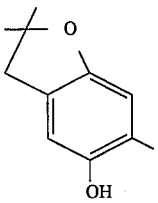

By the same procedure as reference example 10→reference example 8→reference example 5→reference example 6→reference example 25→reference example 7, using the compound prepared in reference example 63, the desired compound having the following physical data was given.

TLC:Rf 0.50 (hexane:ethyl acetate=2:1).

REFERENCE EXAMPLE 65

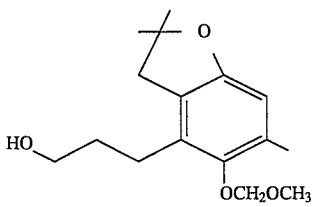

By the same procedure as reference example 13→reference example 6→reference example 10→reference example 21, using the compound prepared in reference example 64, the desired compound having the following physical data was given.

TLC:Rf 0.13 (hexane:ethyl acetate=4:1).

REFERENCE EXAMPLE 66

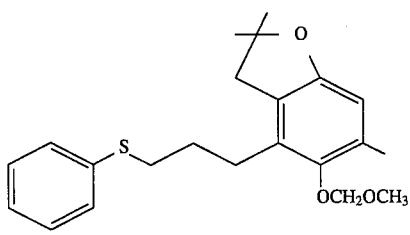

Triethylamine (0.69 ml) and mesyl chloride (0.29 ml) were added to a solution of the compound prepared in reference example 65 (695 mg) in dichloromethane (10 ml) at −20° C. under an atmosphere of argon and the mixture was stirred for 20 min at same temperature. The mixture was quenched by addition of ice water and extracted with ethyl acetate. The extract was washed with 1N aqueous solution of hydrochloric acid, water, a saturated aqueous solution of sodium hydrogen carbonate, water and a saturated aqueous solution of sodium chloride, successively, dried over anhydrous sodium sulfate and concentrated. Thiophenol (0.31 ml) and potassium carbonate (51 5 mg) were added to a solution of the residue thus obtained in dimethylformamide (10 ml) at room temperature, successively, and the mixture was stirred for 3 h at room temperature and 1 h at 60° C. The mixture was cooled to room temperature, poured into ice water and extracted with diethyl ether. The extract was washed with a saturated aqueous solution of sodium chloride, dried over anhydrous magnesium sulfate and concentrated. The residue was purified by column chromatography on silica gel (hexane:ethyl acetate=19:1) to give the desired compound (661 mg) having the following physical data.

TLC:Rf 0.61 (hexane:ethyl acetate=4:1).

REFERENCE EXAMPLE 67

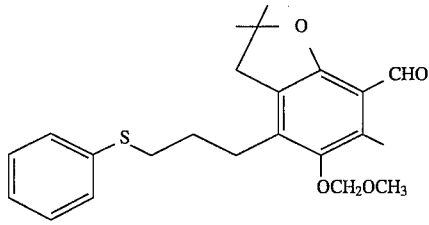

By the same procedure as reference example 25→reference example 26, using the compound prepared in reference example 66, the desired compound having the following physical data was given.

TLC:Rf 0.50 (hexane:ethyl acetate=4:1).

REFERENCE EXAMPLE 68

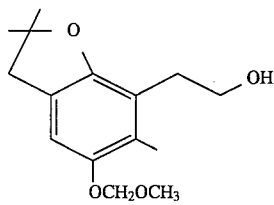

By the same procedure as reference example 26→reference example 23→reference example 21, using the compound prepared in reference example 64, the desired compound having the following physical data was given.

TLC:Rf 0.40 (hexane:ethyl acetate=2:1).

REFERENCE EXAMPLE 69

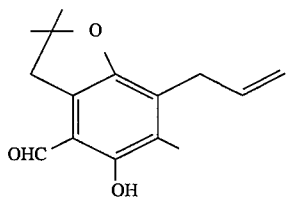

By the same procedure as reference example 22→reference example 23→reference example 25→reference example 9, using the compound prepared in reference example 68, the desired compound having the following physical data was given.

TLC:Rf 0.40 (hexane:ethyl acetate=10:1).

REFERENCE EXAMPLE 70

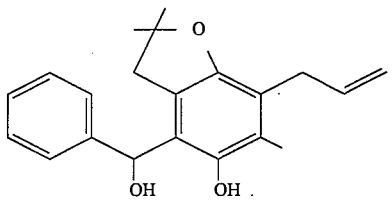

Phenylmagnesium bromide (0.55 ml, 3M solution in diethyl ether) was added to a solution of the compound prepared in reference example 69 (100 mg) in diethyl ether (2 ml) at 0° C. under an atmosphere of argon and the mixture was stirred for 15 min at room temperature. The mixture was quenched by addition of a saturated aqueous solution of ammonium chloride and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate =10:1) to give the desired compound (115 mg) having the following physical data.

TLC:Rf 0.15 (hexane:ethyl acetate=10:1).

REFERENCE EXAMPLE 71

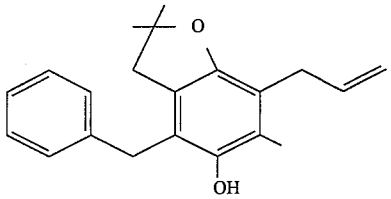

Triethylsilane (0.17 ml) and trifluoroacetic acid (0.7 ml) were added to a solution of the compound prepared in reference example 70 (115 mg) in dichloromethane (2 ml) at room temperature under an atmosphere of argon and the mixture was stirred for 1 h at room temperature. The mixture was quenched by addition of water and extracted with ethyl acetate. The extract was washed with water, a saturated aqueous solution of sodium hydrogen carbonate, water and a saturated aqueous solution of sodium chloride, successively, dried over anhydrous magnesium sulfate and concentrated. Tetrabutylammonium fluoride (0.34 ml, 1N solution in tetrahydrofuran) was added to a solution of the residue thus obtained in tetrahydrofuran (2 ml) at room temperature under an atmosphere of argon and the mixture was stirred for 2 days at room temperature. The mixture was quenched by addition of water and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=15:1) to give the desired compound (89 mg) having the following physical data.

TLC:Rf 0.34 (hexane:ethyl acetate=10:1).

REFERENCE EXAMPLE 72

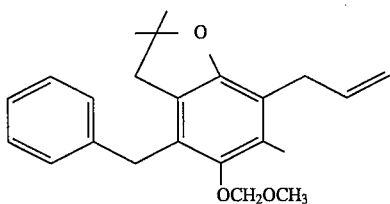

By the same procedure as reference example 10, using the compound prepared in reference example 71, the desired compound having the following physical data was given.

TLC:Rf 0.34 (hexane:ethyl acetate=10:1).

REFERENCE EXAMPLE 73

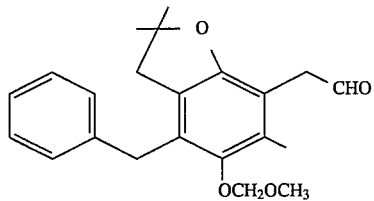

Osmium tetroxide (1 ml, 4 wt % aqueous solution) was added to a solution of the compound prepared in reference example 72 (224 mg) in dioxane (3 ml) and water (1 ml) at room temperature and the mixture was stirred for 15 min. Sodium metaperiodate (613 mg) was added to the reaction mixture and the mixture was stirred for 3 h at room temperature. The mixture was extracted with diethyl ether. The extract was washed with a saturated aqueous solution of sodium chloride, dried over anhydrous sodium sulfate and concentrated to give the desired compound (226 mg) having the following physical data.

TLC:Rf 0.44 (hexane:ethyl acetate=4:1).

REFERENCE EXAMPLE 74

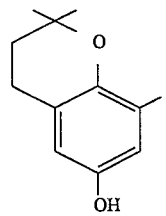

By the same procedure as reference example 42→reference example 47, using the compound prepared in reference example 63, the desired compound having the following physical data was given.

TLC:Rf 0.26 (hexane:ethyl acetate=4:1).

REFERENCE EXAMPLE 75

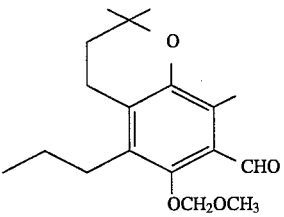

By the same procedure as reference example 13→reference example 6→reference example 15→reference example 9→reference example 10, using the compound prepared in reference example 74, the desired compound was given.

REFERENCE EXAMPLE 76

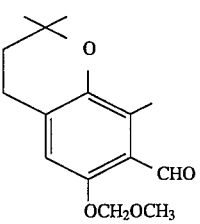

By the same procedure as reference example 9→reference example 10, using the compound prepared in reference example 74, the desired compound was given.

REFERENCE EXAMPLE 77

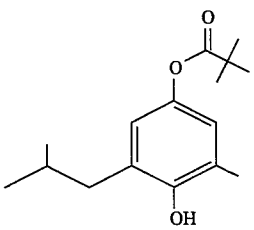

By the same procedure as reference example 62→reference example 63, using 2-isobutyl-6-methylphenol, the desired compound having the following physical data was given.

TLC:Rf 0.24 (hexane:ethyl acetate=9:1).

REFERENCE EXAMPLE 78

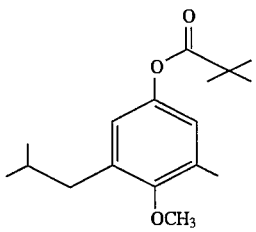

Sodium hydride (817 mg, 60% content) was added to a solution of the compound prepared in reference example 77 (5.36 g) in dimethylformamide (60 ml) at 0° C. under an atmosphere of argon. The mixture was stirred for 20 min at same temperature and for 30 min at room temperature.

Methyl iodide (1.7 ml) was added to the mixture at 0° C. The mixture was stirred for 40 min at room temperature, quenched by addition of ice water and extracted with diethyl ether. The extract was washed with water and a saturated aqueous solution of sodium chloride, successively, dried over anhydrous magnesium sulfate and concentrated. The residue was purified by column chromatography on silica gel (hexane:ethyl acetate =97:3) to give the desired compound (5.43 g) having the following physical data.

TLC:Rf 0.34 (hexane:ethyl acetate=9:1).

REFERENCE EXAMPLE 79

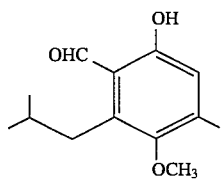

By the same procedure as reference example 9→reference example 8, using the compound prepared in reference example 78, the desired compound having the following physical data was given.

TLC:Rf 0.54 (hexane:ethyl acetate=17:3).

REFERENCE EXAMPLE 80

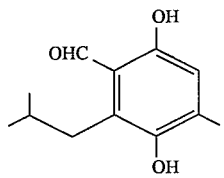

Boron tribromide (8.4 ml, 1M solution in dichloromethane) was added to a solution of the compound prepared in reference example 79 (621 mg) in dichloromethane (14 ml) at 0° C. and the mixture was stirred for 15 min at same temperature. The mixture was quenched by addition of ice water and extracted with ethyl acetate. The extract was washed with water and a saturated aqueous solution of sodium chloride, successively, dried over anhydrous magnesium sulfate and concentrated to give the desired compound having the following physical data.

TLC:Rf 0.17 (hexane:ethyl acetate=9:1).

REFERENCE EXAMPLE 81

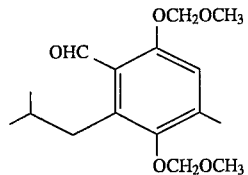

By the same procedure as reference example 10, using the compound prepared in reference example 80, the desired compound having the following physical data was given.

TLC:Rf 0.19 (hexane:ethyl acetate=9:1).

REFERENCE EXAMPLE 82

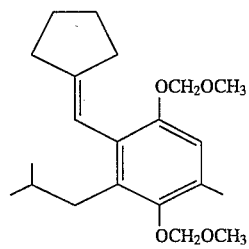

A suspension of sodium hydride (225 mg) in dimethylsulfoxide (4 ml) for 1 h at 70° C. The suspension was cooled to room temperature. A suspension of cyclopentyltriphenylphosphonium bromide (2.36 g) in dimethylsulfoxide (5 ml) was added to the mixture. After the mixture was stirred for 20 min at room temperature, a solution of the compound prepared in reference example 81 (763 mg) in dimethylsulfoxide (4 ml) was added to the mixture. The mixture was stirred for 20 min at room temperature, poured into ice water and extracted with diethyl ether. The extract was washed with water and a saturated aqueous solution of sodium chloride, successively, dried over anhydrous magnesium sulfate and concentrated. The residue was purified by column chromatography on silica gel (hexane:ethyl acetate =9:1) to give the desired compound (404 mg) having the following physical data.

TLC:Rf 0.48 (hexane:ethyl acetate=17:3).

REFERENCE EXAMPLE 83

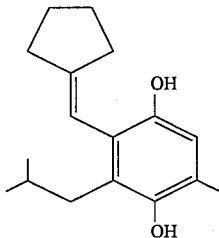

By the same procedure as reference example 25, using the compound prepared in reference example 82, the desired compound having the following physical data was given.

TLC:Rf 0.32 (hexane:ethyl acetate=17:3).

REFERENCE EXAMPLE 84

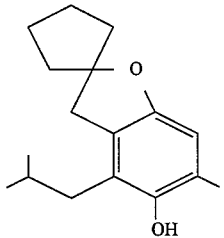

Boron trifluoride diethyl etherate (0.42 ml) was added to a solution of the compound prepared in reference example 83 (322 mg) in dichloromethane (6 ml) at 0° C. and the mixture was stirred for 1 h at room temperature. The mixture was quenched by addition of ice water and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=23:2) to give the desired compound (277 mg) having the following physical data.

TLC:Rf 0.41 (hexane:ethyl acetate=17:3).

REFERENCE EXAMPLE 85

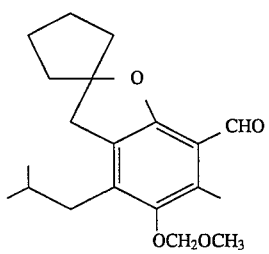

By the same procedure as reference example 9→reference example 10, using the compound prepared in reference example 84, the desired compound having the following physical data was given.

TLC:Rf 0.38 (hexane:ethyl acetate=17:3).

REFERENCE EXAMPLE 86

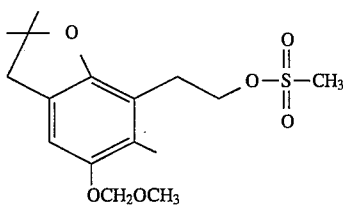

Triethylamine (0.39 ml) and mesyl chloride (0.11 ml) were added to a solution of the compound prepared in reference example 68 (250 mg) in dichloromethane (4 ml) at 0° C. under an atmosphere of argon, successively, and the mixture was stirred for 30 min at 0° C. The mixture was quenched by addition of water and extracted with ethyl acetate. The extract was washed with water and a saturated aqueous solution of sodium chloride, successively, dried over anhydrous magnesium sulfate and concentrated to give the desired compound (345 mg) having the following physical data.

TLC:Rf 0.39 (hexane:ethyl acetate=2:1).

REFERENCE EXAMPLE 87

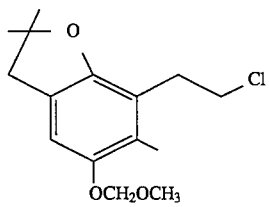

Lithium chloride (80 mg) was added to a solution of the compound prepared in reference example 86 (345 mg) in dimethylformamide (2 ml) under an atmosphere of argon and the mixture was stirred at 80° C. overnight. The mixture was quenched by addition of water and extracted with ethyl acetate. The extract was washed with water and a saturated aqueous solution of sodium chloride, successively, dried over anhydrous magnesium sulfate and concentrated to give the desired compound (267 mg) having the following physical data.

TLC:Rf 0.67 (hexane:ethyl acetate=5:1).

REFERENCE EXAMPLE 88

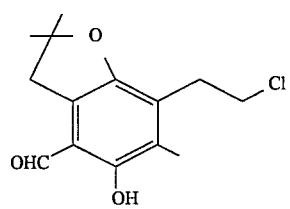

By the same procedure as reference example 25→reference example 9, using the compound prepared in reference example 87, the desired compound having the following physical data was given.

TLC:Rf 0.69 (hexane:ethyl acetate=4:1).

REFERENCE EXAMPLE 89

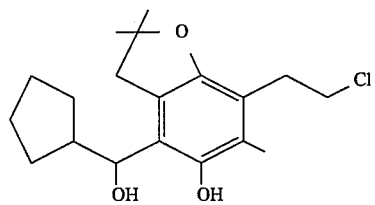

Cyclopentylmagnesium chloride (2 ml, 2M solution in diethyl ether) was added to a solution of the compound prepared in reference example 88 (200 mg) in tetrahydrofuran (2 ml) at 0° C. under an atmosphere of argon and the mixture was stirred for 15 min at room temperature. The mixture was quenched by addition of a saturated aqueous solution of ammonium chloride and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate =15:1→10:1) to give the desired compound (193 mg) having the following physical data.

TLC:Rf 0.28 (hexane:ethyl acetate=4:1).

REFERENCE EXAMPLE 90

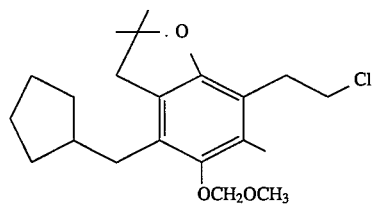

By the same procedure as reference example 71→reference example 10, using the compound prepared in reference example 89, the desired compound having the following physical data was given.

TLC:Rf 0.69 (hexane:ethyl acetate=10:1).

REFERENCE EXAMPLE 91

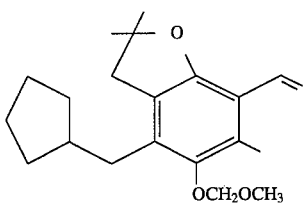

A mixture of the compound prepared in reference example 90 (185 mg) and 1,8-diazabicyclo[5.4.0]undec-7-ene (0.8 ml) was stirred for 1 day at 70° C. under an atmosphere of argon. The mixture was quenched by addition of water and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=15:1) to give the desired compound (125 mg) having the following physical data.

TLC:Rf 0.71 (hexane:ethyl acetate=10:1).

REFERENCE EXAMPLE 92

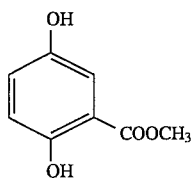

A saturated solution of hydrogen chloride in methanol (15 ml) was added to a solution of 2,5-dihydroxybenzoic acid (2 g) in methanol (10 ml) at room temperature and the mixture was stirred at room temperature overnight. The mixture was concentrated and sodium hydrogen carbonate was added to the mixture until basic solution. The mixture was extracted with ethyl acetate. The extract was washed with a saturated aqueous solution of sodium hydrogen carbonate and a saturated aqueous solution of sodium chloride, successively, dried over anhydrous magnesium sulfate and concentrated to give the desired compound (1.93 g) having the following physical data.

TLC:Rf 0.28 (hexane:ethyl acetate=4:1).

REFERENCE EXAMPLE 93

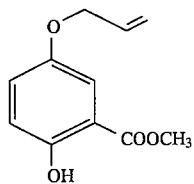

Potassium carbonate (1.74 g) and allyl bromide (1.0 ml) were added to a solution of the compound prepared in reference example 92 (1.93 g) in dimethylformamide (10 ml) under an atmosphere of argon, successively, and the mixture was stirred for 2 h at 40° C. The mixture was quenched by addition of water and extracted with ethyl acetate. The extract was washed with water and a saturated aqueous solution of sodium chloride, successively, dried over anhydrous magnesium sulfate and concentrated. The residue was purified by column chromatography on silica gel (hexane: ethyl acetate=8:1) to give the desired compound (1.2 g) having the following physical data.

TLC:Rf 0.46 (hexane:ethyl acetate=4:1).

REFERENCE EXAMPLE 94

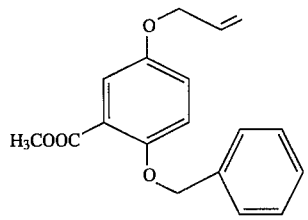

Sodium hydride (635 mg, 60% content) was added to a solution of the compound prepared in reference example 93 (3.0 g) in dimethylformamide (15 ml) at 0° C. under an atmosphere of argon and the mixture was stirred for 30 min at room temperature. Benzyl bromide (1.9 ml) was added to the mixture at room temperature and the mixture was stirred for 30 min at room temperature. The mixture was poured into water and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=10:1) to give the desired compound (4.30 g) having the following physical data.

TLC:Rf 0.44 (hexane:ethyl acetate=4:1).

REFERENCE EXAMPLE 95

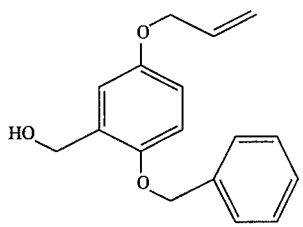

By the same procedure as reference example 47, using the compound prepared in reference example 94, the desired compound having the following physical data was given.

TLC:Rf 0.30 (hexane:ethyl acetate=4:1),

REFERENCE EXAMPLE 96

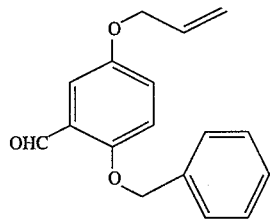

Pyridium chlorochromate (5.6 g) and anhydrous magnesium sulfate (14 g) were added to a solution of the compound prepared in reference example 95 (3.54 g) in dichloromethane (140 ml) at 0° C. under an atmosphere of argon and the mixture was stirred for 30 min at room temperature. The mixture was concentrated and diethyl ether was added to the residue. The mixture was filtered through Celite (being on sale) and the filtrate was concentrated. The residue was purified by column chromatography on silica gel (hexane:ethyl acetate=4:1) to give the desired compound (3.16 g) having the following physical data.

TLC:Rf 0.45 (hexane:ethyl acetate=4:1).

REFERENCE EXAMPLE 97

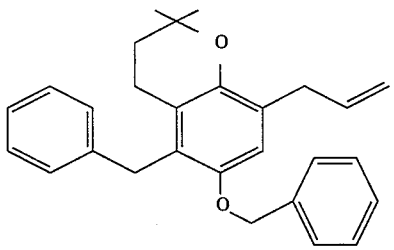

By the same procedure as reference example 70→reference example 71→reference example 6→reference example 42, using the compound prepared in reference example 96, the desired compound having the following physical data was given.

TLC:Rf 0.34 (hexane:ethyl acetate=10:1).

REFERENCE EXAMPLE 98

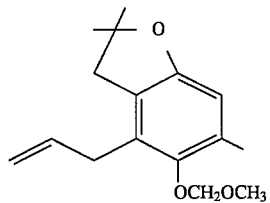

By the same procedure as reference example 8→reference example 10, using the compound A prepared in reference example 14, the desired compound having the following physical data was given.

TLC:Rf 0.33 (hexane:ethyl acetate=19:1).

REFERENCE EXAMPLE 99

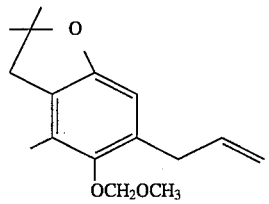

By the same procedure as reference example 98, using the compound B prepared in reference example 14, the desired compound having the following physical data was given.

TLC:Rf 0.32 (hexane:ethyl acetate=19:1).

REFERENCE EXAMPLE 100

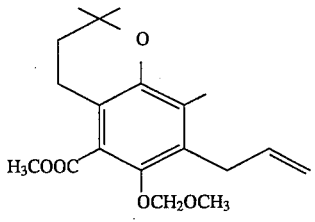

By the same procedure as reference example 9→reference example 13→reference example 31→reference example 6→reference example 10, using the compound prepared in reference example 74, the desired compound having the following physical data was given.

TLC:Rf 0.17 (hexane:ethyl acetate=9:1).

REFERENCE EXAMPLE 101

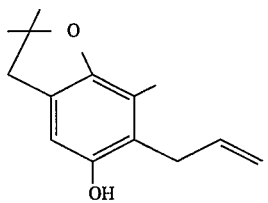

By the same procedure as reference example 5→reference example 6→reference example 7→reference example 47→reference example 13 →reference example 6, using the compound prepared in reference example 63, the desired compound having the following physical data was given.

TLC:Rf 0.15 (hexane:ethyl acetate=10:1).

REFERENCE EXAMPLE 102

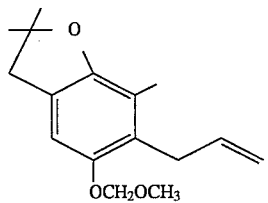

By the same procedure as reference example 10, using the compound prepared in reference example 101, the desired compound having the following physical data was given.

TLC:Rf 0.48 (hexane:ethyl acetate=30:1).

REFERENCE EXAMPLE 103

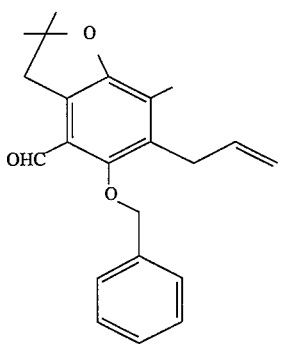

By the same procedure as reference example 9→reference example 94, using the compound prepared in reference example 101, the desired compound having the following physical data was given.

TLC:Rf 0.52 (hexane:ethyl acetate=5:1).

REFERENCE EXAMPLE 104

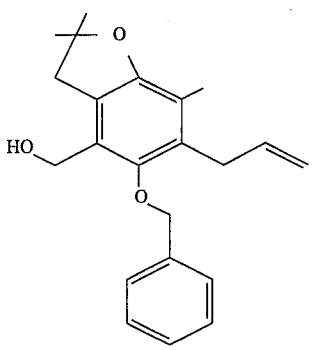

Sodium borohydride (96 mg) and methanol (2 ml) were added to a solution of the compound prepared in reference example 103 (850 mg) in dichloromethane (4 ml) at 0° C. and the mixture was stirred for 30 min at same temperature. The mixture was quenched by addition of a saturated aqueous solution of ammonium chloride and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=5:1) to give the desired compound (743 mg) having the following physical data.

TLC:Rf 0.21 (hexane:ethyl acetate=5:1).

REFERENCE EXAMPLE 105

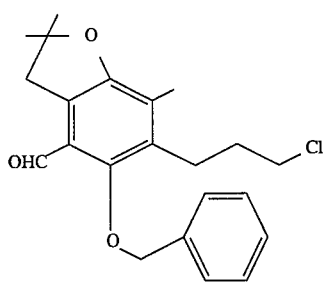

By the same procedure as reference example 10→reference example 21→reference example 86→reference example 87→reference example 25→reference example 96, using the compound prepared in reference example 104, the desired compound having the following physical data was given.

TLC:Rf 0.58 (hexane:ethyl acetate=5:1).

REFERENCE EXAMPLE 106

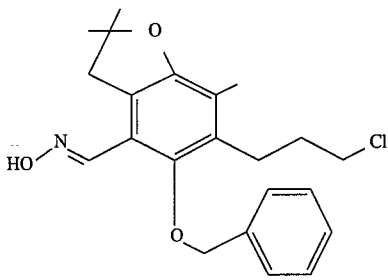

Hydroxylamine hydrochloride (53 mg) was added to a solution of the compound prepared in reference example 105 (140 mg) in pyridine (1 ml) at room temperature and the mixture was stirred at room temperature overnight. The mixture was quenched by addition of water and extracted with ethyl acetate. The extract was washed with 1N aqueous solution of hydrochloric acid, water, a saturated aqueous solution of sodium hydrogen carbonate and a saturated aqueous solution of sodium chloride, successively, dried over anhydrous magnesium sulfate and concentrated to give the desired compound (126 mg) having the following physical data.

TLC:Rf 0.30 (hexane:ethyl acetate=5:1).

REFERENCE EXAMPLE 107

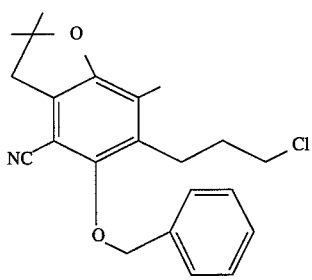

Thionyl chloride (0.15 ml) was added to a solution of the compound prepared in reference example 106 (126 mg) in diethyl ether (5 ml) and the mixture was stirred for 2 h at room temperature. The mixture was quenched by addition of water and extracted with ethyl acetate. The extract was washed with water, a saturated aqueous solution of sodium hydrogen carbonate and a saturated aqueous solution of sodium chloride, successively, dried over anhydrous magnesium sulfate and concentrated. The residue was purified by column chromatography on silica gel (hexane:ethyl acetate=10:1) to give the desired compound (110 mg) having the following physical data.

TLC:Rf 0.50 (hexane:ethyl acetate=5:1).

REFERENCE EXAMPLE 108

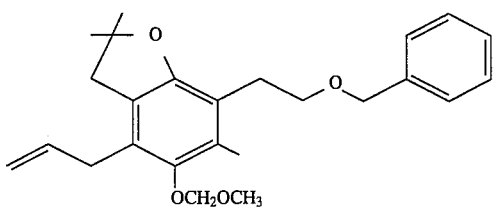

By the same procedure as reference example 94→reference example 25→reference example 13→reference example 6→reference example 10, using the compound prepared in reference example 68, the desired compound having the following physical data was given.

TLC:Rf 0.55 (hexane:ethyl acetate=5:1).

REFERENCE EXAMPLE 109

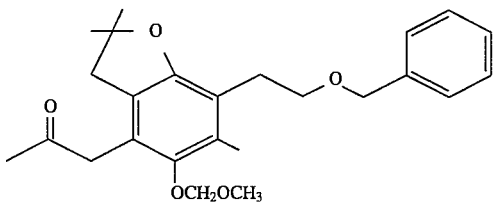

Copper chloride (CuCl) (65 mg) was added to a solution of palladium chloride (PdCl$_2$) (12 mg) in dimethylformamide (1 ml) and water (0.2 ml) under an atmosphere of oxygen and the mixture was stirred for 30 min at room temperature. A solution of the compound prepared in reference example 108 (262. mg) in dimethylformamide (1.5 ml) was added to the mixture. The mixture was stirred at room temperature under an atmosphere of oxygen overnight. The mixture was quenched by addition of water and extracted with a mixture of hexane and ethyl acetate (1:1). The extract was washed with water and a saturated aqueous solution of sodium chloride, successively, dried over anhydrous magnesium sulfate and concentrated. The residue was purified by column chromatography on silica gel (hexane:ethyl acetate=5:1) to give the desired compound (233 mg) having the following physical data.

TLC:Rf 0.25 (hexane:ethyl acetate=5:1).

REFERENCE EXAMPLE 110

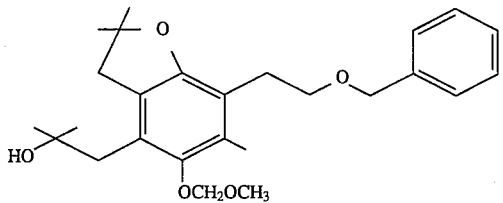

Methylmagnesium bromide (1.5 ml, 1M solution in tetrahydrofuran) was added to a solution, of the compound prepared in reference example 109 (233 mg) in tetrahydrofuran (2 ml) at 0° C. under an atmosphere of argon and the mixture was stirred for 15 min at room temperature. The mixture was quenched by addition of a saturated aqueous solution of ammonium chloride and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate =5:1) to give the desired compound (227 mg) having the following physical data.

TLC:Rf 0.15 (hexane:ethyl acetate=5:1 (twice)).

REFERENCE EXAMPLE 111

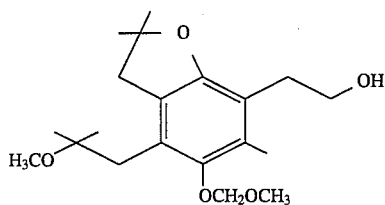

By the same procedure as reference example 78→reference example 15, using the compound prepared in reference example 110, the desired compound having the following physical data was given.

TLC:Rf 0.16 (hexane:ethyl acetate=4:1).

REFERENCE EXAMPLE 112

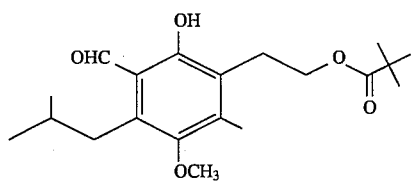

By the same procedure as reference example 9→reference example 8→reference example 94→reference example 23→reference example 21→reference example 63→reference example 15→reference example 9, using the compound prepared in reference example 78, the desired compound having the following physical data was given.

TLC:Rf 0.43 (hexane:ethyl acetate=9:1).

REFERENCE EXAMPLE 113

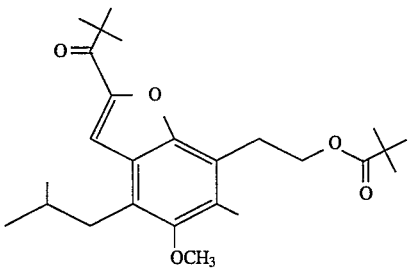

A suspension of the compound prepared in reference example 112 (380 mg), 1-chloropinacolone (219 mg) and potassium carbonate (450 mg) in ethanol (5.4 ml) was stirred for 20 min at 100° C. The mixture was cooled to room temperature and concentrated. The residue was diluted with diethyl ether, washed with water and a saturated aqueous solution of sodium chloride, successively, dried over anhydrous magnesium sulfate and concentrated. The residue was purified by column chromatography on silica gel (hexane:ethyl acetate=97:3→19:1) to give the desired compound (457 mg) having the following physical data.

TLC:Rf 0.53 (hexane:ethyl acetate=9:1).

REFERENCE EXAMPLE 114

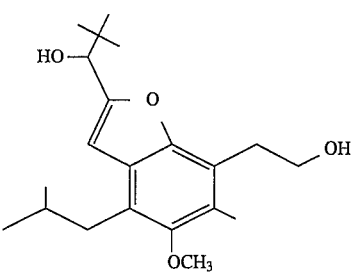

Diisobutylaluminium hydride (2.3 ml, 1.5M solution in toluene) was added to a solution of the compound prepared in reference example 113 (454 mg) in dichloromethane (5 ml) at −70° C. and the mixture was stirred for 10 min. The mixture was stirred for 15 min at 0° C. and methanol (0.5 ml) was added to the mixture. The mixture was quenched by addition of 2N aqueous solution of hydrochloric acid and water. The mixture was extracted with ethyl acetate. The extract was washed with water, a saturated aqueous solution of sodium hydrogen carbonate, water and a saturated aqueous solution of sodium chloride, successively, dried over anhydrous magnesium sulfate and concentrated. The residue was purified by column chromatography on silica gel (hexane:ethyl acetate=3:2) to give the desired compound (353 mg) having the following physical data.

TLC:Rf 0.43 (hexane:ethyl acetate=1:1).

REFERENCE EXAMPLE 115

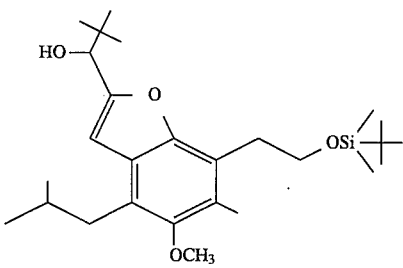

tert-Butyldimethylsilyl chloride (167 mg) and dimethylaminopyridine (6 mg) were added to a solution of the compound prepared in reference example 114 (350 mg) and triethylamine (0.17 ml) in dichloromethane (5 ml) and the mixture was stirred for 4 h at room temperature. The mixture was quenched by addition of 2N aqueous solution of hydrochloric acid and ice and extracted with ethyl acetate. The extract was washed with water, a saturated aqueous solution of sodium hydrogen carbonate, water and a saturated aqueous solution of sodium chloride, successively, dried over anhydrous magnesium sulfate and concentrated. The residue was purified by column chromatography on silica gel (hexane:ethyl acetate=9:1) to give the desired compound (410 mg) having the following physical data.

TLC:Rf 0.57 (hexane:ethyl acetate=4:1).

REFERENCE EXAMPLE 116

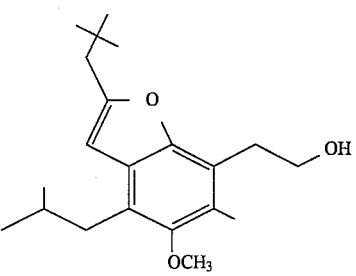

Sodium iodide (523 mg) was added to a solution of the compound prepared in reference example 115 (404 mg) in acetonitrile (4.4 ml) at 0° C. Under stirring the mixture vigorously, trimethylsilyl chloride (0.45 ml) was added to the mixture at same temperature. After the mixture was stirred for 30 min at 0° C. and ice was added to the mixture. A saturated aqueous solution of sodium thiosulfate was added to the mixture. The mixture was extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=9:1→17:3→7:3) to give the desired compound (227 mg) having the following physical data.

TLC:Rf 0.44 (hexane:ethyl acetate=7:3).

REFERENCE EXAMPLE 117

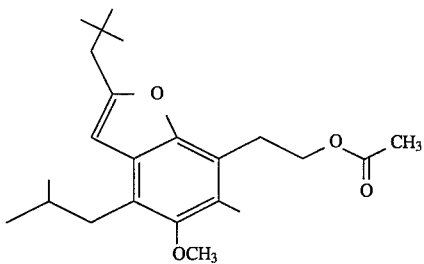

Acetyl chloride (0.03 ml) was added to a solution of the compound prepared in reference example 116 (117 mg) and triethylamine (0.15 ml) in dichloromethane (1.8 ml) at 0° C. and the mixture was stirred for 20 min at room temperature. The mixture was diluted with ethyl acetate, washed with 2N aqueous solution of hydrochloric acid, water, a saturated aqueous solution of sodium hydrogen carbonate, water and a saturated aqueous solution of sodium chloride, successively, dried over anhydrous magnesium sulfate and concentrated. The residue was purified by column chromatography on silica gel (hexane:ethyl acetate=19:1) to give the desired compound (98 mg) having the following physical data.

TLC:Rf 0.59 (hexane:ethyl acetate=4:1).

REFERENCE EXAMPLE 118

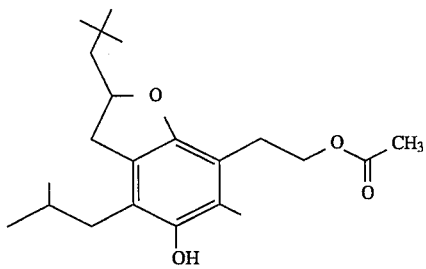

By the same procedure as reference example 80→reference example 15, using the compound prepared in reference example 117, the desired compound having the following physical data was given.

TLC:Rf 0.33 (benzene:ethyl acetate=19:1).

REFERENCE EXAMPLE 119

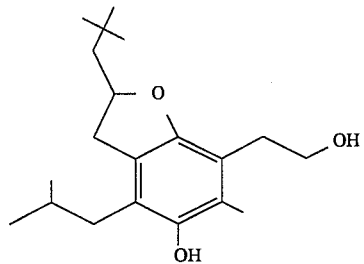

Potassium carbonate (85 mg) was added to a solution of the compound prepared in reference example 118 (74 mg) in methanol (2 ml) and the mixture was stirred for 1 h at room temperature. The mixture was poured into ice and 2N aqueous solution of hydrochloric acid. The mixture was extracted with ethyl acetate. The extract was washed with water and a saturated aqueous solution of sodium chloride, successively, dried over anhydrous magnesium sulfate and concentrated to give the desired compound (68 mg) having the following physical data.

TLC:Rf 0.25 (hexane:ethyl acetate=7:3).

REFERENCE EXAMPLE 120

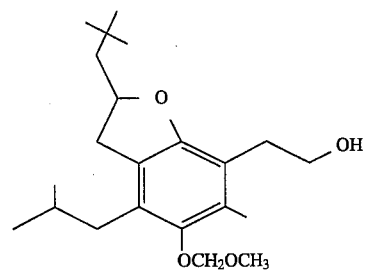

By the same procedure as reference example 10, using the compound prepared in reference example 119, the desired compound having the following physical data was given.

TLC:Rf 0.39 (hexane:ethyl acetate=7:3).

REFERENCE EXAMPLE 121

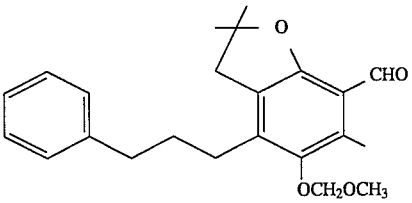

By the same procedure as reference example 70→reference example 86→reference example 91→reference example 15→reference example 25→reference example 9→reference example 10, using the compound prepared in reference example 22, the desired compound having the following physical data was given.

TLC:Rf 0.39 (hexane:ethyl acetate=4:1).

REFERENCE EXAMPLE 122

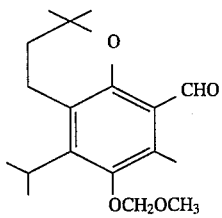

By the same procedure as reference example 42→reference example 8→reference example 9→reference example 10, using the compound prepared in reference example 4, the desired compound having the following physical data was given.

TLC:Rf 0.41 (hexane:ethyl acetate=5:1).

REFERENCE EXAMPLE 123

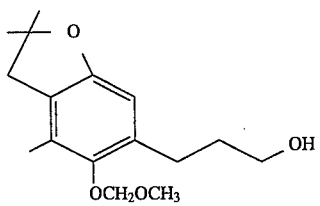

By the same procedure as reference example 8→reference example 10→reference example 21, using the compound B prepared in reference example 14, the desired compound having the following physical data was given.

TLC:Rf 0.20 (hexane:ethyl acetate=2:1).

REFERENCE EXAMPLE 124

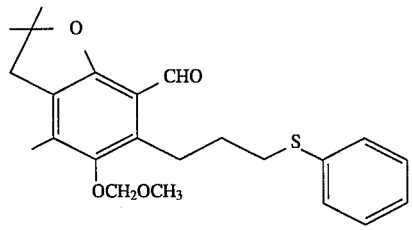

By the same procedure as reference example 66→reference example 25→reference example 9→reference example 10, using the compound prepared in reference example 123, the desired compound having the following physical data was given.

TLC:Rf 0.45 (hexane:ethyl acetate=4:1).

REFERENCE EXAMPLE 125

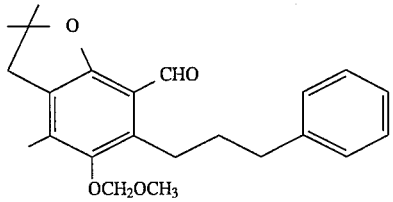

By the same procedure as reference example 22→reference example 121, using the compound prepared in reference example 123, the desired compound having the following physical data was given.

TLC:Rf 0.50 (hexane:ethyl acetate=4:1).

REFERENCE EXAMPLE 126

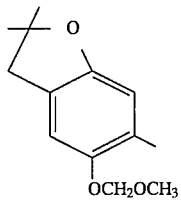

By the same procedure as reference example 10, using the compound prepared in reference example 64, the desired compound having the following physical data was given.

TLC:Rf 0.67 (hexane:ethyl acetate=5:1).

REFERENCE EXAMPLE 127

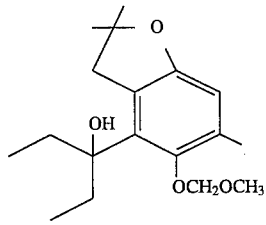

Tetramethylethylenediamine (0.96 ml) was added to a solution of the compound prepared in reference example 126 (1.17 g) in xylene (9 ml) under an atmosphere of argon and the mixture was cooled to 0° C. n-Butyllithium (4.0 ml, 1.6M solution in hexane) was added dropwise to the mixture. The mixture was stirred for 1 h at 0° C. 3-Pentanone (0.75 ml) was added dropwise to the mixture. The mixture was stirred for 1 h at 0° C. and quenched by addition of water. The water layer was acidified by adding 2N aqueous solution of hydrochloric acid. The mixture was extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=20:1→10:1) to give the desired compound (854 mg) having the following physical data.

TLC:Rf 0.40 (hexane:ethyl acetate=10:1).

REFERENCE EXAMPLE 128

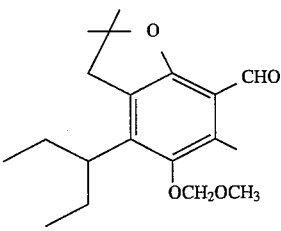

By the same procedure as reference example 71→reference example 25→reference example 15→reference example 9→reference example 10, using the compound prepared in reference example 127, the desired compound having the following physical data was given.

TLC:Rf 0.67 (hexane:ethyl acetate=4:1).

REFERENCE EXAMPLE 129

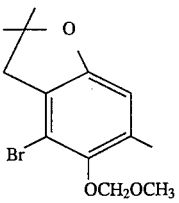

A small amount of o-phenanthroline (indicator) was added to a solution of the compound prepared in reference example 126 (5.43 g) and tetramethylethylenediamine (4.0 ml) in diethyl ether (50 ml). n-Butyllithium (16.5 ml, 1.6M solution in hexane) was added dropwise to the mixture at 0° C. The mixture was stirred for 45 min at 0° C. and cooled to −70° C. Ethyl α-bromoisobutyrate (4.3 ml) was slowly added dropwise to the mixture. The mixture was stirred for 15 min at −70° C. and for 15 min at room temperature. The mixture was quenched by addition of a saturated aqueous solution of ammonium chloride and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=99:1→97:3) to give the desired compound (6.99 g) having the following physical data.

TLC:Rf 0.44 (hexane:ethyl acetate=9:1).

REFERENCE EXAMPLE 130

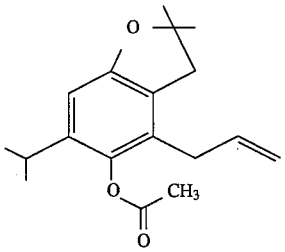

A

-continued

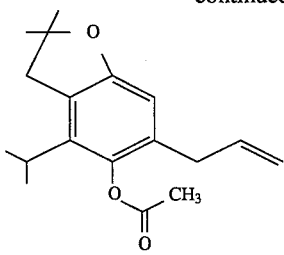

B

By the same procedure as reference example 13→reference example 14, using 2-isopropylphenol, the desired compound having the following physical data was given.

TLC: A: Rf 0.61 (hexane:ethyl acetate = 4:1);
B: Rf 0.66 (hexane:ethyl acetate = 4:1).

REFERENCE EXAMPLE 131

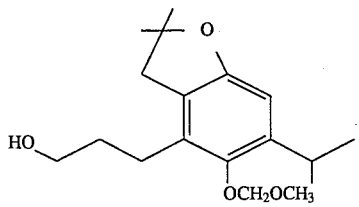

By the same procedure as reference example 8→reference example 10→reference example 21, using the compound A prepared in reference example 130, the desired compound having the following physical data was given.

TLC:Rf 0.46 (hexane:ethyl acetate=9:1).

REFERENCE EXAMPLE 132

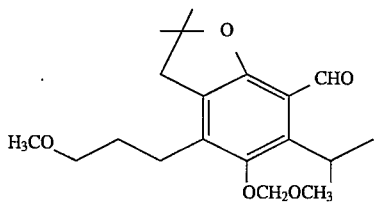

By the same procedure as reference example 78→reference example 25→reference example 9→reference example 10, using the compound prepared in reference example 131, the desired compound having the following physical data was given.

TLC:Rf 0.41 (hexane:ethyl acetate=4:1).

REFERENCE EXAMPLE 133

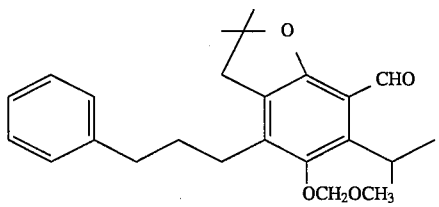

By the same procedure as reference example 125, using the compound prepared in reference example 131, the desired compound having the following physical data was given.

TLC:Rf 0.62 (hexane:ethyl acetate=4:1).

REFERENCE EXAMPLE 134

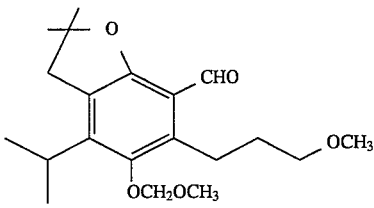

By the same procedure as reference example 131→reference. example 132, using the compound B prepared in reference example 130, the desired compound having the following physical data was given.

TLC:Rf 0.13 (hexane:ethyl acetate=10:1).

REFERENCE EXAMPLE 135

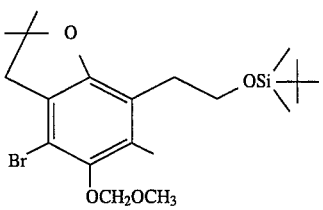

By the same procedure as reference example 25→reference example 9→reference example 10→reference example 23→reference example 21→reference example 115, using the compound prepared in reference example 129, the desired compound having the following physical data was given.

TLC:Rf 0.53 (hexane:ethyl acetate=9:1).

REFERENCE EXAMPLE 136

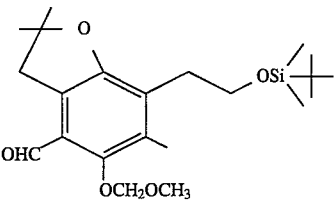

A small amount of o-phenanthroline (indicator) was added to a solution of the compound prepared in reference example 135 (3,73 g) and tetramethylethylenediamine (1.4 ml) in diethyl ether (16 ml). n-Butyllithium (5.6 ml, 1.6M solution in hexane) was added dropwise to the mixture at 0° C. under an atmosphere of argon. The mixture was stirred for 30 min and dimethylformamide (2.0 ml) was added dropwise to the mixture. The mixture was stirred for 40 min at 0° C. and 30 min at room temperature. The mixture was quenched by addition of ice water and a saturated aqueous solution of ammonium chloride. The mixture was extracted with diethyl ether. The extract was washed with water and a saturated aqueous solution of sodium chloride, successively, dried over anhydrous magnesium sulfate and concentrated. The residue was purified by column chromatography on silica gel (hexane:ethyl acetate=19:1→93:7) to give the desired compound (3.02 g) having the following physical data.

TLC:Rf 0.33 (hexane:ethyl acetate=9:1).

REFERENCE EXAMPLE 137

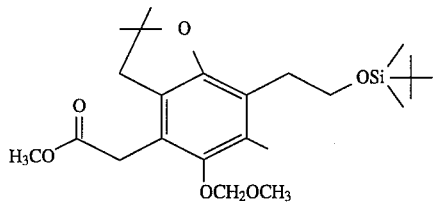

By the same procedure as reference example 23→reference example 21→reference example 22→reference example 31, using the compound prepared in reference example 136, the desired compound having the following physical data was given.

TLC:Rf 0.20 (hexane:ethyl acetate=10:1).

REFERENCE EXAMPLE 138

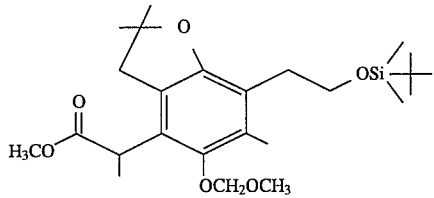

n-Butyllithium (4.1 ml, 1.6M solution in hexane) was added dropwise to a solution of diisopropylamine (0.92 ml) in tetrahydrofuran (2.5 ml) at 0° C. under an atmosphere of argon. The mixture was stirred for 30 min at 0° C. and cooled to −70° C. A solution of the compound prepared in reference example 137 (1.98 g) in tetrahydrofuran (8.5 ml) was added dropwise to the mixture. The mixture was stirred for 10 min. Methyl iodide (0.55 ml) was added dropwise to the mixture. The mixture was warmed to 0° C. and stirred for 20 min. The mixture was quenched by addition of a saturated aqueous solution of ammonium chloride and extracted with ethyl acetate. The extract was washed with water and a saturated aqueous solution of sodium chloride, successively, dried over anhydrous magnesium sulfate and concentrated to give the desired compound (2.17 g) having the following physical data.

TLC:Rf 0.41 (hexane:ethyl acetate=4:1).

REFERENCE EXAMPLE 139

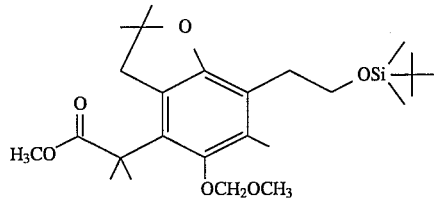

n-Butyllithium (4.1 ml, 1.6M solution in hexane) was added dropwise to a solution of diisopropylamine (0.92 ml) in tetrahydrofuran (2.5 ml) at 0° C. under an atmosphere of argon. The mixture was stirred for 30 min at 0° C. and cooled to −40° C. A solution of the compound prepared in reference example 138 (2.17 g) in tetrahydrofuran (8.5 ml) was added dropwise to the mixture. The mixture was stirred for 30 min. Methyl iodide (0.55 ml) was added dropwise to the mixture. The mixture was stirred for 50 min at room temperature. The mixture was quenched by addition of a saturated aqueous solution of ammonium chloride and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=93:7) to give the desired compound (2.04 g) having the following physical data.

TLC:Rf 0.44 (hexane:ethyl acetate=6:1).

REFERENCE EXAMPLE 140

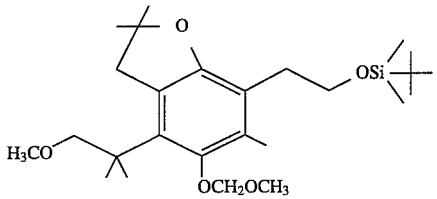

By the same procedure as reference example 47→reference example 78, using the compound prepared in reference example 139, the desired compound having the following physical data was given.

TLC:Rf 0.21 (hexane:ethyl acetate=9:1).

REFERENCE EXAMPLE 141

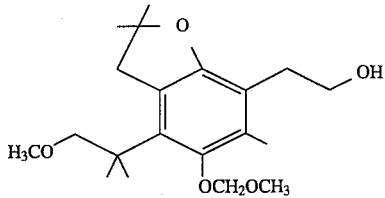

Tetrabutylammonium fluoride (0.44 ml, 1M solution in tetrahydrofuran) was added to a solution of the compound prepared in reference example 140 (134 mg) in tetrahydrofuran (1.4 ml) and the mixture was stirred for 1 h. The mixture was quenched by addition of a mixture of water and a saturated aqueous solution of sodium chloride and extracted with ethyl acetate. The extract was washed with a saturated aqueous solution of sodium chloride, dried over anhydrous magnesium sulfate and concentrated. The residue was purified by column chromatography on silica gel (hexane:ethyl acetate=7:3) to give the desired compound (109 mg) having the following physical data.

TLC:Rf 0.31 (hexane:ethyl acetate=2:1).

REFERENCE EXAMPLE 142

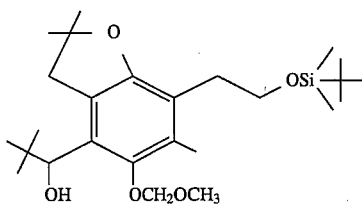

tert-Butylmagnesium chloride (2.4 ml, 2M solution in tetrahydrofuran) was added dropwise to a solution of the compound prepared in reference example 136 (651 mg) in tetrahydrofuran (3 ml) and the mixture was stirred for 1 h at room temperature. The mixture was quenched by addition of a saturated aqueous solution of ammonium chloride and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=15:1→12:1→10:1) to give the desired compound (489 mg) having the following physical data.

TLC:Rf 0.20 (hexane:ethyl acetate=10:1).

REFERENCE EXAMPLE 143

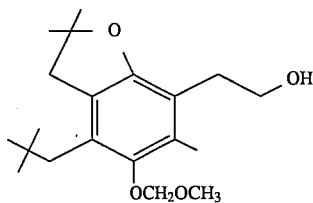

By the same procedure as reference example 141→reference example 63→reference example 71→reference example 10→reference example 8, using the compound prepared in reference example 142, the desired compound having the following physical data was given.

TLC:Rf 0.17 (hexane:ethyl acetate=4:1).

REFERENCE EXAMPLE 144

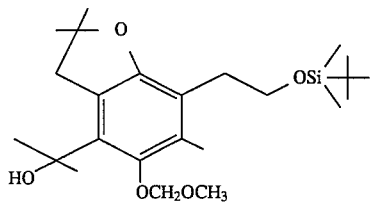

n-Butyllithium (3.2 ml, 1.6M solution in hexane) was added dropwise to a solution of the compound prepared in reference example 135 (770 mg) in diethyl ether (3 ml) at 0° C. and the mixture was stirred for 1 h at same temperature. Acetone (0.45 ml) and diethyl ether (3 ml) were added to the mixture. The mixture was stirred for 1 h, quenched by addition of ice water and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=15:1) to give the desired compound (247 mg) having the following physical data.

TLC:Rf 0.44 (hexane:ethyl acetate=4:1).

REFERENCE EXAMPLE 145

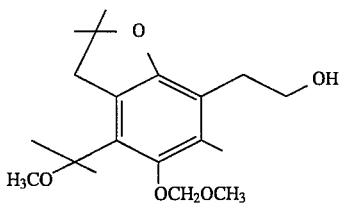

By the same procedure as reference example 78→reference example 1 41, using the compound prepared in reference example 144, the desired compound having the following physical data was given.

TLC:Rf 0.31 (hexane:ethyl acetate=2:1).

REFERENCE EXAMPLE 146

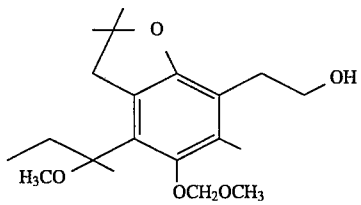

By the same procedure as reference example 144→reference example 145, using methyl ethyl ketone instead of acetone, the desired compound having the following physical data was given.

TLC:Rf 0.21 (hexane:ethyl acetate=3:1).

REFERENCE EXAMPLE 147

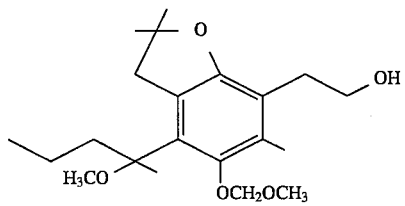

By the same procedure as reference example 144→reference example 145, using methyl propyl ketone instead of acetone, the desired compound having the following physical data was given.

TLC:Rf 0.11 (hexane:ethyl acetate=10:1).

REFERENCE EXAMPLE 148

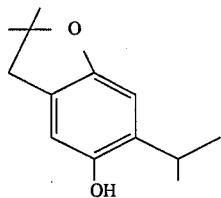

A

-continued

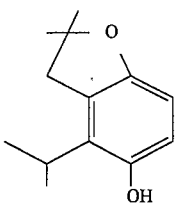
B

By the same procedure as reference example 62→reference example 63→reference example 64, using 2-isopropylphenol, the desired compound having the following physical data was given.

TLC:A:Rf 0.47 (hexane:ethyl acetate=4:1); B:Rf 0.49 (hexane:ethyl acetate=4:1).

REFERENCE EXAMPLE 149

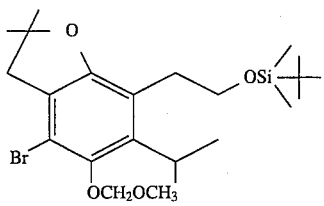

By the same procedure as reference example 10→reference example 129→reference example 25→reference example 9→reference example 10→reference example 23→reference example 21→reference example 115, using the compound A prepared in reference example 148, the desired compound having the following physical data was given.

TLC:Rf 0.76 (hexane:ethyl acetate=4:1).

REFERENCE EXAMPLE 150

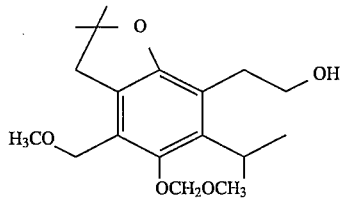

By the same procedure as reference example 136→reference example 104→reference example 78→reference example 141, using the compound prepared in reference example 149, the desired compound having the following physical data was given.

TLC:Rf 0.35 (hexane:ethyl acetate=2:1).

REFERENCE EXAMPLE 151

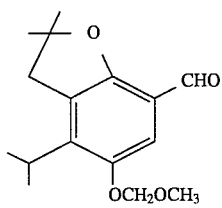

By the same procedure as reference example 9→reference example 10, using the compound B prepared in reference example 148, the desired compound having the following physical data was given.

TLC:Rf 0.60 (hexane:ethyl acetate=4:1).

REFERENCE EXAMPLE 152

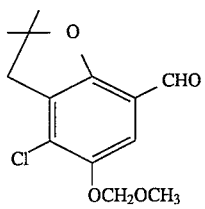

By the same procedure as reference example 63→reference example 10→reference example 8→reference example 5→reference example 6→reference example 7, using chlorohydroquinone, the desired compound having the following physical data was given.

TLC:Rf 0.67 (hexane:ethyl acetate=4:1).

REFERENCE EXAMPLE 153

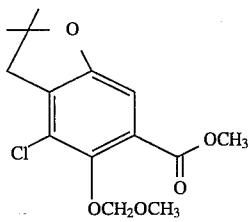

Tetramethylethylenediamine (0.76 ml) and n-butyllithium (3.1 ml, 1.6M solution in hexane) were added dropwise to a solution of the compound prepared in reference example 152 (1.1 g) in diethyl ether (5 ml) at 0° C., successively, and the mixture was stirred for 1 h. The mixture was cooled to −78° C., passed through the tube in an atmosphere of carbon dioxide for 10 min and stirred for 30 min at 0° C. The mixture was quenched by addition of ice water. 1N Aqueous solution of hydrochloric acid was added to the mixture until pH 3–4. The mixture was extracted with ethyl acetate. The extract was washed with water, a saturated aqueous solution of sodium hydrogen carbonate and a saturated aqueous solution of sodium chloride, successively, dried over anhydrous magnesium sulfate and concentrated. A solution of diazomethane in diethyl ether was added to a solution of the residue in diethyl ether (5 ml) at 0° C. and the mixture was concentrated. The residue was purified by column chromatography on silica gel (hexane:ethyl acetate=15:1) to give the desired compound (480 mg) having the following physical data.

TLC:Rf 0.48 (hexane:ethyl acetate=4:1).

REFERENCE EXAMPLE 154

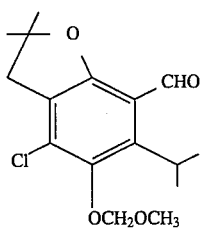

By the same procedure as reference example 32→reference example 71→reference example 9→reference example 10, using the compound prepared in reference example 153, the desired compound having the following physical data was given.

TLC:Rf 0.37 (hexane:ethyl acetate=4:1).

REFERENCE EXAMPLE 155

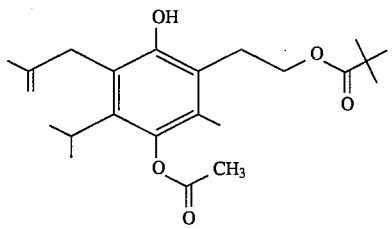

By the same procedure as reference example 9→reference example 23→reference example 21→reference example 63→reference example 3→reference example 4→reference example 5→reference example 6, using the compound prepared in reference example 4, the desired compound having the following physical data was given.

TLC:Rf 0.38 (hexane:ethyl acetate=4:1).

REFERENCE EXAMPLE 156

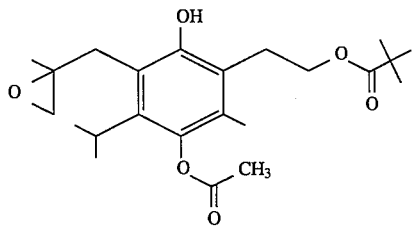

m-Chloroperoxybenzoic acid (11.3 g, 55% content) was added to a solution of the compound prepared in reference example 155 (9.35 g) in dichloromethane (100 ml) at 0° C. and the mixture was stirred for 1 h. The mixture was quenched by addition of a saturated aqueous solution of sodium thiosulfate and a saturated aqueous solution of sodium hydrogen carbonate. The mixture was extracted with ethyl acetate. The extract was washed with a saturated aqueous solution of sodium hydrogen carbonate, water and a saturated aqueous solution of sodium chloride, successively, dried over anhydrous magnesium sulfate and concentrated to give the desired compound having the following physical data.

TLC:Rf 0.31 (hexane:ethyl acetate=4:1).

REFERENCE EXAMPLE 157

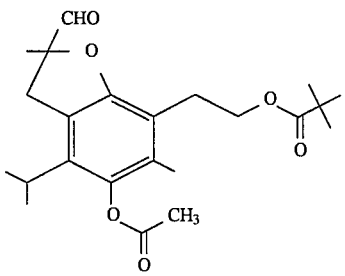

By the same procedure as reference example 7→reference example 22, using the compound prepared in reference example 156, the desired compound having the following physical data was given.

TLC:Rf 0.51 (hexane:ethyl acetate=2:1).

REFERENCE EXAMPLE 158

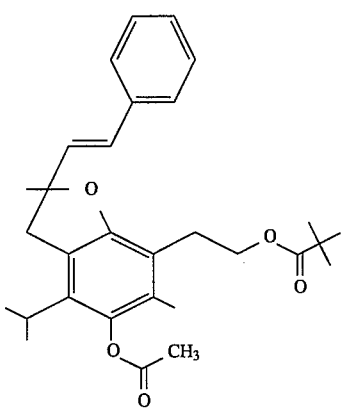

A suspension of sodium hydride (79 mg, 60% content) in dimethylformamide (2 ml) was stirred for 1 h at 70° C. A solution of benzyltriphenylphosphonium chloride (770 mg) in dimethylformamide (2 ml) was added dropwise to the suspension at room temperature, and the mixture was stirred for 15 min. A solution of the compound prepared in reference example 157 (400 mg) in dimethylformamide (1 ml) was added dropwise to the mixture. The mixture was stirred for 1 h at room temperature, quenched by addition of ice water and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=9:1) to give the desired compound (540 mg) having the following physical data.

TLC:Rf 0.26 (flexane:ethyl acetate=9:1).

REFERENCE EXAMPLE 159

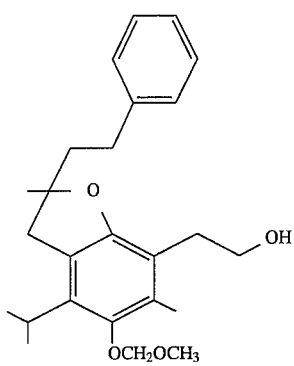

By the same procedure as reference example 15→reference example 47→reference example 10, using the compound prepared in reference example 158, the desired compound having the following physical data was given.

TLC:Rf 0.40 (hexane:ethyl acetate=2:1).

REFERENCE EXAMPLE 160

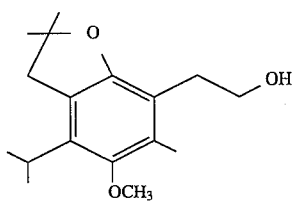

By the same procedure as reference example 23→reference example 21→reference example 25→reference example 78, using the compound prepared in reference example 10, the desired compound having the following physical data was given.

TLC:Rf 0.50 (hexane:ethyl acetate=2:1).

REFERENCE EXAMPLE 161

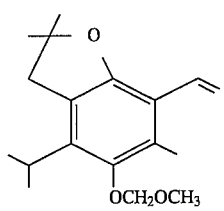

A suspension of sodium hydride (109 mg, 60% content) in dimethylsulfoxide (1 ml) was stirred for 1 h at 70° C. under an atmosphere of argon. The suspension was cooled to room temperature. A solution of methyltriphenylphosphonium bromide (978 mg) in dimethylsulfoxide (2 ml) was added to the suspension and the mixture was stirred for 20 min. A solution of the compound prepared in reference example 10 (400 mg) in dimethylsulfoxide (2 ml) was added to the mixture. The mixture was stirred for 30 min at room temperature. The mixture was poured into ice water (30 ml) and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate= 40:1) to give the desired compound (382 mg) having the following physical data.

TLC:Rf 0.34 (hexane:ethyl acetate=19:1).

REFERENCE EXAMPLE 162

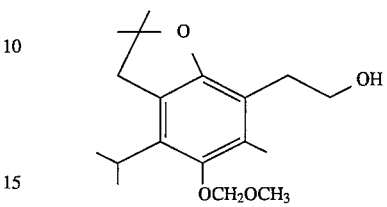

9-Borabicyclo[3.3.1]nonane (7.7 ml, 0.5M solution in tetrahydrofuran) was added to a solution of the compound prepared in reference example 161 (373 mg) in tetrahydrofuran (2 ml) and the mixture was stirred at room temperature overnight. Methanol (2.2 ml), 6N aqueous solution of sodium hydroxide (0.77 ml) and 30% aqueous solution of hydrogen peroxide (1.54 ml) were added to the mixture, successively. The mixture was stirred for 30 min at 50° C., cooled to room temperature and concentrated. Water was added to the residue and the mixture was extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=2:1) to give the desired compound (396 mg) having the following physical data.

TLC:Rf 0.36 (hexane:ethyl acetate=2:1).

REFERENCE EXAMPLE 163

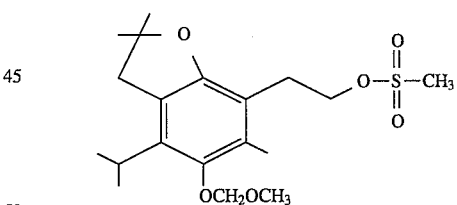

Mesyl chloride (0.15 ml) and triethylamine (0.27 ml) were added to a solution of the compound prepared in reference example 162 (400 mg) in dichloromethane (6 ml) at −20° C., successively. The mixture was stirred for 10 min at −20° C., quenched by addition of water and extracted with ethyl acetate. The extract was washed with 1N aqueous solution of hydrochloric acid, water, a saturated aqueous solution of sodium hydrogen carbonate, water and a saturated aqueous solution of sodium chloride, successively, dried over anhydrous magnesium sulfate and concentrated to give the desired compound (503 mg) having the following physical data.

TLC:Rf 0.41 (hexane:ethyl acetate=2:1).

EXAMPLE 1

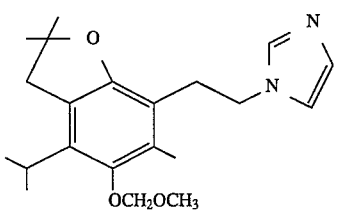

Imidazole (1.7 g) was added to a solution of the compound prepared in reference example 163 (503 mg) in toluene (4 ml). The mixture was stirred for 1 h at 100° C. and cooled to room temperature. The mixture was quenched by addition of a saturated aqueous solution of sodium hydrogen carbonate and extracted with diethyl ether. The extract was washed with water and a saturated aqueous solution of sodium chloride, successively, dried over anhydrous magnesium sulfate and concentrated. The residue was purified by column chromatography on silica gel (chloroform:methanol =60:1) to give the desired compound (464 mg) having the following physical data.

TLC:Rf 0.45 (chloroform:methanol=19:1).

EXAMPLE 2

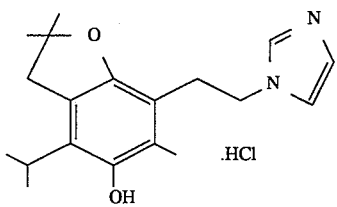

Hydrogen chloride (1.3 ml, 4N solution in dioxane) was added to a solution of the compound prepared in example 1 (464 mg) in dioxane (4 ml). The mixture was stirred for 20 min at room temperature and concentrated. Diethyl ether was added to the residue and the mixture was filtered. The white crystal was washed with diethyl ether and dried under reduced pressure to give the desired compound (358 mg) having the following physical data.

TLC:Rf 0.46 (chloroform:methanol=9:1);

IR:ν 3253, 2964, 2826, 1577, 1430, 1259, 1164, 1079, 899, 639 cm$^{-1}$.

EXAMPLE 2(a)–(ll)

By the same procedure as reference example 161→reference example 162→reference example 163→example 1→example 2, the following compounds were given by using corresponding aldehyde (compound prepared in reference example described hereinbefore) instead of the compound prepared in reference example 10.

EXAMPLE 2(a)

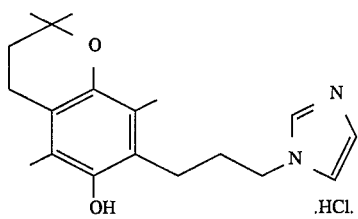

TLC:Rf 0.18 (chloroform:methanol=19:1);

IR:ν 3368, 3131, 3094, 3035, 2940, 2863, 1579, 1547, 1447, 1263, 1223, 1169, 1126, 1082, 929, 622 cm$^{-1}$.

EXAMPLE 2(b)

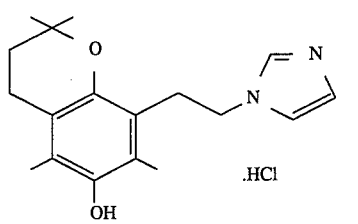

TLC:Rf 0.20 (chloroform:methanol=19:1);

IR:ν 3284, 1576, 1546, 1450, 1224, 1166, 1126, 1085, 934, 768, 637 cm$^{-1}$.

EXAMPLE 2(c)

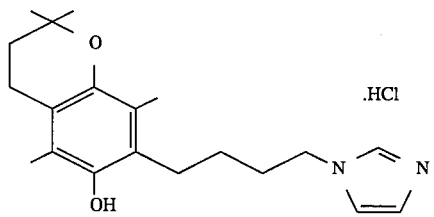

TLC:Rf 0.11 (chloroform:methanol=19:1);

IR:ν 3391, 2937, 1577, 1547, 1446, 1275, 1202, 1167, 1111, 1035, 834, 638 cm$^{-1}$.

EXAMPLE 2(d)

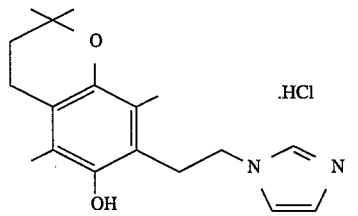

TLC:Rf 0.46 (chloroform:methanol=9:1);

IR:ν 3084, 2971, 1576, 1544, 1459, 1417, 1287, 1221, 1170, 1080, 929, 756, 636, 619 cm$^{-1}$.

EXAMPLE 2(e)

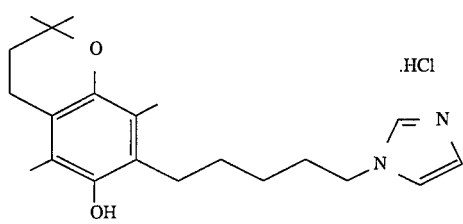

TLC:Rf 0.28 (chloroform:methanol=19:1);

IR:ν 3333, 3112, 3031, 3001, 2932, 2839, 2615, 1577, 1548, 1454, 1412, 1382, 1348, 1287, 1262, 1226, 1169, 1114, 1091, 1064, 1044, 926, 827, 767, 672, 635, 623 cm$^{-1}$.

EXAMPLE 2(f)

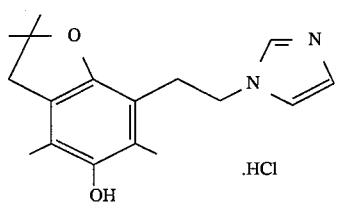

TLC:Rf 0.21 (chloroform:methanol=19:1);

IR:ν 3401, 3091, 3030, 2927, 2830, 1649, 1578, 1547, 1446, 1368, 1290, 1273, 1152, 1075, 1028, 878 cm$^{-1}$.

EXAMPLE 2(g)

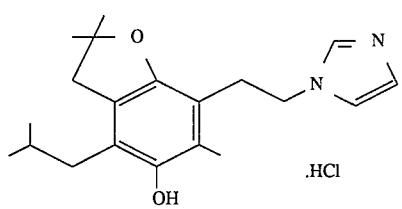

TLC:Rf 0.15 (chloroform:methanol=19:1);

IR:ν 3402, 1577, 1544, 1436, 1368, 1314, 1290, 1264, 1215, 1158, 1112, 1083, 1053, 907, 824, 748, 633 cm$^{-1}$.

EXAMPLE 2(h)

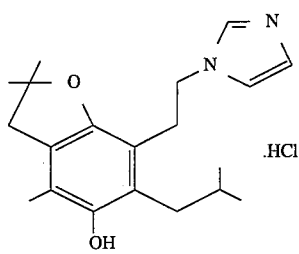

TLC:Rf 0.29 (chloroform:methanol=19:1);

IR:ν 1575, 1452, 1421, 1367, 1286, 1264, 1206, 1156, 1098, 1086, 969, 886, 853, 737, 631 cm$^{-1}$.

EXAMPLE 2(i)

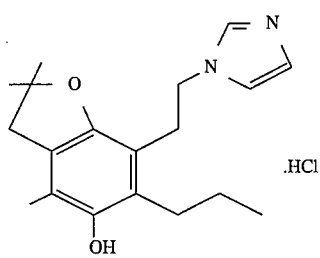

TLC:Rf 0.30 (chloroform:methanol=19:1);

IR (film):ν 2964, 1503, 1456, 1368, 1285, 1260, 1155, 1108, 1078, 907, 734 cm$^{-1}$.

EXAMPLE 2(j)

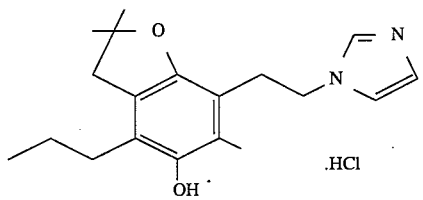

TLC:Rf 0.28 (chloroform:methanol=19:1);

IR (film):ν 2962, 1509, 1432, 1285, 1259, 1156, 1107, 1079, 919 cm$^{-1}$.

EXAMPLE 2(k)

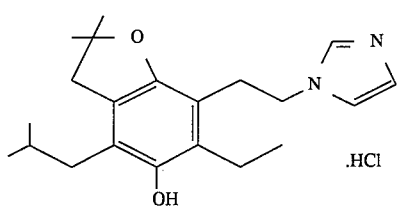

TLC:Rf 0.33 (chloroform:methanol=19:1);

IR:ν 3246, 1579, 1543, 1467, 1428, 1368, 1289, 1254, 1222, 1155, 1086, 1054, 943, 900, 788, 733, 619 cm$^{-1}$.

EXAMPLE 2(l)

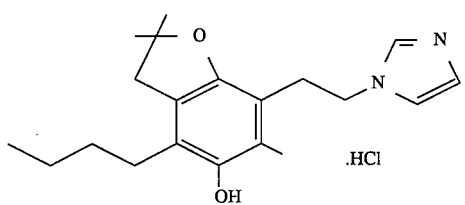

TLC:Rf 0.11 (chloroform:methanol=19:1);

IR:ν 3392, 2954, 2809, 1576, 1544, 1437, 1314, 1290, 1269, 1214, 1156, 1109, 1083, 886, 824, 748, 633 cm$^{-1}$.

EXAMPLE 2(m)

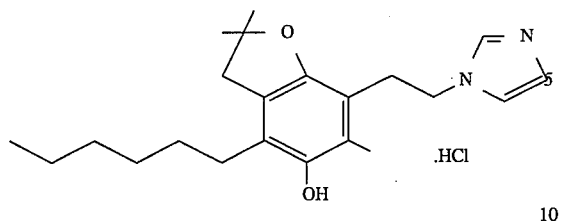

TLC:Rf 0.38 (chloroform:methanol=9:1);

IR:ν 3392, 2928, 2858, 1545, 1436, 1290, 1215, 1083, 908, 634 cm$^{-1}$.

EXAMPLE 2(n)

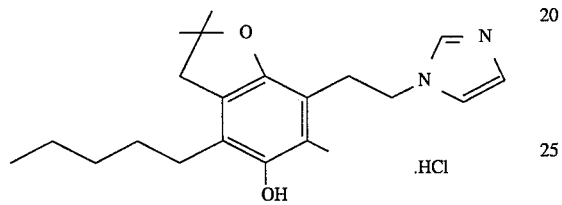

TLC:Rf 0.15 (chloroform:methanol=19:1);

IR:ν 3398, 1577, 1544, 1437, 1386, 1315, 1290, 1264, 1215, 1156, 1111, 1083, 897, 823, 748, 634 cm$^{-1}$.

EXAMPLE 2(o)

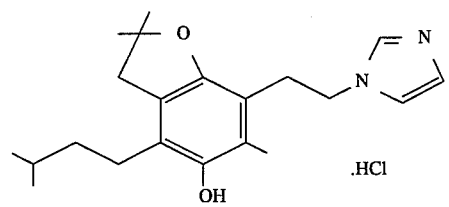

TLC:Rf 0.14 (chloroform:methanol=10:1);

IR:ν 3272, 2927, 2364, 1577, 1548, 1439, 1273, 1166, 1081, 886, 637 cm$^{-1}$.

EXAMPLE 2(p)

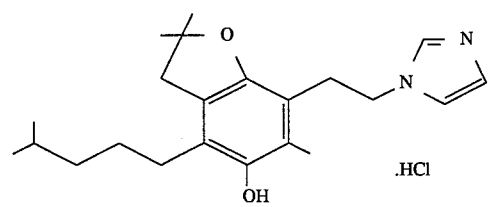

TLC:Rf 0.42 (chloroform:methanol=10:1);

IR:ν 3401, 2929, 2706, 1578, 1544, 1438, 1367, 1316, 1291, 1215, 1170, 1114, 1084, 897, 833, 750, 684, 631 cm$^{-1}$.

EXAMPLE 2(q)

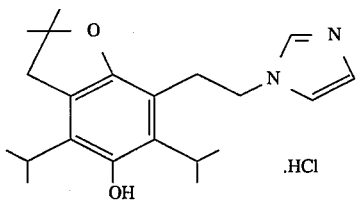

TLC:Rf 0.31 (chloroform:methanol=19:1);

IR:ν 3403, 1578, 1544, 1424, 1369, 1289, 1256, 1207, 1148, 1102, 1055, 873, 814, 629 cm$^{-1}$.

EXAMPLE 2(r)

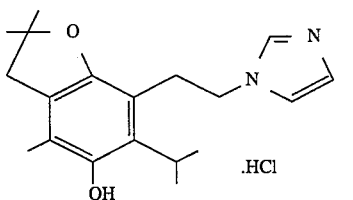

TLC:Rf 0.48 (chloroform:methanol=9:1);

IR:ν 3273, 2950, 1577, 1549, 1451, 1422, 1368, 1255, 1208, 1153, 1120, 1082, 1016, 873, 627 cm$^{-1}$.

EXAMPLE 2(s)

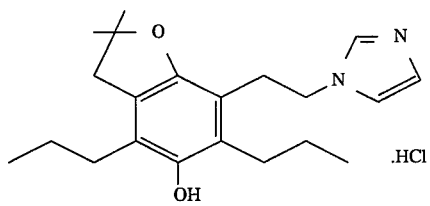

TLC:Rf 0.46 (chloroform:methanol=9:1);

IR:ν 3368, 2960, 1574, 1545, 1430, 1369, 1287, 1257, 1201, 1156, 1085, 889, 624 cm$^{-1}$.

EXAMPLE 2(t)

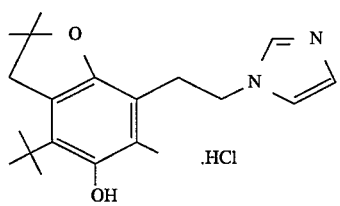

TLC:Rf 0.34 (chloroform:methanol=19:1);

IR:ν 1614, 1574, 1547, 1440, 1407, 1357, 1312, 1288, 1269, 1225, 1162, 1074, 907, 805, 762, 675, 634 cm$^{-1}$.

EXAMPLE 2(u)

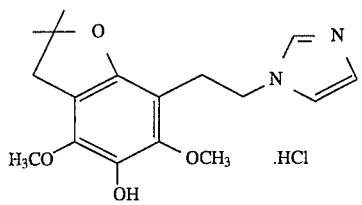

TLC:Rf 0.12 (chloroform:methanol=20:1);

IR (film):ν 3139, 2971, 1626, 1577, 1546, 1461, 1429, 1371, 1245, 1200, 1093, 1054, 1002, 970, 733 cm$^{-1}$.

EXAMPLE 2(v)

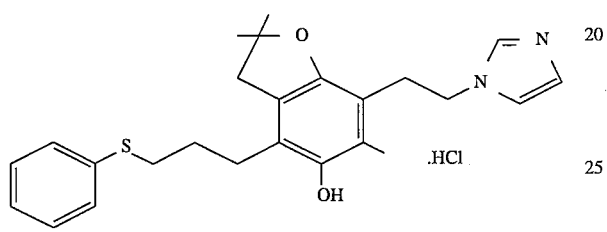

TLC:Rf 0.43 (chloroform:methanol=19:1);

IR:ν 3403, 1578, 1544, 1438, 1314, 1290, 1215, 1132, 1083, 1022, 898, 822, 743, 688, 634 cm$^{-1}$.

EXAMPLE 2(w)

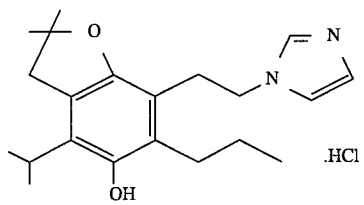

TLC:Rf 0.47 (chloroform:methanol=10:1);

IR:ν 3402, 2964, 2870, 1577, 1545, 1425, 1369, 1286, 1257, 1210, 1153, 1086, 889, 625 cm$^{-1}$.

EXAMPLE 2(x)

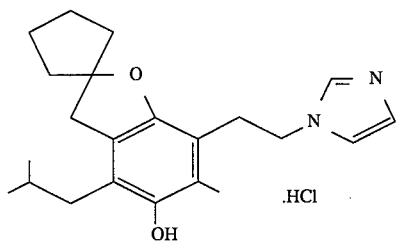

TLC:Rf 0.28 (chloroform:methanol=19:1);

IR:ν 3368, 2960, 2795, 1579, 1546, 1446, 1327, 1251, 1087 cm$^{-1}$.

EXAMPLE 2(y)

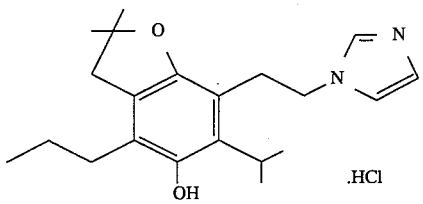

TLC:Rf 0.64 (chloroform:methanol=9:1);

IR:ν 3305, 3160, 3111, 2990, 2960, 2927, 2870, 2804, 2711, 2618, 1582, 1551, 1446, 1427, 1357, 1337, 1320, 1283, 1259, 1221, 1198, 1155, 1110, 1090, 1073, 1025, 951, 915, 872, 829, 785, 754, 688, 625 cm$^{-1}$.

EXAMPLE 2(z)

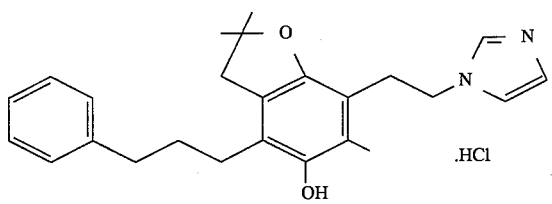

TLC:Rf 0.40 (chloroform:methanol=19:1);

IR:ν 3392, 1576, 1544, 1437, 1368, 1314, 1289, 1267, 1214, 1083, 895, 822, 747, 697, 634, 622 cm$^{-1}$.

EXAMPLE 2(aa)

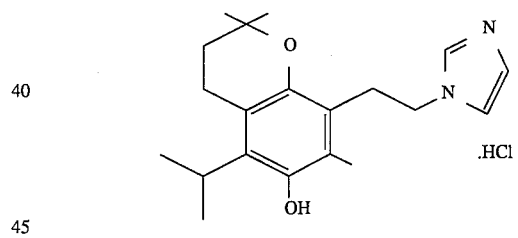

TLC:Rf 0.45 (chloroform:methanol=9:1);

IR:ν 3318, 3035, 2950, 2826, 1574, 1544, 1424, 1350, 1298, 1268, 1225, 1173, 1123, 1083, 933, 756, 639 cm$^{-1}$.

EXAMPLE 2(bb)

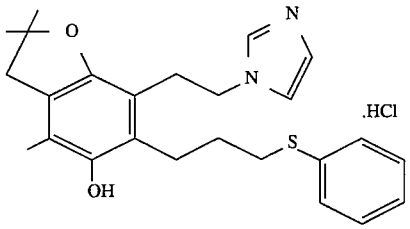

TLC:Rf 0.45 (chloroform:methanol=19:1);

IR:ν 3397, 1581, 1545, 1481, 1439, 1369, 1288, 1264, 1211, 1156, 1088, 1025, 889, 785, 744, 693, 624 cm$^{-1}$.

103

EXAMPLE 2 (cc)

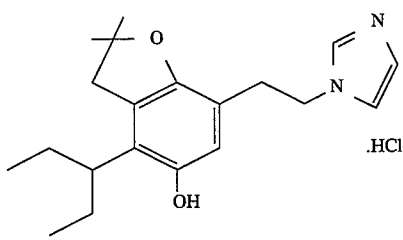

TLC:Rf 0.48 (chloroform:methanol=9:1);

IR:ν 3370, 3126, 3029, 2963, 2931, 2868, 2613, 1575, 1545, 1429, 1368, 1290, 1213, 1162, 1111, 1075, 908, 879, 808, 757, 673, 633 cm$^{-1}$.

EXAMPLE 2(dd)

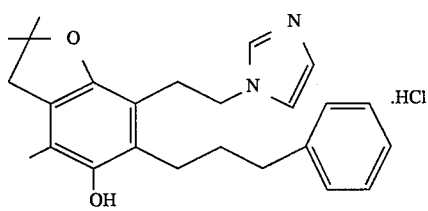

TLC:Rf 0.41 (chloroform:methanol=19:1);

IR:ν 3401, 1577, 1545, 1496, 1455, 1424, 1369, 1288, 1265, 1157, 1081, 889, 784, 751, 703, 624 cm$^{-1}$.

EXAMPLE 2 (ee)

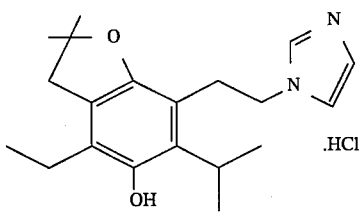

TLC:Rf 0.48 (chloroform:methanol=19:1);

IR:ν 3420, 1546, 1510, 1429, 1370, 1289, 1257, 1207, 1153, 1108, 1084, 1028, 876, 819, 753, 627 cm$^{-1}$.

EXAMPLE 2 (ff)

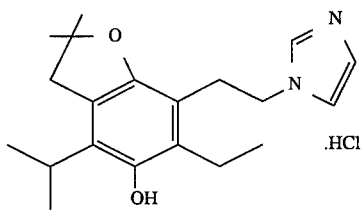

TLC:Rf 0.43 (chloroform:methanol=10:1);

IR (film):ν 3368, 2968, 1577, 1546, 1426, 1369, 1289, 1258, 1213, 1153, 1088, 1058, 899, 754 cm$^{-1}$.

104

EXAMPLE 2 (gg)

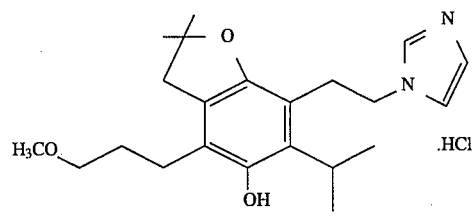

TLC:Rf 0.47 (chloroform:methanol=20:1);

IR:ν 3103, 2971, 2927, 1510, 1431, 1386, 1366, 1304, 1286, 1251, 1227, 1173, 1153, 1108, 1081, 1028, 943, 920, 880, 831 cm$^{-1}$.

EXAMPLE 2 (hh)

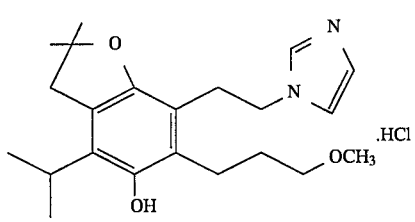

TLC:Rf 0.38 (chloroform:methanol=15:1);

IR (film):ν 3367, 2966, 1577, 1547, 1426, 1384, 1369, 1288, 1258, 1154, 1110, 873, 755 cm$^{-1}$.

EXAMPLE 2(ii)

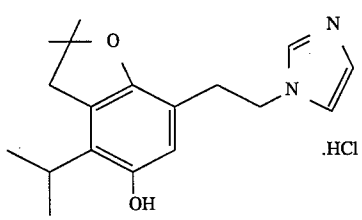

TLC:Rf 0.18 (chloroform:methanol=19:1);

IR:ν 3256, 1626, 1578, 1545, 1445, 1427, 1370, 1352, 1285, 1233, 1169, 1143, 889, 871, 829, 628 cm$^{-1}$.

EXAMPLE 2 (jj)

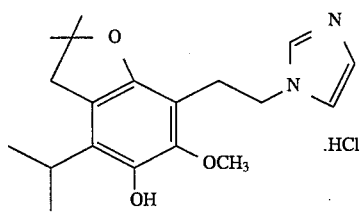

TLC:Rf 0.40 (chloroform:methanol=19:1);

IR:ν 3539, 3333, 3128, 3094, 3035, 2960, 2932, 2823, 2609, 1626, 1578, 1548, 1446, 1425, 1371, 1359, 1323, 1284, 1190, 1166, 1089, 1054, 994, 940, 905, 832, 759, 669, 635 cm$^{-1}$.

EXAMPLE 2 (kk)

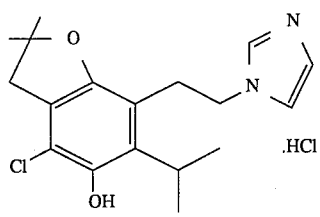
.HCl

TLC:Rf 0.50 (chloroform:methanol=19:1);

IR:ν 3395, 3138, 2965, 2868, 1574, 1545, 1425, 1370, 1290, 1198, 1176, 1142, 1087, 1055, 1039, 951, 923, 873, 791, 756, 625 cm$^{-1}$.

EXAMPLE 2(ll)

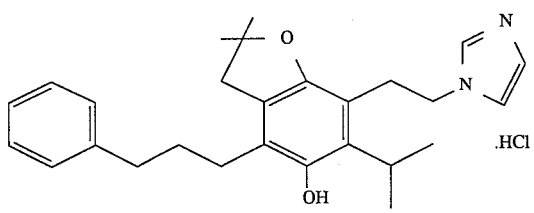
.HCl

TLC:Rf 0.25 (chloroform:methanol=19:1);

IR:ν 3393, 1573, 1544, 1497, 1428, 1368, 1288, 1258, 1208, 1152, 1083, 1028, 876, 751, 702, 625 cm$^{-1}$.

EXAMPLE 3

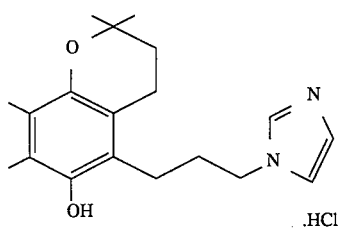
.HCl

By the same procedure as reference example 45→reference example 46→reference example 47→reference example 163→example 1→example 2, using the compound prepared in reference example 58, the desired compound having the following physical data was given.

TLC:Rf 0.20 (chloroform:methanol=19:1);

IR:ν 3490, 3417, 3138, 3098, 2974, 1547, 1455, 1368, 1252, 1228, 1170, 1124, 1089, 927, 844, 762, 623 cm$^{-1}$.

EXAMPLE 3(a)–3(m)

By the same procedure as example 3, the following compounds were given by using corresponding aldehyde (compound prepared in reference example described hereinbefore) instead of the compound prepared in reference example 58.

EXAMPLE 3 (a)

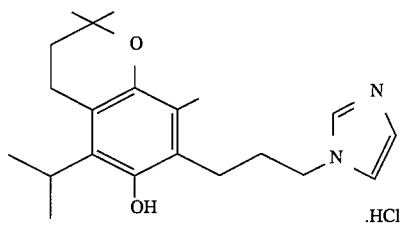
.HCl

TLC:Rf 0.39 (chloroform:methanol=9:1);

IR:ν 3402, 3142, 2931, 2871, 1638, 1577, 1546, 1450, 1419, 1382, 1368, 1274, 1225, 1175, 1162, 1125, 1088, 949, 930, 904, 845, 756, 625 cm$^{-1}$.

EXAMPLE 3 (b)

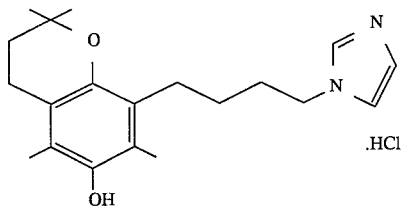
.HCl

TLC:Rf 0.25 (chloroform:methanol=19:1);

IR:ν 3371, 1576, 1547, 1455, 1265, 1221, 1170, 1128, 1099, 1021, 763 cm$^{-1}$.

EXAMPLE 3(c)

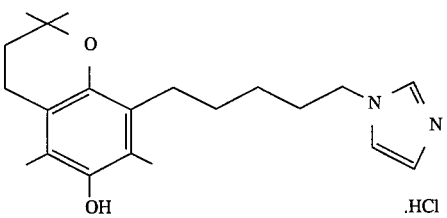
.HCl

TLC:Rf 0.20 (chloroform:methanol=19:1);

IR:ν 3294, 1575, 1548, 1455, 1372, 1264, 1224, 1172, 1129, 1086, 926, 901, 771, 635 cm$^{-1}$.

EXAMPLE 3(d)

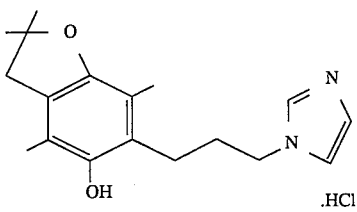
.HCl

TLC:Rf 0.09 (chloroform:methanol=19:1);

IR:ν 3385, 3042, 2955, 1576, 1543, 1447, 1273, 1178, 1064, 888, 821, 622 cm$^{-1}$.

EXAMPLE 3(e)

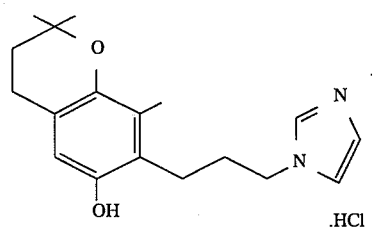

TLC:Rf 0.35 (ethyl acetate:methanol=9:1);
IR:ν 3143, 3045, 2971, 1576, 1439, 1333, 1249, 1207, 1156, 1120, 1062, 939, 818, 738, 623 cm$^{-1}$.

EXAMPLE 3(f)

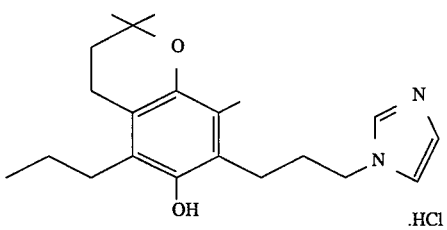

TLC:Rf 0.38 (chloroform:methanol=19:1);
IR (film):ν 2932, 1509, 1446, 1367, 1261, 1226, 1166, 1110, 1084, 924, 754 cm$^{-1}$.

EXAMPLE 3(g)

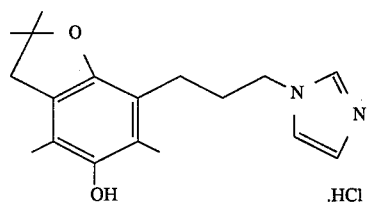

TLC:Rf 0.47 (chloroform:methanol=9:1);
IR.:ν 3254, 3137, 3086, 3008, 2937, 2846, 2628, 1574, 1548, 1447, 1423, 1367, 1297, 1270, 1162, 1084, 1025, 861, 810, 623 cm$^{-1}$.

EXAMPLE 3(h)

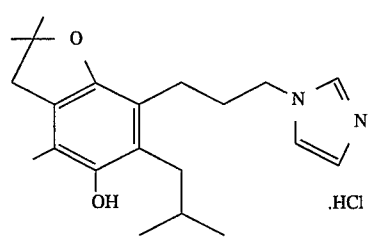

TLC:Rf 0.29 (chloroform:methanol=19:1);
IR:ν 3393, 1577, 1544, 1451, 1424, 1286, 1261, 1207, 1154, 1086, 1042, 906, 849, 785, 629 cm$^{-1}$.

EXAMPLE 3(i)

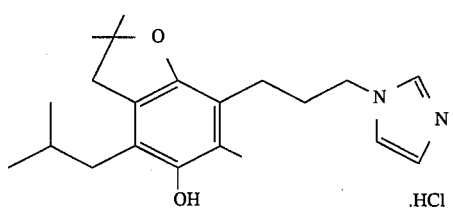

TLC:Rf 0.48 (chloroform:methanol=9:1);
IR:ν 3269, 3096, 2964, 2863, 1571, 1544, 1434, 1367, 1258, 1211, 1156, 1083 cm$^{-1}$.

EXAMPLE 3(j)

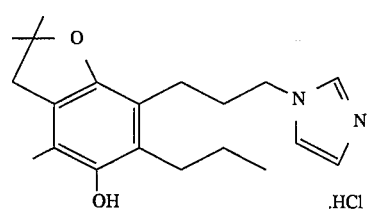

TLC:Rf 0.19 (chloroform:methanol=20:1);
IR (film):ν 2963, 2869, 1574, 1546, 1455, 1369, 1260, 1207, 1154, 1087, 907, 851, 754 cm$^{-1}$.

EXAMPLE 3(k)

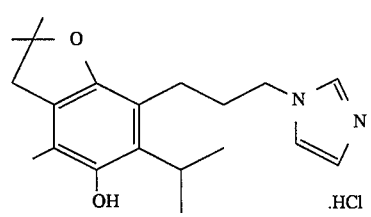

TLC:Rf 0.24 (chloroform:methanol=20:1);
IR:ν 3307, 2962, 2583, 1572, 1545, 1451, 1333, 1269, 1208, 1153, 1082, 1017, 897, 831, 780, 623 cm$^{-1}$.

EXAMPLE 3(l)

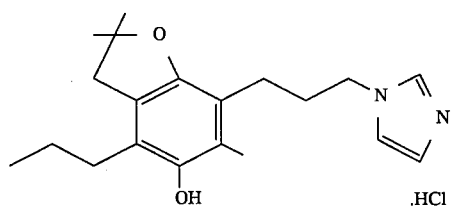

TLC:Rf 0.40 (chloroform:methanol=19:1);
IR:ν 3367, 1627, 1574, 1545, 1430, 1368, 1288, 1258, 1215, 1155, 1104, 1086, 1052, 1010, 917, 860, 785, 626 cm$^{-1}$.

EXAMPLE 3(m)

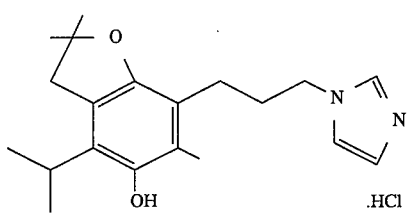

TLC:Rf 0.11 (chloroform:methanol=20:1);

IR (film):ν 3435, 3138, 2930, 2869, 2359, 1578, 1424, 1358, 1267, 1215, 1164, 1098, 1047, 909, 832, 735 cm$^{-1}$.

EXAMPLE 4

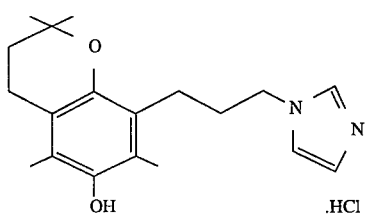

By the same procedure as reference example 104→reference example 163→example 1→example 2, using the compound prepared in reference example 48, the desired compound having the following physical data was given.

TLC:Rf 0.20 (chloroform:methanol=19:1);

IR:ν 3402, 1577, 1546, 1451, 1368, 1264, 1225, 1165, 1125, 1086, 1049, 900, 626 cm$^{-1}$.

EXAMPLE 4(a)–4(n)

By the same procedure as example 4, the following compounds were given by using corresponding aldehyde (compound prepared in reference example described hereinbefore) instead of the compound prepared in reference example 48.

EXAMPLE 4(a)

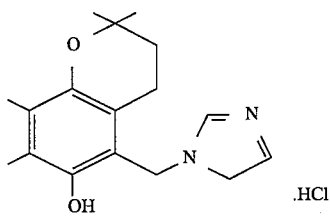

TLC:Rf 0.50 (chloroform:methanol=9:1);

IR:ν 3436, 1516, 1451, 1267, 1228, 1081, 735 cm$^{-1}$.

EXAMPLE 4(b)

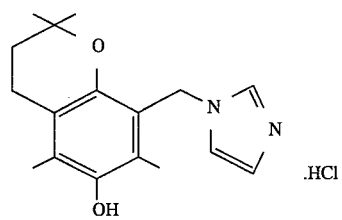

TLC:Rf 0.50 (chloroform:methanol=9:1);

IR:ν 3392, 1571, 1544, 1451, 1269, 1227, 1166, 1126, 1080, 1062, 924, 815, 640, 626 cm$^{-1}$.

EXAMPLE 4(c)

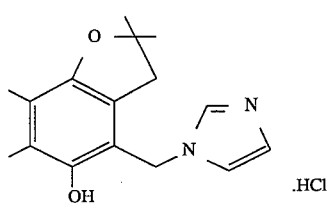

TLC:Rf 0.12 (chloroform:methanol=19:1);

IR:ν 3140, 2980, 2933, 1572, 1457, 1277, 1083, 994, 869, 741, 635 cm$^{-1}$.

EXAMPLE 4(d)

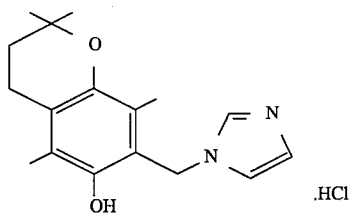

TLC:Rf 0.27 (chloroform:methanol=19:1);

IR:ν 1613, 1557, 1473, 1417, 1286, 1236, 1169, 1128, 1062, 931, 778, 677 cm$^{-1}$.

EXAMPLE 4(e)

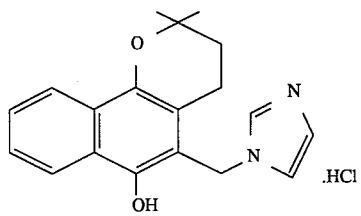

TLC:Rf 0.53 (chloroform:methanol=9:1);

IR:ν 1577, 1546, 1450, 1384, 1283, 1187, 1165, 1121, 1047, 998, 826, 774, 749, 637 cm$^{-1}$.

EXAMPLE 4(f)

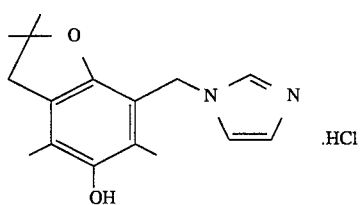

TLC:Rf 0.40 (chloroform:methanol=9:1);
IR:ν 3333, 3150, 3092, 3030, 2980, 2932, 2813, 2737, 2610, 1563, 1541, 1453, 1367, 1278, 1209, 1154, 1079, 1056, 867, 781, 756, 638, 626 cm$^{-1}$.

EXAMPLE 4(g)

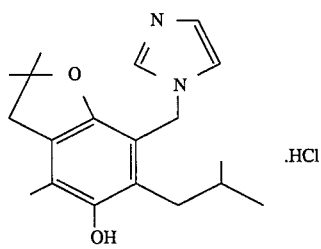

TLC:Rf 0.33 (chloroform:methanol=19:1);
IR:ν 3393, 1571, 1544, 1450, 1369, 1271, 1202, 1158, 1080, 883, 857, 810, 782, 748, 637 cm$^{-1}$.

EXAMPLE 4(h)

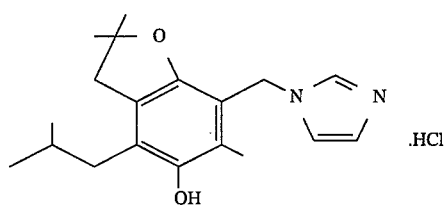

TLC:Rf 0.45 (chloroform:methanol=9:1);
IR:ν 3436, 3119, 2958, 2867, 1637, 1575, 1543, 1443, 1369, 1259, 1156, 1114, 1053 cm$^{-1}$.

EXAMPLE 4(i)

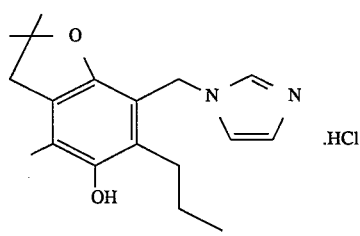

TLC:Rf 0.28 (chloroform:methanol=20:1);
IR (film):ν 3151, 2964, 2870, 1572, 1542, 1456, 1370, 1266, 1207, 1155, 1079, 884, 854, 728 cm$^{-1}$.

EXAMPLE 4(j)

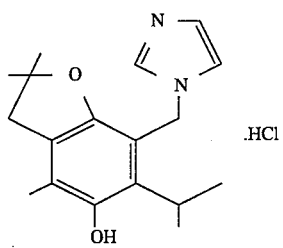

TLC:Rf 0.23 (chloroform:methanol=20:1);
IR:ν 3401, 2927, 2682, 1572, 1544, 1459, 1270, 1206, 1164, 1075, 1011, 883, 763, 658 cm$^{-1}$.

EXAMPLE 4(k)

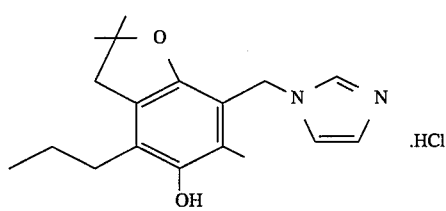

TLC:Rf 0.38 (chloroform:methanol=19:1);
IR:ν 3132, 1623, 1572, 1542, 1444, 1369, 1261, 1150, 1102, 1087, 1051, 860, 833, 779, 758, 738, 684, 632 cm$^{-1}$.

EXAMPLE 4(l)

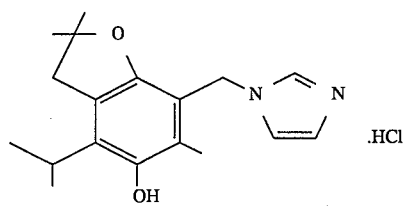

TLC:Rf 0.12 (chloroform:methanol=20:1);
IR (film):ν 3368, 2966, 1575, 1542, 1436, 1370, 1265, 1153, 1081, 1057, 886, 735 cm$^{-1}$.

EXAMPLE 4(m)

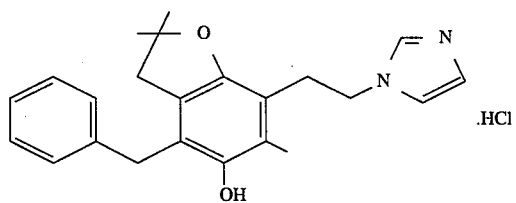

TLC:Rf 0.39 (chloroform:methanol=10:1);
IR:ν 3401, 1545, 1439, 1082, 974, 699, 630 cm$^{-1}$.

EXAMPLE 4(n)

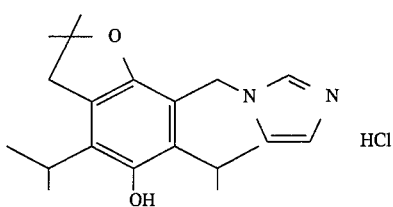

TLC:Rf 0.40 (chloroform:methanol=19:1);

IR:ν 3235, 1574, 1541, 1462, 1427, 1402, 1370, 1250, 1208, 1148, 1083, 1047, 1026, 1005, 881, 839, 739, 661, 644 cm$^{-1}$.

EXAMPLE 5

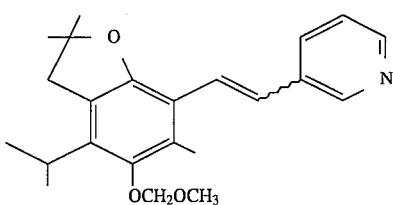

n-Butyllithium (1.07 ml, 1.6M solution in hexane) was added to a solution of 3-pyridylmethyltriphenylphosphonium chloride (220 mg) in tetrahydrofuran (5 ml) at −78° C. under an atmosphere of argon. The mixture was stirred for 1 h at 0° C. and a solution of the compound prepared in reference example 10 (100 mg) in tetrahydrofuran (3 ml) was added to the mixture at 0° C. The mixture was stirred for 1 h at room temperature. The mixture was quenched by addition of a saturated aqueous solution of sodium ammonium and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=5:1) to give the desired compound (83 mg) having the following physical data.

TLC:Rf 0.11 (hexane:ethyl acetate=5:1).

EXAMPLE 6

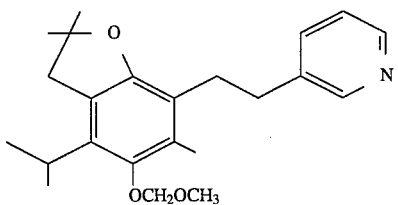

By the same procedure as reference example 15, using the compound prepared in example 5, the desired compound having the following physical data was given.

TLC:Rf 0.27 (hexane:ethyl acetate=2:1 (twice)).

EXAMPLE 7

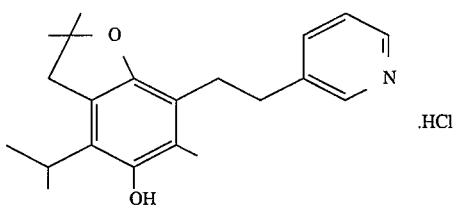

By the same procedure as example 2, using the compound prepared in example 6, the desired compound having the following physical data was given.

TLC:Rf 0.28 (hexane:ethyl acetate=1:1);

IR:ν 3401, 2962, 2623, 1656, 1554, 1430, 1371, 1277, 1162, 1113, 1053, 898, 799, 687 cm$^{-1}$.

EXAMPLE 7(a)–7(l)

By the same procedure as example 5→example 6→example 7, the following compounds were given by using corresponding aldehyde (compound prepared in reference example described hereinbefore) instead of the compound prepared in reference example 10.

EXAMPLE 7(a)

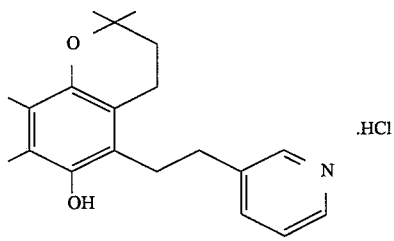

TLC:Rf 0.50 (hexane:ethyl acetate=1:2);

IR:ν 3431, 1423, 1366, 1280, 1256, 1169, 1088, 1016, 928, 715 cm$^{-1}$.

EXAMPLE 7(b)

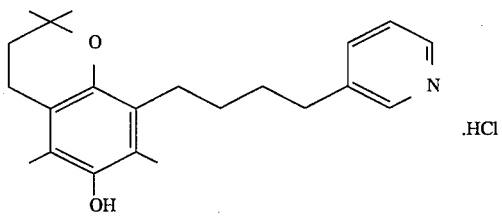

TLC:Rf 0.20 (hexane:ethyl acetate=4:1);

IR:ν 3368, 1555, 1459, 1264, 1168, 1125, 1049, 800, 681 cm$^{-1}$.

EXAMPLE 7(c)

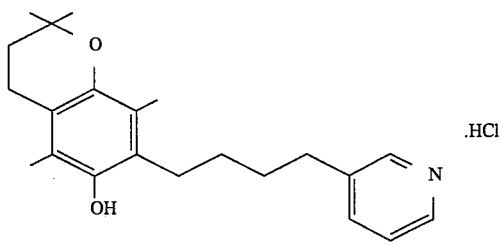

TLC:Rf 0.42 (hexane:ethyl acetate=2:1);
IR:ν 3431, 1555, 1459, 1266, 1222, 1169, 686 cm$^{-1}$.

EXAMPLE 7(d)

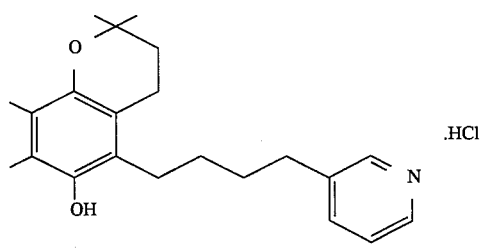

TLC:Rf 0.27 (hexane:ethyl acetate=2:1);
IR:ν 3421, 1554, 1459, 1264, 1169, 1088, 687 cm$^{-1}$.

EXAMPLE 7(e)

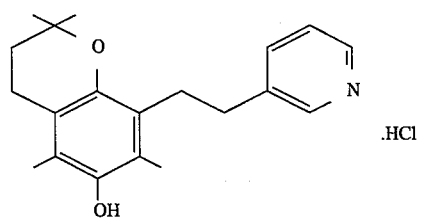

TLC:Rf 0.38 (hexane:ethyl acetate=1:1);
IR:ν 1451, 1423, 1260, 1167, 1125, 1057, 932, 717 cm$^{-1}$.

EXAMPLE 7(f)

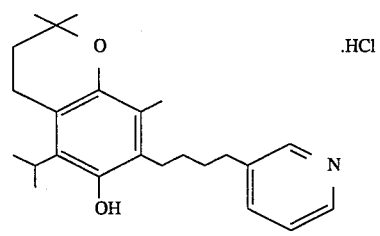

TLC:Rf 0.36 (hexane:ethyl acetate=2:1);
IR:ν 3423, 2931, 2868, 2593, 2087, 1720, 1656, 1618, 1555, 1468, 1419, 1367, 1264, 1210, 1175, 1158, 1125, 1079, 953, 804, 688, 630, 504 cm$^{-1}$.

EXAMPLE 7(g)

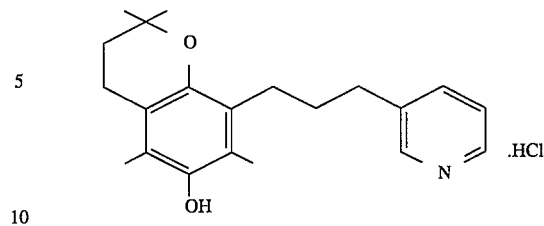

TLC:Rf 0.38 (hexane:ethyl acetate=2:1);
IR:ν 3338, 1627, 1610, 1554, 1451, 1262, 1220, 1167, 1125, 1061, 684 cm$^{-1}$.

EXAMPLE 7(h)

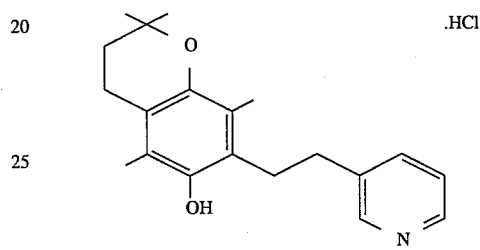

TLC:Rf 0.37 (hexane:ethyl acetate=1:1);
IR:ν 3402, 1629, 1550, 1466, 1366, 1278, 1258, 1209, 1170, 1127, 1058, 929, 798, 681 cm$^{-1}$.

EXAMPLE 7(i)

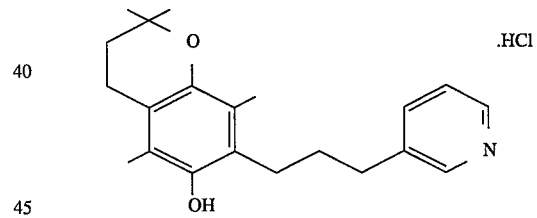

TLC:Rf 0.21 (hexane:ethyl acetate=2:1);
IR:ν 3408, 1614, 1557, 1452, 1380, 1327, 1266, 1223, 1170, 1157, 1115, 1071, 925, 901, 783, 685 cm$^{-1}$.

EXAMPLE 7(j)

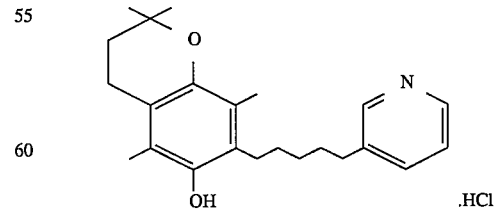

TLC:Rf 0.22 (hexane:ethyl acetate=2:1);
IR:ν 3240, 1631, 1611, 1557, 1451, 1382, 1262, 1226, 1170, 1117, 1063, 1045, 926, 788, 684 cm$^{-1}$.

EXAMPLE 7(k)

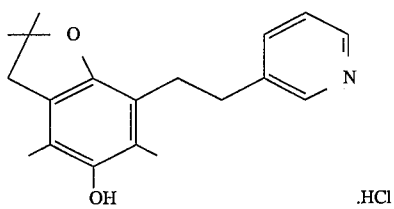

TLC:Rf 0.30 (hexane:ethyl acetate=2:3);
IR:v 3307, 3022, 2971, 2930, 2847, 2703, 1630, 1605, 1552, 1430, 1367, 1316, 1278, 1262, 1242, 1170, 1151, 1057, 1030, 882, 798, 694, 681 cm$^{-1}$.

EXAMPLE 7(l)

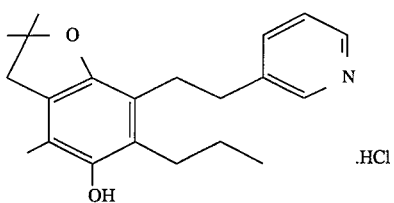

TLC:Rf 0.38 (hexane:ethyl acetate=1:1);
IR (film):v 3339, 2964, 2869, 2089, 1636, 1558, 1458, 1422, 1368, 1260, 1207, 1153, 1071, 906, 803, 730, 685 cm$^{-1}$.

REFERENCE EXAMPLE 164

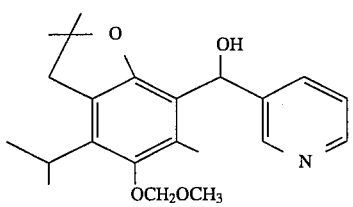

n-Butyllithium (1.0 mi, 1.6M solution in hexane) was added to a solution of 3-bromopyridine (0.18 ml) in diethyl ether (0.5 ml) at −78° C. under an atmosphere of argon. The mixture was stirred for 1 h at −78° C. and a solution of the compound prepared in reference example 11 (180 mg) in diethyl ether (3 ml) was added to the mixture. The mixture was warmed to −20° C. and stirred for 1 h. The mixture was quenched by addition of water and extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=1:1) to give the desired compound (238 mg) having the following physical data.
TLC:Rf 0.30 (hexane:ethyl acetate=1:1).

EXAMPLE 8

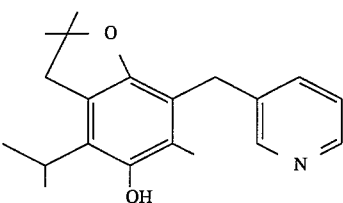

By the same procedure as reference example 71, using the compound prepared in reference example 164, the desired compound having the following physical data was given.
TLC:Rf 0.33 (hexane:ethyl acetate=1:1).

EXAMPLE 9

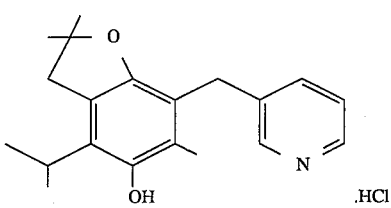

By the same procedure as example 2, using the compound prepared in example 8, the desired compound having the following physical data was given.
TLC:Rf 0.33 (hexane:ethyl acetate=1:1);
IR:v 3401, 1656, 1580, 1544, 1424, 1292, 1215, 1162, 1032, 873, 640 cm$^{-1}$.

EXAMPLE 9(a)–9(k)

By the same procedure as reference example 164→example 8→example 9, the following compounds were given by using corresponding aldehyde (compound prepared in reference example described hereinbefore) instead of the compound prepared in reference example 11.

EXAMPLE 9(a)

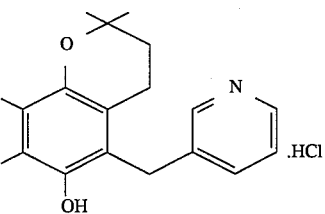

TLC:Rf 0.40 (hexane:ethyl acetate=1:1);
IR:v 3408, 1578, 1426, 1293, 1264, 1227, 1167, 1090, 710 cm$^{-1}$.

EXAMPLE 9(b)

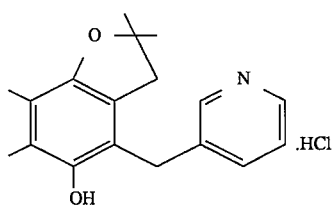

TLC:Rf 0.28 (hexane:ethyl acetate=1:1);

IR:ν 3329, 3025, 2975, 2928, 1549, 1426, 1367, 1294, 1273, 1216, 1168, 1083, 977, 916, 777, 700 cm$^{-1}$.

EXAMPLE 9(c)

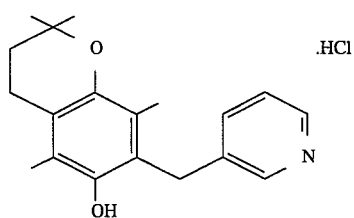

TLC:Rf 0.33 (hexane:ethyl acetate=1:1);

IR:ν 1585, 1543, 1456, 1418, 1367, 1289, 1264, 1243, 1168, 1123, 1085, 1069, 826, 762, 622 cm$^{-1}$.

EXAMPLE 9(d)

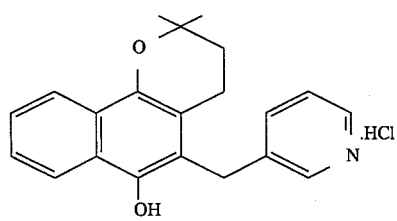

TLC:Rf 0.31 (hexane:ethyl acetate=1:1);

IR:ν 3305, 1594, 1551, 1473, 1394, 1169, 1126, 768 cm$^{-1}$.

EXAMPLE 9(e)

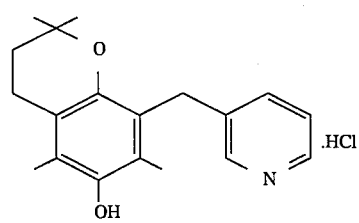

TLC:Rf 0.20 (hexane:ethyl acetate=2:1);

IR (film):ν 3369, 2928, 1612, 1553, 1454, 1370, 1265, 1226, 1165, 1124, 1057, 924, 791 cm$^{-1}$.

EXAMPLE 9(f)

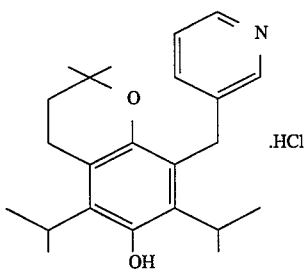

TLC:Rf 0.38 (hexane:ethyl acetate=2:1);

IR:ν 3247, 1618, 1555, 1462, 1420, 1266, 1225, 1162, 1124, 973, 789, 685 cm$^{-}$.

EXAMPLE 9(g)

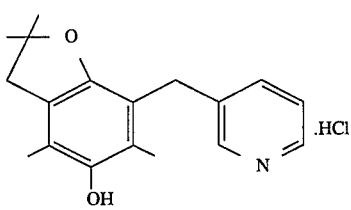

TLC:Rf 0.38 (hexane:ethyl acetate=1:4);

IR:ν 3368, 2696, 1629, 1550, 1451, 1366, 1297, 1266, 1227, 1206, 1155, 1023, 864, 695, 630 cm$^{-1}$.

EXAMPLE 9(h)

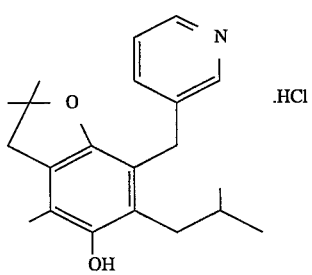

TLC:Rf 0.37 (hexane:ethyl acetate=1:1);

IR:ν 3393, 1631, 1552, 1451, 1424, 1367, 1261, 1209, 1154, 1071, 859, 781, 702 cm$^{-1}$.

EXAMPLE 9(i)

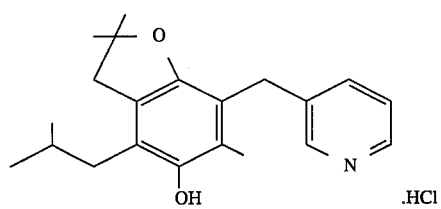

TLC:Rf 0.23 (hexane:ethyl acetate=2:1);

IR:ν 3401, 1611, 1553, 1434, 1367, 1289, 1254, 1156, 1111, 1042, 869, 785, 689 cm$^{-1}$.

EXAMPLE 9(j)

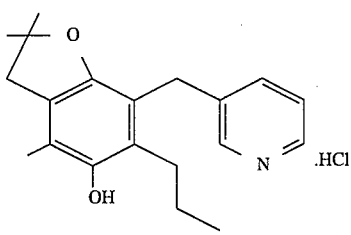

TLC:Rf 0.37 (hexane:ethyl acetate=1:1);
IR:v 3436, 2965, 1638, 1552, 1459, 1370, 1261, 1154, 1068, 758, 681 cm⁻.

EXAMPLE 9(k)

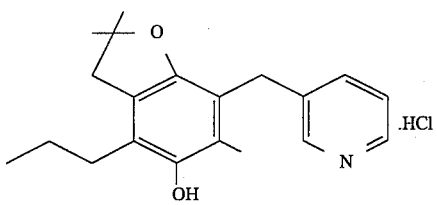

TLC:Rf 0.31 (hexane:ethyl acetate=1:1);
IR:v 3436, 2970, 1638, 1537, 1466, 1439, 1367, 1280, 1255, 1216, 1151, 1105, 1049, 869, 772, 716, 676, 592 cm$^{-1}$.

REFERENCE EXAMPLE 165

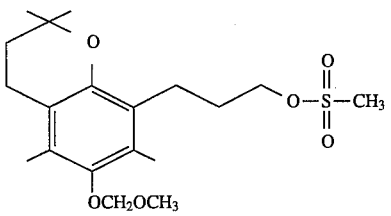

By the same procedure as reference example 163, using the compound prepared in reference example 47, the desired compound was given.

EXAMPLE 10

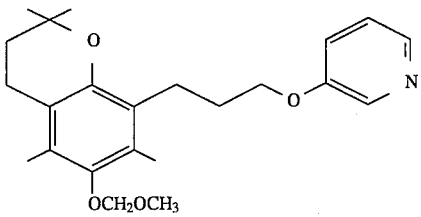

3-Hydroxypyridine (33 mg) and potassium carbonate (47 mg) were added to a solution of the compound prepared in reference example 165 (110 mg) in dimethylformamide (2 ml) under an atmosphere of argon. The mixture was stirred for 2 h at 80° C., quenched by addition of water and extracted with diethyl ether. The extract was washed with a saturated aqueous solution of sodium chloride, dried over anhydrous magnesium sulfate and concentrated. The residue was purified by column chromatography on silica gel (chloroform:methanol=40:1) to give the desired compound (71 mg) having the following physical data.

TLC:Rf 0.53 (chloroform:methanol=19:1).

EXAMPLE 11

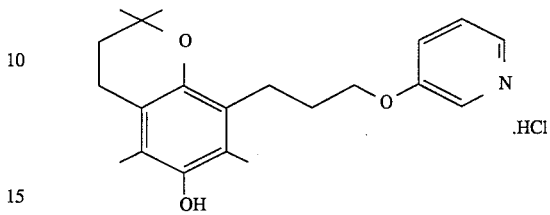

By the same procedure as example 2, using the compound prepared in example 10, the desired compound having the following physical data was given.

TLC:Rf 0.48 (chloroform:methanol=19:1);
IR:v 3392, 1618, 1551, 1451, 1367, 1283, 1265, 1225, 1166, 1124, 1049, 805, 676 cm$^{-1}$.

EXAMPLE 11(a)–11(c)

By the same procedure as example 10→example 11, the following compounds were given by using corresponding compound instead of 3-hydroxypyridine.

EXAMPLE 11(a)

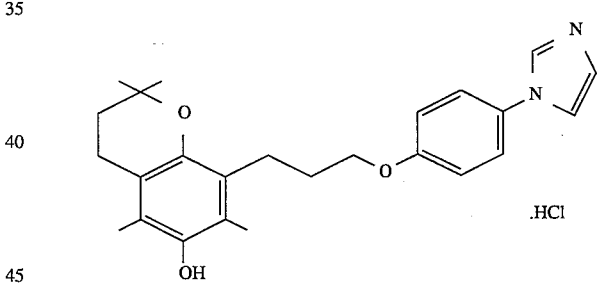

TLC:Rf 0.30 (chloroform:methanol=19:1);
IR:v 3415, 1544, 1512, 1452, 1255, 1166, 1054, 834, 621 cm$^{-1}$.

EXAMPLE 11(b)

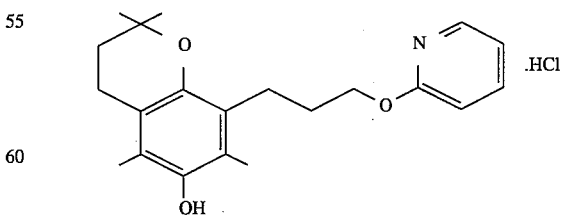

TLC:Rf 0.24 (chloroform:methanol=19:1);
IR:v 3425, 1639, 1509, 1455, 1302, 1195, 1166, 1014, 821 cm$^{-1}$.

EXAMPLE 11(c)

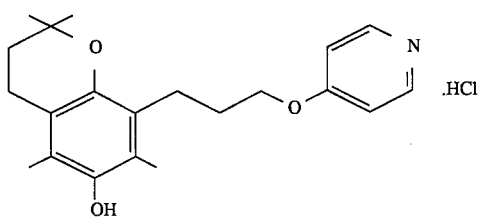

TLC:Rf 0.30 (chloroform:methanol=19:1);

IR:ν 3257, 1660, 1584, 1516, 1449, 1369, 1252, 1165, 1122, 778 cm$^{-1}$.

EXAMPLE 12

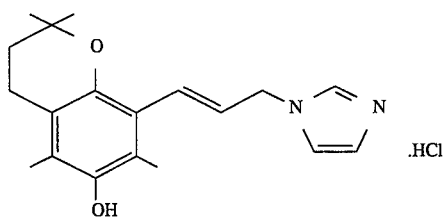

By the same procedure as reference example 45→reference example 47→reference example 163→example 1→example 2, using the compound prepared in reference example 43, the desired compound having the following physical data was given.

TLC:Rf 0.48 (chloroform:methanol=10:1);

IR (film):ν 2928, 1510, 1451, 1369, 1247, 1227, 1166, 1124, 1077, 1055, 973, 922, 819, 733 cm$^{-1}$.

EXAMPLE 13

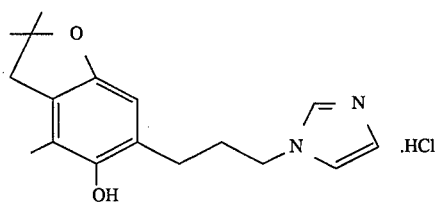

By the same procedure as reference example 162→ reference example 163→example 1→example 2, using the compound prepared in reference example 99, the desired compound having the following physical data was given.

TLC:Rf 0.35 (chloroform:methanol=9:1);

IR:ν 3327, 3044, 2965, 1577, 1544, 1454, 1368, 1278, 1234, 1206, 1085, 1044, 884, 807, 741, 621 cm$^{-1}$.

EXAMPLE 13(a)–13(d)

By the same procedure as example 13, the following compounds were given by using corresponding compound (compound prepared in reference example described hereinbefore) instead of the compound prepared in reference example 99.

EXAMPLE 13(a)

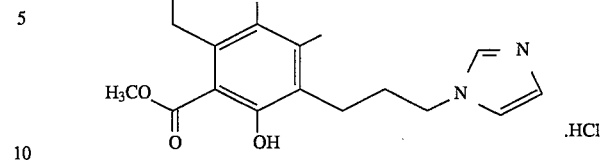

TLC:Rf 0.27 (chloroform:methanol=19:1);

IR (film):ν 2973, 1654, 1604, 1508, 1439, 1405, 1329, 1234, 1212. 1111, 1083, 952, 906, 804, 664 cm$^{-1}$.

EXAMPLE 13(b)

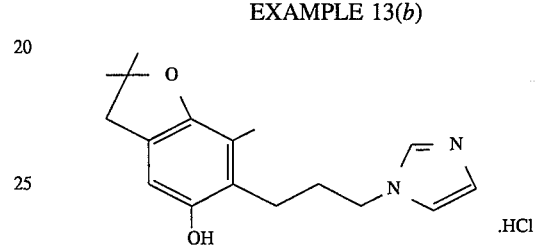

TLC:Rf 0.31 (chloroform:methanol=9:1);

IR:ν 3224, 3044, 2947, 1576, 1546, 1445, 1367, 1288, 1243, 1198, 1147, 1087, 1061, 889, 819, 736, 619 cm$^{-1}$.

EXAMPLE 13(c)

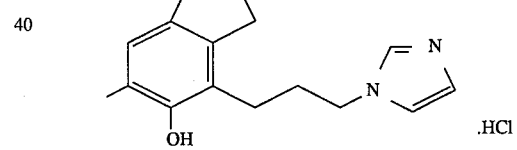

TLC:Rf 0.30 (chloroform:methanol=9:1);

IR:ν 3255, 3131, 2941, 1577, 1463, 1363, 1291, 1186, 1063, 888, 847, 786 cm$^{-1}$.

EXAMPLE 13(d)

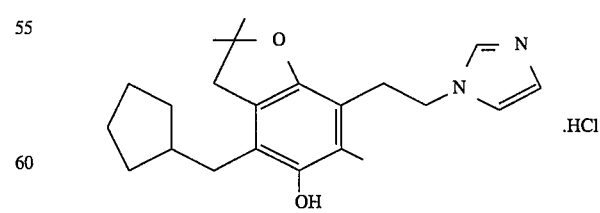

TLC:Rf 0.40 (chloroform:methanol=10:1);

IR:ν 3400, 2945, 1578, 1544, 1439, 1290, 1084, 907, 631 cm$^{-1}$.

EXAMPLE 14

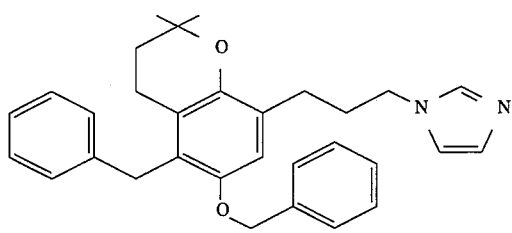

By the same procedure as reference example 162→ reference example 163→example 1, using the compound prepared in reference example 97, the desired compound having the following physical data was given.

TLC:Rf 0.26 (chloroform:methanol=20:1).

EXAMPLE 15

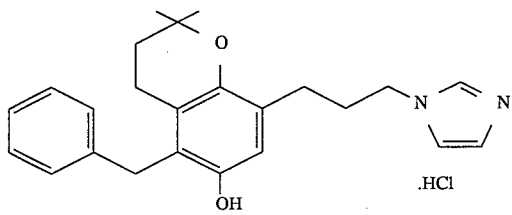

By the same procedure as reference example 15→example 2, using the compound prepared in example 14, the desired compound having the following physical data was given.

TLC:Rf 0.13 (chloroform:methanol=20:1);

IR:v 3296, 2967, 1647, 1543, 1450, 1376, 1236, 1172, 1123, 670 cm$^{-1}$.

EXAMPLE 16

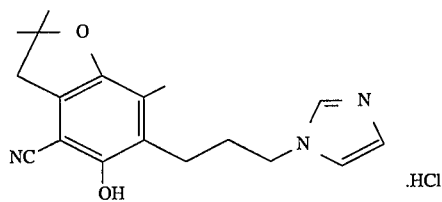

By the same procedure as example 1→reference example 15→example 2, using the compound prepared in reference example 107, the desired compound having the following physical data was given.

TLC:Rf 0.20 (chloroform:methanol=20:1);

IR (film):v 2840, 2619, 2559, 1646, 1563, 1521, 1447, 1369, 1294, 1269, 1253, 1167, 1128, 1089, 980, 832, 781, 747, 618, 490, 458 cm$^{-1}$.

EXAMPLE 17

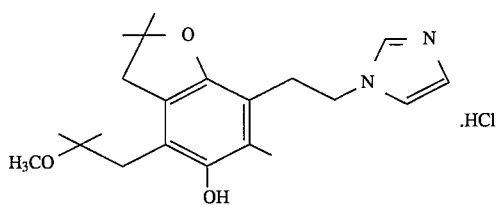

By the same procedure as reference example 163→ example 1→ example 2, using the compound prepared in reference example 111, the desired compound having the following physical data was given.

TLC:Rf 0.48 (chloroform:methanol=10:1);

IR (film):v 3369, 2972, 1577, 1427, 1368, 1289, 1269, 1213, 1157, 1137, 1068, 984, 856 cm$^{-1}$.

EXAMPLE 17(a)–17(f)

By the same procedure as example 17, the following compounds were given by using corresponding alcohol (compound prepared in reference example described hereinbefore) instead of the compound prepared in reference example 111.

EXAMPLE 17(a)

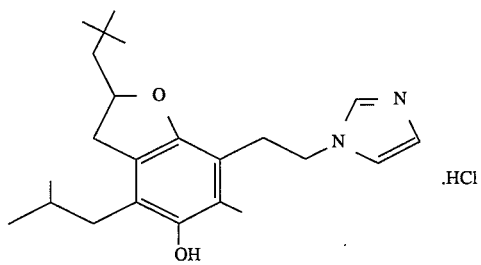

TLC:Rf 0.17 (chloroform:methanol=19:1);

IR:v 3369, 3142, 2955, 1544, 1440, 1288, 1235, 1208, 1183, 1110, 1087, 928, 750, 636 cm$^{-1}$.

EXAMPLE 17(b)

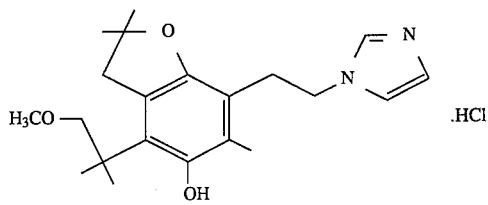

TLC:Rf 0.27 (chloroform:methanol=19:1);

IR:v 3531, 3351, 3126, 3039, 2967, 2928, 2821, 1579, 1547, 1447, 1408, 1283, 1227, 1164, 1148, 1111, 1067, 905, 636 cm$^{-1}$.

EXAMPLE 17(c)

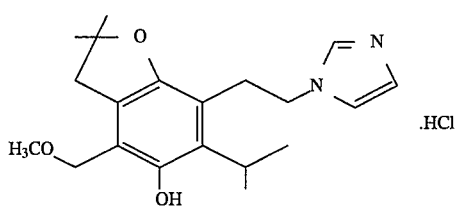

TLC:Rf 0.60 (chloroform:methanol=19:1);

IR:ν 3402, 1585, 1552, 1459, 1428, 1364, 1269, 1158, 1091, 1081, 869, 835, 626 cm$^{-1}$.

EXAMPLE 17(d)

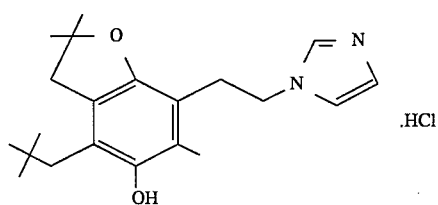

TLC:Rf 0.43 (chloroform:methanol=10:1);

IR:ν 3273, 3118, 2946, 2863, 1573, 1548, 1429, 1367, 1312, 1270, 1239, 1154, 1084, 874, 767, 637 cm$^{-1}$.

EXAMPLE 17(e)

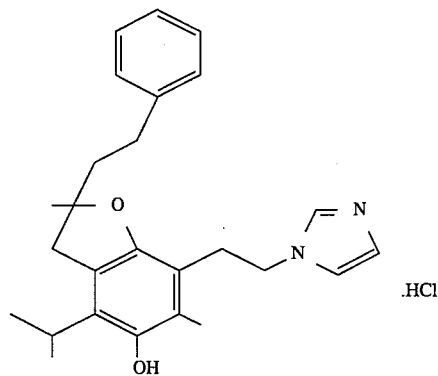

TLC:Rf 0.62 (chloroform:methanol=9:1);

IR (film):ν 3352, 3135, 3026, 2931, 2863, 2808, 2609, 1577, 1543, 1497, 1428, 1378, 1344, 1312, 1290, 1253, 1217, 1158, 1083, 1041, 906, 821, 746, 699, 671, 630 cm$^{-1}$.

EXAMPLE 17(f)

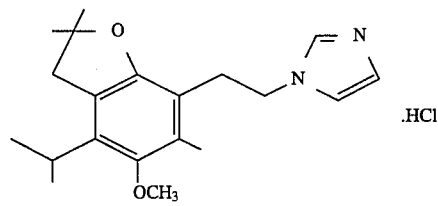

TLC:Rf 0.50 (chloroform:methanol=20:1);

IR:ν 3392, 3083, 2967, 1572, 1549, 1448, 1418, 1367, 1341, 1283, 1258, 1151, 1089, 1069, 1000, 986, 873, 628 cm$^{-1}$.

EXAMPLE 18

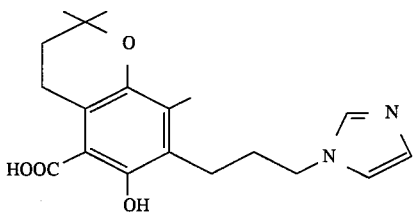

1N Aqueous solution of sodium hydroxide (0.72 ml) was added to a solution of the compound prepared in example 13(a) (170 mg) in methanol (1.5 ml). The mixture was stirred for 2 h at 60° C. and concentrated. 1N Aqueous solution of hydrochloric acid was added to the residue until pH 5 and the mixture was extracted with chloroform. The extract was washed with water and a saturated aqueous solution of sodium chloride, successively, dried over anhydrous magnesium sulfate and concentrated to give the desired compound having the following physical data.

TLC:Rf 0.10 (chloroform:methanol=19:1).

EXAMPLE 19

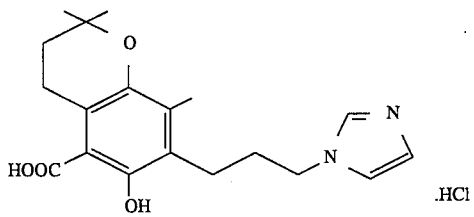

By the same procedure as example 2, using the compound prepared in example 18, the desired compound having the following physical data was given.

TLC:Rf 0.10 (chloroform:methanol=19:1);

IR (film):ν 2927, 1637, 1450, 1403, 1269, 1220, 1167, 1112, 952, 773, 732 cm$^{-1}$.

EXAMPLE 20

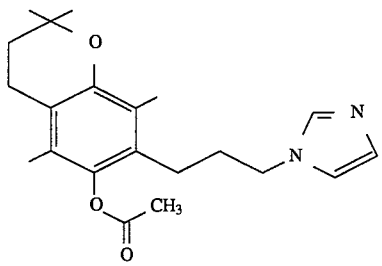

Anhydrous acetic acid (0.05 ml) was added to a solution of the compound prepared in example 2 (a) (100 mg) in pyridine (0.96 ml). The mixture was stirred at room temperature overnight. Toluene was added to the mixture and the mixture was concentrated. A saturated aqueous solution of sodium hydrogen carbonate was added to the residue and the mixture was extracted with ethyl acetate. The extract was

EXAMPLE 21

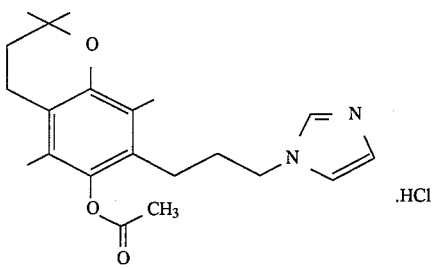

By the same procedure as example 2, using the compound prepared in example 20, the desired compound having the following physical data was given.

TLC:Rf 0.40 (chloroform:methanol=19:1);

IR:ν 3440, 2931, 1747, 1575, 1452, 1370, 1210, 1165, 1125, 1085, 1015, 927, 626 cm$^{-1}$.

EXAMPLE 22

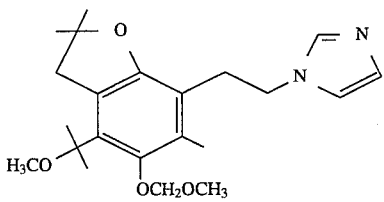

By the same procedure as reference example 163→ example 1, using the compound prepared in reference example 145, the desired compound having the following physical data was given.

TLC:Rf 0.29 (chloroform:methanol=12:1).

EXAMPLE 23

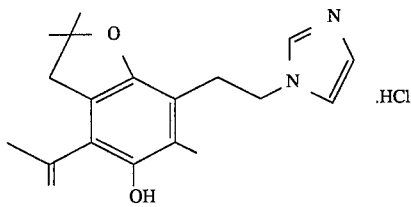

By the same procedure as example 2, using the compound prepared in example 22, the desired compound having the following physical data was given.

TLC:Rf 0.20 (chloroform:methanol=12:1);

IR:ν 3400, 1639, 1544, 1420, 1292, 906 cm$^{-1}$.

EXAMPLE 24

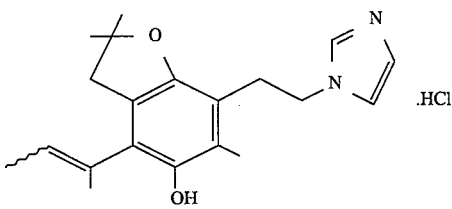

By the same procedure as example 22→example 23, using the compound prepared in reference example 146, the desired compound having the following physical data was given.

TLC:Rf 0.27 (chloroform:methanol=20:1).

EXAMPLE 24(a)

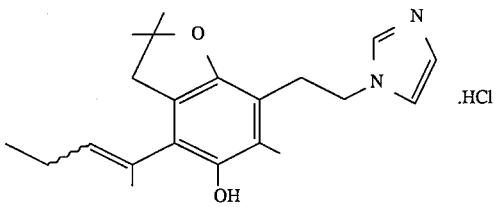

By the same procedure as example 24, using the compound prepared in reference example 147 instead of the compound prepared in reference example 146, the desired compound having the following physical data was given.

TLC:Rf 0.49 (chloroform:methanol=10:1).

EXAMPLE 25

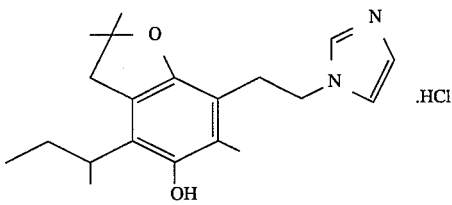

By the same procedure as reference example 15, using the compound prepared in example 24, the desired compound having the following physical data was given.

TLC:Rf 0.36 (chloroform:methanol=20:1);

IR:ν 3401, 3114, 2961, 2867, 1577, 1544, 1518, 1430, 1369, 1262, 1240, 1213, 1150, 1107, 1082, 1064, 1030, 921, 893, 831 cm$^{-1}$.

EXAMPLE 25(a)

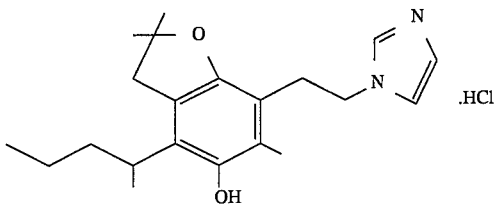

By the same procedure as example 25, using the compound prepared in example 24(a) instead of the compound prepared in example 24, the desired compound having the following physical data was given.

TLC:Rf 0.42 (chloroform:methanol=12:1);

IR:v 3400, 2955, 1578, 1544, 1426, 1290, 903, 633 cm⁻¹.

EXAMPLE 26

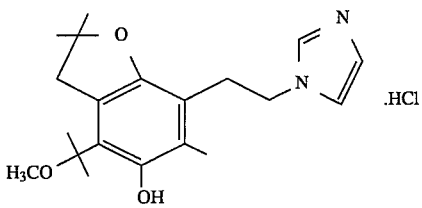

Hydrogen chloride (0.25 ml, 4N solution in dioxane) was added to a solution of the compound prepared in example 22 (170 mg) in methanol at room temperature and the mixture was stirred for 2 h. The mixture was quenched by addition of a saturated aqueous solution of sodium hydrogen carbonate and extracted with ethyl acetate. The extract was washed with water and a saturated aqueous solution of sodium chloride, successively, dried over anhydrous magnesium sulfate and concentrated to give the desired compound (137 mg) having the following physical data.

TLC:Rf 0.30 (chloroform:methanol=12:1);

IR (film):v 3271, 2973, 1509, 1408, 1368, 1279, 1194, 1158, 1109, 1052, 998, 899, 734, 663 cm⁻¹.

REFERENCE EXAMPLE 166

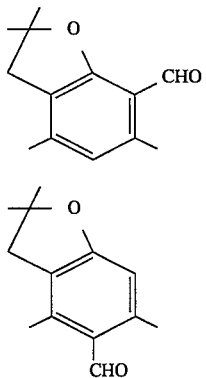

By the same procedure as reference example 5→reference example 6→reference example 7→reference example 9→reference example 10, using 3,5-dimethylphenol, the desired compound having the following physical data was given.

TLC: A: Rf 0.33 (hexane:ethyl acetate = 10:1);
B: Rf 0.22 (hexane:ethyl acetate = 10:1).

REFERENCE EXAMPLE 167

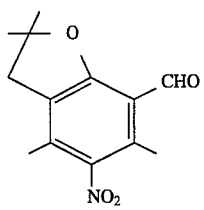

To a solution of the compound A prepared in reference example 166 (100 mg) in acetic acid (1 ml) was added nitric acid (0.1 ml) at room temperature. The reaction mixture was stirred for 1 h at 50° C. After the mixture neutralized by addition of 2N aqueous solution of sodium hydroxide, and extracted with ethyl acetate. The extract was washed with a saturated aqueous solution of sodium hydrogen carbonate, water and a saturated aqueous solution of sodium chloride, successively, dried over anhydrous magnesium sulfate and concentrated. The residue was purified by column chromatography on silica gel (hexane:ethyl acetate=10:1) to give the desired compound (71 mg) having the following physical data.

TLC:Rf 0.27 (hexane:ethyl acetate=4:1).

REFERENCE EXAMPLE 168

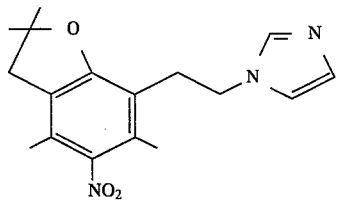

By the same procedure as reference example 161→ reference example 162→reference example 163→example 1, using the compound prepared in reference example 167, the desired compound having the following physical data was given.

TLC:Rf 0.62 (chloroform:methanol=10:1).

EXAMPLE 27

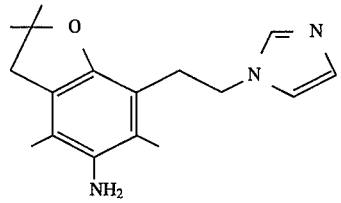

10% Palladium on activated carbon (20 mg) was added to a solution of the compound prepared in reference example 168 (211 mg) in ethanol (3 ml) and the mixture was stirred for 24 h at room temperature under an atmosphere of hydrogen. The mixture was filtered through Celite (being on sale). The filtrate was concentrated. The residue was purified by column chromatography on silica gel (chloroform:methanol=50:1→30:1) to give the desired compound (100 mg) having the following physical data.

TLC:Rf 0.49 (chloroform:methanol=10:1).

EXAMPLE 28

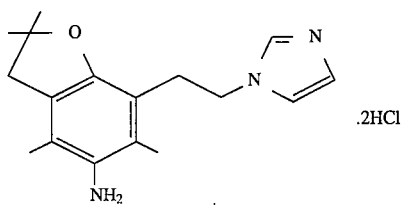

By the same procedure as example 2, using the compound prepared in example 27, the desired compound having the following physical data was given.

TLC:Rf 0.28 (ethyl acetate:acetic acid:water=3:1:1);

IR:ν 3436, 3138, 2975, 1630, 1545, 1453, 1372, 1289, 1264, 1153, 1088, 1070, 1030, 779, 624, 488 cm$^{-1}$.

EXAMPLE 29

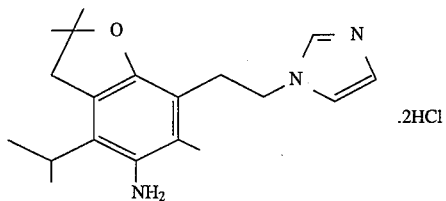

By the same procedure as reference example 166→reference example 167→reference example 168→example 27→example 28, using 3-isopropyl-5-methylphenol, the desired compound having the following physical data was given.

TLC:Rf 0.48 (chloroform:methanol=9:1);

IR:ν 3436, 2967, 1630, 1579, 1545, 1510, 1439, 1371, 1291, 1156, 1088, 641 cm$^{-1}$.

FORMULATION EXAMPLE 1

The following components were admixed in a conventional method and punched out to obtain 100 tablets each containing 50 mg of active ingredient.

| | |
|---|---|
| 5-Hydroxy-2,2,6-trimethyl-4-isopropyl-7(2-(1-imidazolyl)ethyl)-2,3-dihydrobenzofuran hydrochloride (the compound of example 2) | 5.0 g |
| Carboxymethylcellulose calcium | 0.2 g |
| Magnesium stearate | 0.1 g |
| Microcrystalline cellulose | 4.7 g |

FORMATION EXAMPLE 2

The following components were admixed in a conventional manner. The solution was sterilized in a conventional manner, placed 5 ml portions into ampoules and freeze-dried to obtain 100 ampoules each containing 20 mg of active ingredient.

| | |
|---|---|
| 5-Hydroxy-2,2,6-trimethyl-4-isopropyl-7(2-(1-imidazolyl)ethyl)-2,3-dihydrobenzofuran hydrochloride (the compound of example 2) | 5.0 g |
| Anhydrous citric acid | 0.2 g |
| Distilled water | 500 ml |

While the invention has been described in detail and with reference to specific examples thereof, it will be apparent to one skilled in the art that various changes and modifications can be made therein without departing from the spirit and scope thereof.

What we claim is:

1. A fused phenol compound of the formula (I):

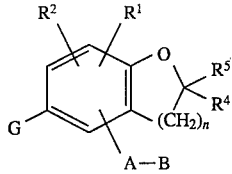

wherein $R^1$ and $R^2$ each, independently, is
1) hydrogen atom,
2) halogen atom,
3) trifluoromethyl,
4) cyano,
5) C1–10 alkyl,
6) C1–4 alkoxy,
7) C3–7 cycloalkyl,
8) C7–10 phenylalkyl,
9) C1–10 alkyl substituted by C1–4 alkoxy,
10) C1–4 alkyl substituted by C3–7 cycloalkyl,
11) C1–6 alkyl substituted by phenylthio,
12) C1–6 alkyl substituted by phenoxy,
13) —COOH,
14) —COOR$^6$ (in which R$^6$ is C1–6 alkyl),
15) C2–10 alkenyl or
16) $R^1$ and $R^2$ taken together, represent —CH=CH—CH=CH—, when $R^1$ and $R^2$ are attached ortho to each other;

A is
1) C1–8 alkylene,
2) C2–8 alkenylene,
3) C1–6 oxyalkylene or

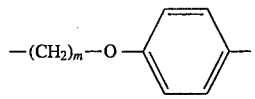

in which m is 1–6,

B is 1-imidazolyl with the proviso that B can be bonded to an oxygen in the C1–6 oxyalkylene and to phenylene in the

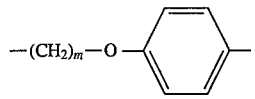

G is —OR$^{3A}$ or —NR$^{3B}$R$^{3C}$ in which R$^{3A}$, R$^{3B}$ and R$^{3C}$ each, independently, is hydrogen atom, C1–4 alkyl, C7–10 phenylalkyl, C2–5 acyl, phenylcarbonyl, C7–C10 phenylalkyl carbonyl or C2–4 alkoxyalkyl;

$R^4$ and $R^5$ each, independently, is a hydrogen atom, C1–8 alkyl, C7–10 phenylalkyl or $R^4$ and $R^5$ together with the carbon atom to which they are attached represent C4–7 cycloalkyl; and n is 1–3 with the proviso that when $R^4$ is a hydrogen atom, $R^5$ is a group other than a hydrogen atom;

a non-toxic salt thereof or non-toxic acid addition salt thereof or hydrate thereof.

2. A compound according to claim 1, wherein A is C1-8 alkylene or C2-8 alkenylene.

3. A compound according to claim 1, wherein A is C1-6 oxyalkylene or

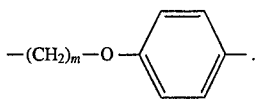

4. A compound according to claim 1, wherein $R^{3A}$ of G is a hydrogen atom.

5. A compound according to claim 1, wherein $R^{3A}$ of G is C1-4 alkyl or C7-10 phenylalkyl.

6. A compound according to claim 1, wherein $R^{3A}$ of G is C2-5 acyl, phenylcarbonyl or C7-C10 phenylalkyl carbonyl.

7. A compound according to claim 1, wherein $R^{3A}$ of G is C2-4 alkoxyalkyl.

8. A compound according to claim 1, wherein $R^{3B}$ and $R^{3C}$ of G are a hydrogen atom.

9. A compound according to claim 1, wherein $R^{3B}$ of G is a hydrogen atom, and $R^{3C}$ is C1-4 alkyl, C7-10 phenylalkyl, C2-5 acyl, phenylcarbonyl, C7-C10 phenylalkyl carbonyl or C2-4 alkoxyalkyl.

10. A compound according to claim 1, wherein $R^{3B}$ and $R^{3C}$ of G each, independently, is C1-4 alkyl, C7-10 phenylalkyl, C2-5 acyl, phenylcarbonyl, by C7-C10 phenylalkyl carboxyl or C2-4 alkoxyalkyl.

11. A compound according to claim 1, which is

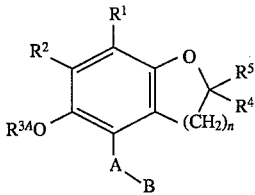

wherein $R^1$, $R^2$, $R^4$ and $R^5$ are methyl, $R^{3A}$ is a hydrogen atom, A is trimethylene, B is 1-imidazolyl, and n is 2;

$R^1$, $R^2$, $R^4$ and $R^5$ are methyl, $R^{3A}$ is a hydrogen atom, A is methylene, B is 1-imidazolyl, and n is 2;

$R^1$, $R^2$, $R^4$ and $R^5$ are methyl, $R^{3A}$ is a hydrogen atom, A is methylene, B is 1-imidazolyl, and n is 1;

$R^1$ and $R^2$, taken together, are —CH═CH—CH═CH— group, $R^4$ and $R^5$ are methyl, $R^{3A}$ is a hydrogen atom, A is methylene, B is 1-imidazolyl, and n is 2; or $R^1$ and $R^{3A}$ are each a hydrogen atom, $R^2$, $R^4$ and $R^5$ are methyl, A is trimethylene, B is 1-imidazolyl, and n is 1.

12. A compound according to claim 1, which is

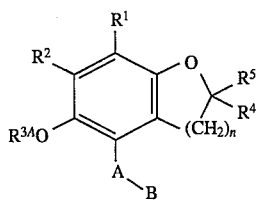

wherein $R^1$, $R^2$, $R^4$ and $R^5$ are methyl, $R^{3A}$ is a hydrogen atom, A is trimethylene, B is 1-imidazolyl, and n is 2;

$R^1$, $R^2$, $R^4$ and $R^5$ are methyl, $R^{3A}$ is a hydrogen atom, A is tetramethylene, B is 1-imidazolyl, and n is 2;

$R^1$, $R^2$, $R^4$ and $R^5$ are methyl, $R^{3A}$ is a hydrogen atom, A is ethylene, B is 1-imidazolyl, and n is 2;

$R^1$, $R^2$, $R^4$ and $R^5$ are methyl, $R^{3A}$ is a hydrogen atom, A is methylene, B is 1-imidazolyl, and n is 2;

$R^1$, $R^2$, $R^4$ and $R^5$ are methyl, $R^{3A}$ is a hydrogen atom, A is pentamethylene, B is 1-imidazolyl, and n is 2;

$R^1$, $R^4$ and $R^5$ are methyl, $R^2$ is isopropyl, $R^{3A}$ is a hydrogen atom, A is trimethylene, B is 1-imidazolyl, and n is 2;

$R^1$, $R^2$, $R^4$ and $R^5$ are methyl, $R^{3A}$ is a hydrogen atom, A is trimethylene, B is 1-imidazolyl, and n is 1;

$R^1$, $R^4$ and $R^5$ are methyl, $R^2$ and $R^{3A}$ are each a hydrogen atom, A is trimethylene, B is 1-imidazolyl, and n is 2;

$R^1$, $R^4$ and $R^5$ are methyl, $R^2$ is propyl, $R^{3A}$ is a hydrogen atom, A is trimethylene, B is 1-imidazolyl, and n is 2;

$R^1$ and $R^{3A}$ are each a hydrogen atom, $R^2$, $R^4$ and $R^5$ are methyl, A is trimethylene, B is 1-imidazolyl, and n is 1;

$R^1$, $R^4$ and $R^5$ are methyl, $R^2$ is methoxycarbonyl, $R^{3A}$ is a hydrogen atom, A is trimethylene, B is 1-imidazolyl, and n is 2;

$R^1$, $R^4$ and $R^5$ are methyl, $R^2$ and $R^{3A}$ are each a hydrogen atom, A is trimethylene, B is 1-imidazolyl, and n is 1;

$R^1$, $R^4$ and $R^5$ are methyl, $R^2$ is cyano, $R^{3A}$ is a hydrogen atom, A is trimethylene, B is 1-imidazolyl, and n is 1;

$R^1$, $R^4$ and $R^5$ are methyl, $R^2$ is carboxyl, $R^{3A}$ is a hydrogen atom, A is trimethylene, B is 1-imidazolyl, and n is 2; or $R^1$, $R^2$, $R^4$ and $R^5$ are methyl, $R^{3A}$ is acetyl, A is trimethylene, B is 1-imidazolyl, and n is 2.

13. A compound according to claim 1, which is

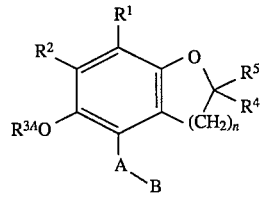

wherein $R^1$, $R^4$ and $R^5$ are methyl, $R^2$ is isopropyl, $R^{3A}$ is methoxymethyl, A is ethylene, B is 1-imidazolyl, and n is 1;

$R^1$, $R^4$ and $R^5$ are methyl, $R^2$ is isopropyl, $R^{3A}$ is a hydrogen atom, A is ethylene, B is 1-imidazolyl, and n is 1;

$R^1$, $R^2$, $R^4$ and $R^5$ are methyl, $R^{3A}$ is a hydrogen atom, A is ethylene, B is 1-imidazolyl, and n is 2;

$R^1$, $R^2$, $R^4$ and $R^5$ are methyl, $R^{3A}$ is a hydrogen atom, A is ethylene, B is 1-imidazolyl, and n is 1;

$R^1$, $R^4$ and $R^5$ are methyl, $R^2$ is isobutyl, $R^{3A}$ is a hydrogen atom, A is ethylene, B is 1-imidazolyl, and n is 1;

$R^1$ is isobutyl, $R^2$, $R^4$ and $R^5$ are methyl, $R^{3A}$ is a hydrogen atom, A is ethylene, B is 1-imidazolyl, and n is 1;

$R^1$ is propyl, $R^2$, $R^4$ and $R^5$ are methyl, $R^{3A}$ is a hydrogen atom, A is ethylene, B is 1-imidazolyl, and n is 1;

$R^1$, $R^4$ and $R^5$ are methyl, $R^2$ is propyl, $R^{3A}$ is a hydrogen atom, A is ethylene, B is 1-imidazolyl, and n is 1;

$R^1$ is ethyl, $R^2$ is isobutyl, $R^4$ and $R^5$ are methyl, $R^{3A}$ is a hydrogen atom, A is ethylene, B is 1-imidazolyl, and n is 1;

$R^1$, $R^4$ and $R^5$ are methyl, $R^2$ is butyl, $R^{3A}$ is a hydrogen atom, A is ethylene, B is 1-imidazolyl, and n is 1;

$R^1$, $R^4$ and $R^5$ are methyl, $R^2$ is hexyl, $R^{3A}$ is a hydrogen atom, A is ethylene, B is 1-imidazolyl, and n is 1;

$R^1$, $R^4$ and $R^5$ are methyl, $R^2$ is pentyl, $R^{3A}$ is a hydrogen atom, A is ethylene, B is 1-imidazolyl, and n is 1;

$R^1$, $R^4$ and $R^5$ are methyl, $R^2$ is isopentyl, $R^{3A}$ is a hydrogen atom, A is ethylene, B is 1-imidazolyl, and n is 1;

$R^1$, $R^4$ and $R^5$ are methyl, $R^2$ is isohexyl, $R^{3A}$ is hydrogen atom, A is ethylene, B is 1-imidazolyl, and n is 1;

$R^1$ and $R^2$ are isopropyl, $R^4$ and $R^5$ are methyl, $R^{3A}$ is a hydrogen atom, A is ethylene, B is 1-imidazolyl, and n is 1;

$R^1$ is isopropyl, $R^2$, $R^4$ and $R^5$ are methyl, $R^{3A}$ is hydrogen atom, A is ethylene, B is 1-imidazolyl, and n is 1;

$R^1$ and $R^2$ are propyl, $R^4$ and $R^5$ are methyl, $R^{3A}$ is a hydrogen atom, A is ethylene, B is 1-imidazolyl, and n is 1;

$R^1$, $R^4$ and $R^5$ are methyl, $R^2$ is tert-butyl, $R^{3A}$ is a hydrogen atom, A is ethylene, B is 1-imidazolyl, and n is 1;

$R^1$ and $R^2$ are methoxy, $R^4$ and $R^5$ are methyl, $R^{3A}$ is a hydrogen atom, A is ethylene, B is 1-imidazolyl, and n is 1;

$R^1$, $R^4$ and $R^5$ are methyl, $R^2$ is 3-(phenylthio)propyl, $R^{3A}$ is a hydrogen atom, A is ethylene, B is 1-imidazolyl, and n is 1;

$R^1$ is propyl, $R^2$ is isopropyl, $R^4$ and $R^5$ are methyl, $R^{3A}$ is a hydrogen atom, A is ethylene, B is 1-imidazolyl, and n is 1;

$R^1$ is methyl, $R^2$ is isobutyl, $R^4$, $R^5$ and a carbon atom to which they bond, taken together, is cyclopentyl, $R^{3A}$ is a hydrogen atom, A is ethylene, B is 1-imidazolyl, and n is 1;

$R^1$ is isopropyl, $R^2$ is propyl, $R^4$ and $R^5$ are methyl, $R^{3A}$ is a hydrogen atom, A is ethylene, B is 1-imidazolyl, and n is 1;

$R^1$, $R^2$, $R^4$ and $R^5$ are methyl, $R^{3A}$ is a hydrogen atom, A is tetramethylene, B is 1-imidazolyl, and n is 2;

$R^1$, $R^2$, $R^4$ and $R^5$ are methyl, $R^{3A}$ is a hydrogen atom, A is pentamethylene, B is 1-imidazolyl, and n is 2;

$R^1$, $R^2$, $R^4$ and $R^5$ are methyl, $R^{3A}$ is a hydrogen atom, A is trimethylene, B is 1-imidazolyl, and n is 1;

$R^1$ is isobutyl, $R^2$, $R^4$ and $R^5$ are methyl, $R^{3A}$ is a hydrogen atom, A is trimethylene, B is 1-imidazolyl, and n is 1;

$R^1$, $R^4$ and $R^5$ are methyl, $R^2$ is isobutyl, $R^{3A}$ is a hydrogen atom, A is trimethylene, B is 1-imidazolyl, and n is 1;

$R^1$ is propyl, $R^2$, $R^4$ and $R^5$ are methyl, $R^{3A}$ is hydrogen atom, A is trimethylene, B is 1-imidazolyl, and n is 1;

$R^1$ is isopropyl, $R^2$, $R^4$ and $R^5$ are methyl, $R^{3A}$ is a hydrogen atom, A is trimethylene, B is 1-imidazolyl, and n is 1;

$R^1$, $R^4$ and $R^5$ are methyl, $R^2$ is propyl, $R^{3A}$ is a hydrogen atom, A is trimethylene, B is 1-imidazolyl, and n is 1;

$R^1$, $R^4$ and $R^5$ are methyl, $R^2$ is isopropyl, $R^{3A}$ is a hydrogen atom, A is trimethylene, B is 1-imidazolyl, and n is 1;

$R^1$, $R^2$, $R^4$ and $R^5$ are methyl, $R^{3A}$ is a hydrogen atom, A is trimethylene, B is 1-imidazolyl, and n is 2;

$R^1$, $R^2$, $R^4$ and $R^5$ are methyl, $R^{3A}$ is a hydrogen atom, A is methylene, B is 1-imidazolyl, and n is 2;

$R^1$, $R^2$, $R^4$ and $R^5$ are methyl, $R^{3A}$ is a hydrogen atom, A is methylene, B is 1-imidazolyl, and n is 1;

$R^1$ is isobutyl, $R^2$, $R^4$ and $R^5$ are methyl, $R^3$ is a hydrogen atom, A is methylene, B is 1-imidazolyl, and n is 1;

$R^1$, $R^4$ and $R^5$ are methyl, $R^2$ is isobutyl, $R^{3A}$ is a hydrogen atom, A is methylene, B is 1-imidazolyl, and n is 1;

$R^1$ is propyl, $R^2$, $R^4$ and $R^5$ are methyl, $R^{3A}$ is a hydrogen atom, A is methylene, B is 1-imidazolyl, and n is 1;

$R^1$ is isopropyl, $R^2$, $R^4$ and $R^5$ are methyl, $R^{3A}$ is a hydrogen atom, A is methylene, B is 1-imidazolyl, and n is 1;

$R^1$, $R^4$ and $R^5$ are methyl, $R^2$ is propyl, $R^{3A}$ is a hydrogen atom, A is methylene, B is 1-imidazolyl, and n is 1;

$R^1$, $R^4$ and $R^5$ are methyl, $R^2$ is isopropyl, $R^{3A}$ is a hydrogen atom, A is methylene, B is 1-imidazolyl, and n is 1;

$R^1$, $R^4$ and $R^5$ are methyl, $R^2$ is benzyl, $R^{3A}$ is a hydrogen atom, A is ethylene, B is 1-imidazolyl, and n is 1;

$R^1$, $R^2$, $R^4$ and $R^5$ are methyl, $R^{3A}$ is a hydrogen atom, A is 3-(phenyleneoxy)trimethylene ($-CH_2-CH_2-CH_2-O-C_6H_4-$), B is 1-imidazolyl, and n is 2;

$R^1$, $R^2$, $R^4$ and $R^5$ are methyl, $R^{3A}$ is a hydrogen atom, A is 1-propenylene ($-CH=CH-CH_2-$), B is 1-imidazolyl, and n is 2;

$R^1$, $R^4$ and $R^5$ are methyl, $R^2$ is cyclopentylmethyl, $R^{3A}$ is a hydrogen atom, A is ethylene, B is 1-imidazolyl, and n is 1;

$R^1$ is hydrogen atom, $R^2$ and $R^{3A}$ are benzyl, $R^4$ and $R^5$ are methyl, A is trimethylene, B is 1-imidazolyl, and n is 2;

$R^1$ and $R^{3A}$ are each a hydrogen atom, $R^2$ is benzyl, $R^4$ and $R^5$ are methyl, A is trimethylene, B is 1-imidazolyl, and n is 2;

$R^1$, $R^4$ and $R^5$ are methyl, $R^2$ is 2-methyl-2-methoxypropyl, $R^{3A}$ is a hydrogen atom, A is ethylene, B is 1-imidazolyl, and n is 1;

$R^1$ is methyl, $R^2$ is isobutyl, $R^{3A}$ and $R^4$ are each a hydrogen atom, $R^5$ is 2,2-dimethylpropyl, A is ethylene, B is 1-imidazolyl, and n is 1;

$R^1$, $R^4$ and $R^5$ are methyl, $R^2$ is 3-phenylpropyl, $R^{3A}$ is a hydrogen atom, A is ethylene, B is 1-imidazolyl, and n is 1;

$R^1$, $R^4$ and $R^5$ are methyl, $R^2$ is isopropyl, $R^{3A}$ is a hydrogen atom, A is ethylene, B is 1-imidazolyl, and n is 2;

$R^1$ and $R^2$ are isopropyl, $R^4$ and $R^5$ are methyl, $R^{3A}$ is a hydrogen atom, A is methylene, B is 1-imidazolyl, and n is 1;

$R^1$ is 3-(phenylthio)propyl, $R^2$, $R^4$ and $R^5$ are methyl, $R^{3A}$ is hydrogen atom, A is ethylene, B is 1-imidazolyl, and n is 1;

$R^1$, $R^4$ and $R^5$ are methyl, $R^2$ is 1-ethylpropyl, $R^{3A}$ is a hydrogen atom, A is ethylene, B is 1-imidazolyl, and n is 1;

$R^1$ is 3-phenylpropyl, $R^2$, $R^4$ and $R^5$ are methyl, $R^{3A}$ is a hydrogen atom, A is ethylene, B is 1-imidazolyl, and n is 1;

$R^1$ is isopropyl, $R^2$ is ethyl, $R^4$ and $R^5$ are methyl, $R^{3A}$ is a hydrogen atom, A is ethylene, B is 1-imidazolyl, and n is 1;

$R^1$ is ethyl, $R^2$ is isopropyl, $R^4$ and $R^5$ are methyl, $R^{3A}$ is a hydrogen atom, A is ethylene, B is 1-imidazolyl, and n is 1;

$R^1$ is isopropyl, $R^2$ is 3-methoxypropyl, $R^4$ and $R^5$ are methyl, $R^{3A}$ is a hydrogen atom, A is ethylene, B is 1-imidazolyl, and n is 1;

$R^1$ is 3-methoxypropyl, $R^2$ is isopropyl, $R^4$ and $R^5$ are methyl, $R^{3A}$ is a hydrogen atom, A is ethylene, B is 1-imidazolyl, and n is 1;

$R^1$, $R^4$ and $R^5$ are methyl, $R^2$ is 1,1-dimethyl-2-methoxyethyl, $R^{3A}$ is a hydrogen atom, A is ethylene, B is 1-imidazolyl, and n is 1;

$R^1$, $R^4$ and $R^5$ are methyl, $R^2$ is 1-methylethenyl, $R^{3A}$ is a hydrogen atom, A is ethylene, B is 1-imidazolyl, and n is 1;

$R^1$ is isopropyl, $R^2$ is methoxymethyl, $R^4$ and $R^5$ are methyl, $R^{3A}$ is a hydrogen atom, A is ethylene, B is 1-imidazolyl, and n is 1;

$R^1$, $R^4$ and $R^5$ are methyl, $R^2$ is 1-methyl-1-methoxyethyl, $R^{3A}$ is a hydrogen atom, A is ethylene, B is 1-imidazolyl, and n is 1;

$R^1$, $R^4$ and $R^5$ are methyl, $R^2$ is 2,2-dimethylpropyl, $R^{3A}$ is a hydrogen atom, A is ethylene, B is 1-imidazolyl, and n is 1;

$R^1$, $R^4$ and $R^5$ are methyl, $R^2$ is 1-methylpropyl, $R^{3A}$ is a hydrogen atom, A is ethylene, B is 1-imidazolyl, and n is 1;

$R^1$, $R^4$ and $R^5$ are methyl, $R^2$ is 1-methylbutyl, $R^{3A}$ is a hydrogen atom, A is ethylene, B is 1-imidazolyl, and n is 1;

$R^1$ and $R^{3A}$ are each a hydrogen atom, $R^2$ is isopropyl, $R^4$ and $R^5$ are methyl, A is ethylene, B is 1-imidazolyl, and n is 1;

$R^1$ is methoxy, $R^2$ is isopropyl, $R^4$ and $R^5$ are methyl, $R^{3A}$ is a hydrogen atom, A is ethylene, B is 1-imidazolyl, and n is 1;

$R^1$ is isopropyl, $R^2$ is a chlorine atom, $R^4$ and $R^5$ are methyl, $R^{3A}$ is a hydrogen atom, A is ethylene, B is 1-imidazolyl, and n is 1;

$R^1$ is isopropyl, $R^2$ is 3-phenylpropyl, $R^4$ and $R^5$ are methyl, $R^{3A}$ is a hydrogen atom, A is ethylene, B is 1-imidazolyl, and n is 1;

$R^1$, $R^{3A}$, $R^4$ and $R^5$ are methyl, $R^2$ is isopropyl, A is ethylene, B is 1-imidazolyl, and n is 1; or $R^1$ and $R^4$ are methyl, $R^2$ is isopropyl, $R^{3A}$ is a hydrogen atom, $R^5$ is 2-phenylethyl, A is ethylene, B is 1-imidazolyl, and n is 1.

14. A compound according to claim 1, which is

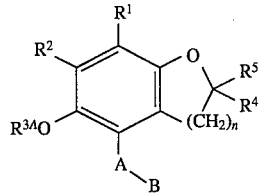

wherein $R^1$, $R^2$, $R^4$ and $R^5$ are methyl, $R^{3B}$ and $R^{3C}$ are each a hydrogen atom, A is ethylene, B is 1-imidazolyl, and n is 1; or $R^1$, $R^4$ and $R^5$ are methyl, $R^2$ is isopropyl, $R^{3B}$ and $R^{3C}$ are each a hydrogen atom, A is ethylene, B is 1-imidazolyl, and n is 1.

15. A pharmaceutical composition which comprises, as an active ingredient, an effective amount of a fused phenol compound of the formula (I) depicted in claim 1, a non-toxic salt, or a non-toxic acid addition salt thereof or hydrates thereof, and a pharmaceutical carrier or coating.

* * * * *

UNITED STATES PATENT AND TRADEMARK OFFICE
CERTIFICATE OF CORRECTION

PATENT NO. : 5,534,536

DATED : July 9, 1996

INVENTOR(S) : OHUCHIDA et al.

It is certified that error appears in the above-identified patent and that said Letters Patent is hereby corrected as shown below:

Please change Formula in Claim 12

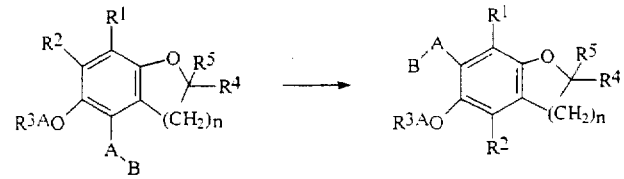

Please change Formula in Claim 13

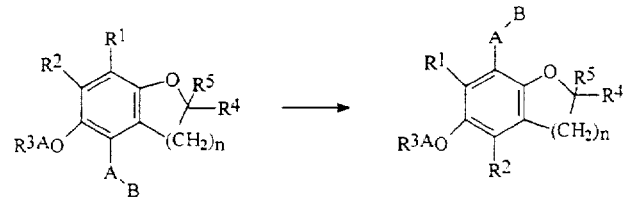

Please change Formula in Claim 14

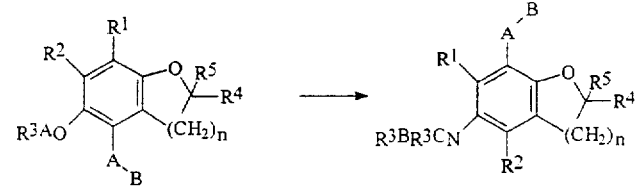

UNITED STATES PATENT AND TRADEMARK OFFICE
CERTIFICATE OF CORRECTION

PATENT NO. : 5,534,536
DATED : July 9, 1996
INVENTOR(S) : OHUCHIDA et al

It is certified that error appears in the above-identified patent and that said Letters Patent is hereby corrected as shown below:

Claim 13, line 17, "$R^1$" should be amended to --$R^1$--.

Signed and Sealed this

Ninth Day of May, 2000

Q. TODD DICKINSON

*Attest:*

*Attesting Officer*  *Director of Patents and Trademarks*